United States Patent
McLoughlin et al.

(10) Patent No.: US 9,757,521 B2
(45) Date of Patent: Sep. 12, 2017

(54) AUTO-INJECTOR

(71) Applicant: UCB Biopharma SPRL, Brussels (BE)

(72) Inventors: Martin John McLoughlin, Burnham (GB); Michael James David Heald, Maidenhead (GB); Ilario Melzi, Milan (IT); Stefan Verlaak, Paderno D'adda (IT); Tatiana Palombi, Cologno Monzese (IT)

(73) Assignee: UCB Biopharma SPRL, Brussels (BE)

( * ) Notice: Subject to any disclaimer, the term of this patent is extended or adjusted under 35 U.S.C. 154(b) by 313 days.

(21) Appl. No.: 14/418,440

(22) PCT Filed: Jul. 29, 2013

(86) PCT No.: PCT/EP2013/065939
§ 371 (c)(1),
(2) Date: Jan. 29, 2015

(87) PCT Pub. No.: WO2014/020000
PCT Pub. Date: Feb. 6, 2014

(65) Prior Publication Data
US 2015/0258278 A1    Sep. 17, 2015

(30) Foreign Application Priority Data

Jul. 30, 2012  (GB) .................................. 1213502.6
Dec. 12, 2012  (GB) .................................. 1222353.3

(51) Int. Cl.
*A61M 5/20* (2006.01)
*A61M 5/32* (2006.01)
*A61M 5/315* (2006.01)

(52) U.S. Cl.
CPC ............ *A61M 5/2053* (2013.01); *A61M 5/20* (2013.01); *A61M 5/315* (2013.01);
(Continued)

(58) Field of Classification Search
CPC ............ A61M 2005/2073; A61M 5/20; A61M 5/315; A61M 2005/2086; A61M 5/1458
See application file for complete search history.

(56) References Cited

U.S. PATENT DOCUMENTS 2,966,910 A    1/1961  Camber
3,395,704 A    8/1968  Fray et al.
(Continued)

FOREIGN PATENT DOCUMENTS

DE    202009001836 U1    5/2009
EP    0 518 416 A1    12/1992
(Continued)

OTHER PUBLICATIONS

International Search Report PCT/EP2013/065940 dated Nov. 4, 2013.
(Continued)

*Primary Examiner* — Kevin C Sirmons
*Assistant Examiner* — Deanna K Hall
(74) *Attorney, Agent, or Firm* — Muncy, Geissler, Olds & Lowe, P.C.

(57) ABSTRACT

Provided is a cassette unit suitable for use with an auto-injector having an electrically powered drive unit. The cassette unit comprises a cassette unit housing defining a cassette unit housing cavity, a rearward entrance to said cavity and a forward needle projection aperture. The housing cavity may receive a syringe comprising a barrel; a needle at a front end of the barrel; and a plunger that is axially movable within the barrel. The cassette unit also comprises in capping relationship with the rearward entrance of the cassette unit housing, a cassette unit end-cap, said cassette unit end-cap defining a drive rod-receiving opening for receipt of a drive rod for providing forward axial drive to said plunger; and a biasing element defining a biasing (Continued)

relationship between the cassette unit end-cap and an end flange of the syringe barrel, thereby urging the syringe forwards in relation to the cassette unit end cap.

57 Claims, 50 Drawing Sheets

(52) U.S. Cl.
CPC ........ *A61M 5/3202* (2013.01); *A61M 5/3213* (2013.01); *A61M 2005/2026* (2013.01); *A61M 2005/2073* (2013.01)

(56) References Cited

U.S. PATENT DOCUMENTS

| | | | |
|---|---|---|---|
| 4,950,246 | A | 8/1990 | Muller |
| 5,662,617 | A | 9/1997 | Odell et al. |
| D439,657 | S | 3/2001 | Bridle |
| 6,368,307 | B1 | 4/2002 | Ziemba et al. |
| 6,558,353 | B2 | 5/2003 | Zohmann |
| D484,244 | S | 12/2003 | Starnes |
| 6,869,418 | B2 | 3/2005 | Marano-Ford |
| D543,273 | S | 5/2007 | Young et al. |
| 7,811,260 | B2 | 10/2010 | Miller et al. |
| D636,088 | S | 4/2011 | Loew et al. |
| D650,070 | S | 12/2011 | Mori |
| D652,512 | S | 1/2012 | Sherwood et al. |
| D652,513 | S | 1/2012 | Sherwood et al. |
| D652,919 | S | 1/2012 | Sherwood et al. |
| 8,277,437 | B2 | 10/2012 | Saal et al. |
| D671,638 | S | 11/2012 | Young et al. |
| 8,454,560 | B2 | 6/2013 | Strobl |
| 8,469,922 | B2 | 6/2013 | Langley et al. |
| 8,591,463 | B1 | 11/2013 | Cowe |
| D695,395 | S | 12/2013 | Tani et al. |
| D695,396 | S | 12/2013 | Tani et al. |
| D696,770 | S | 12/2013 | Schneider et al. |
| 8,834,429 | B2 | 9/2014 | Grant et al. |
| D724,203 | S | 3/2015 | McLoughlin et al. |
| D726,901 | S | 4/2015 | McLoughlin et al. |
| D726,902 | S | 4/2015 | McLoughlin et al. |
| D755,956 | S | 5/2016 | McLoughlin et al. |
| 2009/0182284 | A1 | 7/2009 | Morgan |
| 2010/0016795 | A1 | 1/2010 | McLoughlin |
| 2010/0298780 | A1 | 11/2010 | Laiosa |
| 2011/0009830 | A1 | 1/2011 | Kosinski et al. |
| 2011/0224616 | A1 | 9/2011 | Slate et al. |
| 2012/0053528 | A1 | 3/2012 | Bollenbach et al. |
| 2013/0221097 | A1 | 8/2013 | Day et al. |
| 2013/0226139 | A1 | 8/2013 | Day et al. |
| 2013/0281936 | A1 | 10/2013 | Kemp et al. |
| 2014/0018744 | A1 | 1/2014 | Holmqvist |
| 2014/0358072 | A1 | 12/2014 | McLoughlin et al. |
| 2014/0358083 | A1 | 12/2014 | McLoughlin et al. |
| 2015/0045734 | A1 | 2/2015 | McLoughlin et al. |
| 2015/0165135 | A1 | 6/2015 | McLoughlin et al. |
| 2015/0182691 | A1 | 7/2015 | McLoughlin et al. |
| 2015/0202374 | A1 | 7/2015 | McLoughlin et al. |
| 2015/0258278 | A1 | 9/2015 | McLoughlin et al. |
| 2017/0000955 | A1 | 1/2017 | McLoughlin et al. |
| 2017/0007763 | A1 | 1/2017 | McLoughlin et al. |

FOREIGN PATENT DOCUMENTS

| | | |
|---|---|---|
| EP | 0 824 923 A1 | 2/1998 |
| EP | 0 897 728 A1 | 2/1999 |
| EP | 2384778 A1 | 11/2011 |
| GB | 2 437 922 A | 11/2007 |
| GB | 2 438 593 A | 12/2007 |
| GB | 2467637 A | 8/2010 |
| WO | WO-01/37905 A2 | 5/2001 |
| WO | WO-02/09797 A1 | 2/2002 |
| WO | WO-02/100467 A2 | 12/2002 |
| WO | WO-03/101368 A2 | 12/2003 |
| WO | WO-03/101527 A1 | 12/2003 |
| WO | WO 2004/043524 A1 | 5/2004 |
| WO | WO-2005/097233 A2 | 10/2005 |
| WO | WO 2006/91695 A1 | 8/2006 |
| WO | WO-2006/091695 A1 | 8/2006 |
| WO | WO-2006/108026 A2 | 10/2006 |
| WO | WO-2009/040603 A1 | 4/2009 |
| WO | WO 2009/040603 A1 | 4/2009 |
| WO | WO 2009/066130 A1 | 5/2009 |
| WO | WO-2009/081103 A1 | 7/2009 |
| WO | WO 2009/081103 A1 | 7/2009 |
| WO | WO-2009/087355 A1 | 7/2009 |
| WO | WO 2009/087355 A1 | 7/2009 |
| WO | WO-2009/090499 A2 | 7/2009 |
| WO | WO 2009/090499 A2 | 7/2009 |
| WO | WO-2009/143255 A1 | 11/2009 |
| WO | WO 2009/143255 A1 | 11/2009 |
| WO | WO-2010/043533 A1 | 4/2010 |
| WO | WO 2010/043533 A1 | 4/2010 |
| WO | WO2010/097116 A1 | 9/2010 |
| WO | WO 2010/136076 A1 | 12/2010 |
| WO | WO-2010/136076 A1 | 12/2010 |
| WO | WO 2010/136078 A1 | 12/2010 |
| WO | WO-2010/136078 A1 | 12/2010 |
| WO | WO 2010/139635 A1 | 12/2010 |
| WO | WO-2010/139635 A1 | 12/2010 |
| WO | WO 2010/139793 A1 | 12/2010 |
| WO | WO-2010/139793 A1 | 12/2010 |
| WO | WO-2010/147553 A1 | 12/2010 |
| WO | WO 2010/147553 A1 | 12/2010 |
| WO | WO-2011/032960 A1 | 3/2011 |
| WO | WO 2011/032960 A1 | 3/2011 |
| WO | WO-2011/051366 A2 | 5/2011 |
| WO | WO 2011/051366 A2 | 5/2011 |
| WO | WO 2011/141907 A1 | 11/2011 |
| WO | WO-2011/141907 A1 | 11/2011 |
| WO | WO 2012/064258 A1 | 5/2012 |
| WO | WO-2012/064258 A1 | 5/2012 |
| WO | WO 2012/145685 A1 | 10/2012 |
| WO | WO 2012/164397 A1 | 12/2012 |
| WO | WO 2013/006119 A1 | 1/2013 |
| WO | WO 2013/085454 A1 | 6/2013 |
| WO | WO 2014/154498 A1 | 10/2014 |

OTHER PUBLICATIONS

International Search Report PCT/EP2013/065939 dated Nov. 18, 2013.
International Search Report PCT/EP2013/065934 dated Nov. 22, 2013.
International Search Report PCT/EP2013/065938 dated Nov. 29, 2013.
International Search Report PCT/IB2012/001231 dated Nov. 15, 2012.
International Search Report PCT/IB2012/001705 dated Dec. 4, 2012.
International Search Report PCT/IB2012/001150 dated Dec. 7, 2012.
International Search Report PCT/IB2012/001172 dated Dec. 7, 2012.
International Search Report PCT/IB2012/001394 dated Dec. 7, 2012.
International Search Report PCT/IB2012/001426 dated Dec. 7, 2012.
International Search Report PCT/IB2012/001507 dated Feb. 4, 2013.
International Search Report PCT/IB2012/002105 dated Feb. 4, 2013.
International Search Report PCT/IB2012/001147 dated Feb. 11, 2013.
International Search Report/Written Opinion PCT/IB2012/001231 dated Nov. 15, 2012.
International Search Report/Written Opinion PCT/IB2012/001705 dated Dec. 4, 2012.
International Search Report/Written Opinion PCT/IB2012/001150 dated Dec. 7, 2012.

(56) References Cited

OTHER PUBLICATIONS

International Search Report/Written Opinion PCT/IB2012/001172 dated Dec. 7, 2012.
International Search Report/Written Opinion PCT/IB2012/001394 dated Dec. 7, 2012.
International Search Report/Written Opinion PCT/IB2012/001426 dated Dec. 7, 2012.
International Search Report/Written Opinion PCT/IB2012/001507 dated Feb. 4, 2013.
International Search Report/Written Opinion PCT/IB2012/002105 dated Feb. 4, 2013.
International Search Report/Written Opinion PCT/IB2012/001147 dated Feb. 11, 2013.
International Search Report/Written Opinion PCT/EP2013/065940 dated Nov. 4, 2013.
International Search Report/Written Opinion PCT/EP2013/065939 dated Nov. 18, 2013.
International Search Report/Written Opinion PCT/EP2013/065934 dated Nov. 22, 2013.
International Search Report/Written Opinion PCT/EP2013/065938 dated Nov. 29, 2013.
International Search Report/Written Opinion PCT/EP2015/051253 dated Jul. 15, 2015.
International Search Report/Written Opinion PCT/EP2015/051257 dated Mar. 23, 2015.
International Search Report/Written Opinion PCT/EP2015/051258 dated Sep. 15, 2015.
OHIM Design Registration Registered May 19, 2011, Reg. No. 001277941-001.

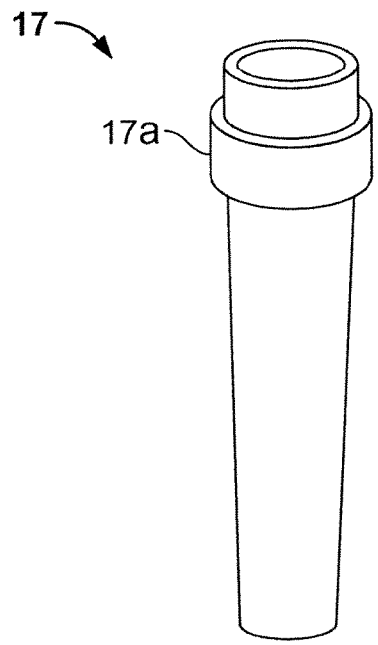
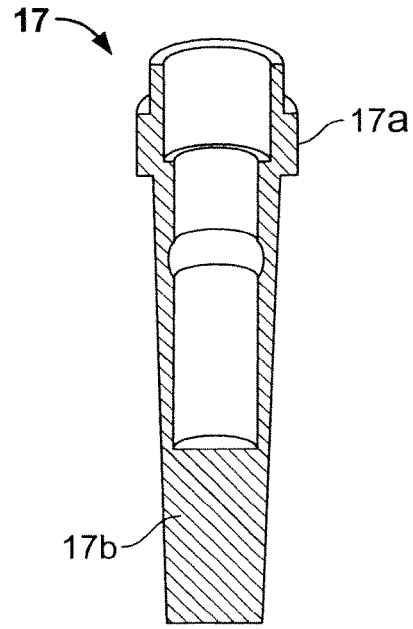
FIG. 6A　　　　　　FIG. 6B
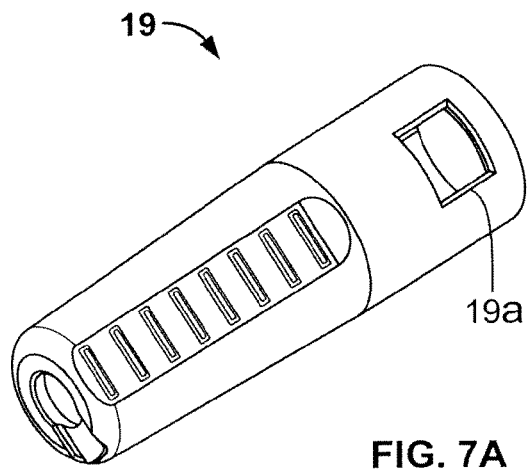
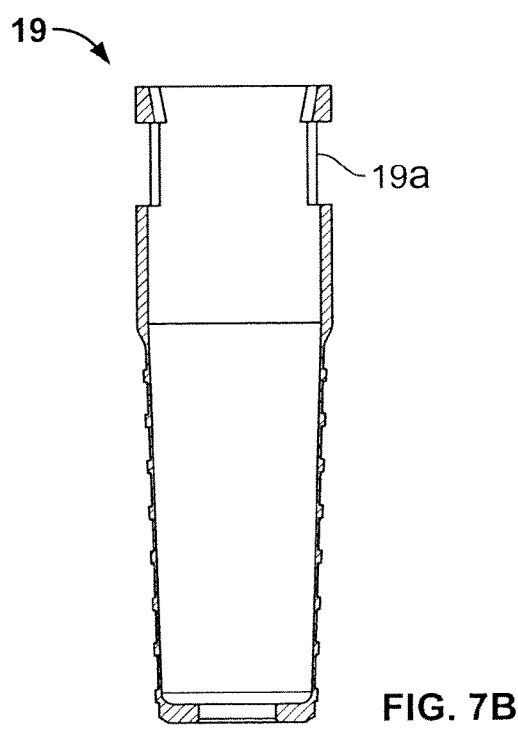
FIG. 7A　　　　　　FIG. 7B

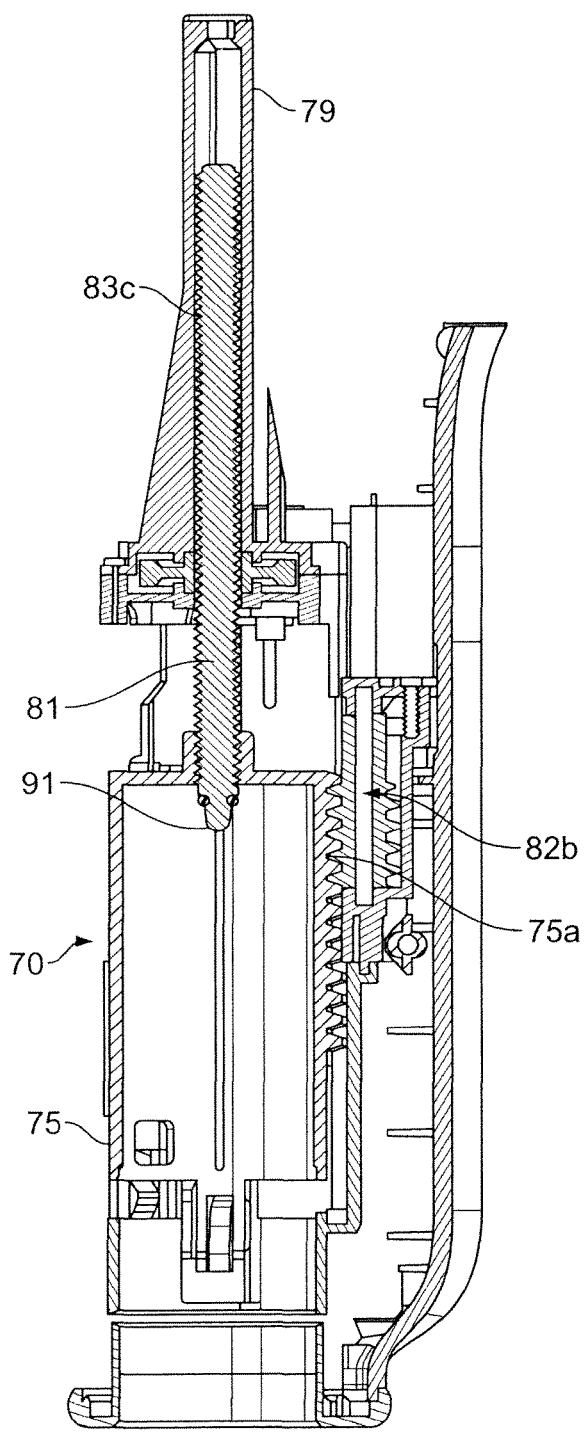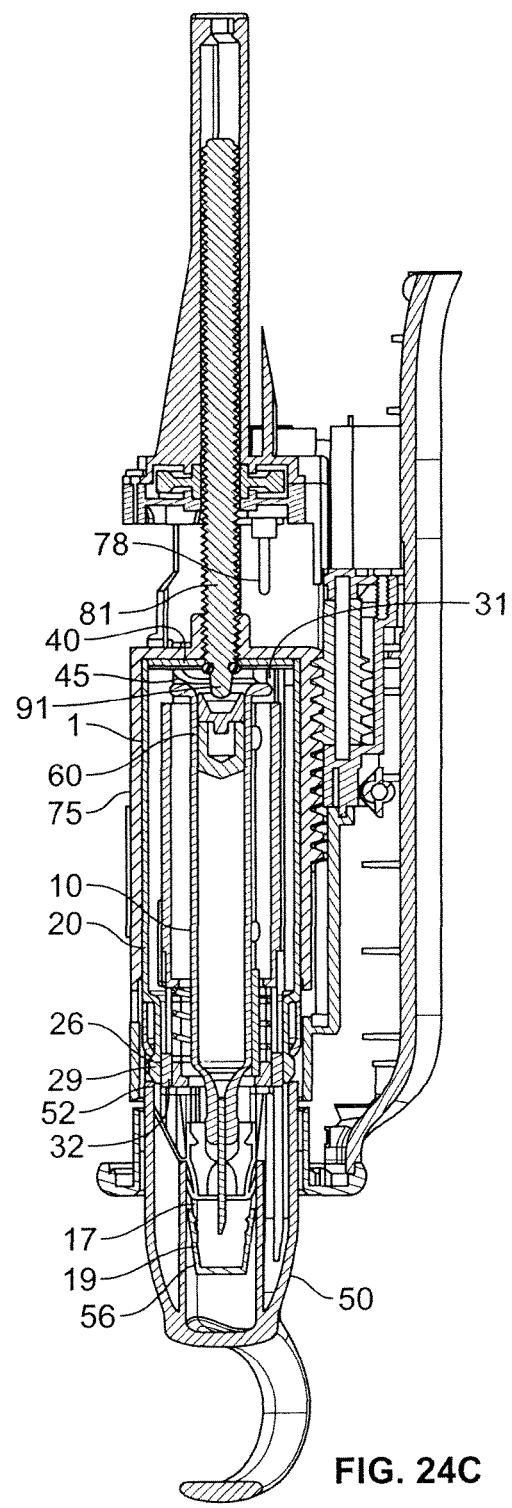
FIG. 24B
FIG. 24C

AUTO-INJECTOR

CROSS-REFERENCE TO RELATED APPLICATIONS

This application is a United States National Stage filing under 35 U.S.C. 371 of International Application No. PCT/EP2013/065939, filed Jul. 29, 2013, which claims priority to British Application GB1213502.6, filed Jul. 30, 2012, and British Application GB1222353.3, filed Dec. 12, 2012, each of which is hereby incorporated by reference herein in its entirety. International Application No. PCT/EP2013/065939 was published under PCT Article 21(2) in English.

BACKGROUND

The present application relates to an auto-injector device for receipt of a syringe that is suitable for use in the injected delivery of a drug formulation to a patient.

It is well-known to use syringes for the delivery of injectable liquid drug formulation to a patient. Syringes rely on puncturing of the patient's skin by a hollow needle through which the injectable liquid drug (e.g. in solution or suspension form) is delivered to the muscle or tissue of the patient. Typically, syringes comprise a barrel for containing a volume of the liquid drug; a hollow needle defining a needle tip for dispensing of the liquid; and a plunger that is axially movable within the barrel.

It is also well-known to provide auto-injectors for use with syringes. Such auto-injectors typically comprise a body for housing the syringe and an actuating mechanism, which is triggered in use, to allow for automatic delivery of the liquid drug formulation from the syringe. Actuating mechanisms typically comprise a source of drive (e.g. a strong spring) for drivable movement of a drive transfer element (e.g. a plunger rod) that transfers drive to the plunger for axial movement thereof within the syringe barrel. Such movement of the plunger results in the plunged driving of the liquid drug from the syringe barrel to the hollow needle for dispensing to the patient via the needle tip thereof.

For safety and hygiene reasons, it is desirable that the hollow needle does not protrude from the housing of the auto-injector other than when expelling the liquid drug formulation during an injection procedure. Thus, auto-injectors have been developed in which, the housing is arranged such that a needle receiving part allows for the needle of the syringe to be axially moveable therein from a first (i.e. rest) position in which the hollow needle is shrouded by the needle receiving part to a second (i.e. use) position in which at least the tip of the needle protrudes from that needle receiving part of the housing for penetrating the skin of the patient to an injection position. Only when the needle is at such injection position should it be possible for drug delivery to commence. Thus, auto-injectors have been developed which provide a two stage actuating mechanism, which first acts to transfer drive force to move the syringe from the 'rest' to the 'use' position, and which only then secondly acts to transfer drive force to the plunger for expelling of liquid drug contents from the syringe barrel.

The majority of auto-injectors are configured as a single device that incorporates both syringe and actuating mechanism in the same device housing. It is common for such devices to be arranged to be disposable such that following injected delivery of the liquid drug formulation, and typically also following retraction of the syringe back into the housing, the whole device may be safely disposed of.

SUMMARY

It has been proposed to configure auto-injectors to include an electrically powered source of drive. Such configurations are particularly suitable for use by patients whose manual dexterity is so compromised (e.g. due to severe arthritis) that electrical powering is of real practical assistance. The use of electrically powered drive systems can also allow for more complex drive arrangements (e.g. two speed injection procedures) to be engineered. Furthermore, electrical powered devices can also be arranged to include electrical control systems and electronic data management systems including those that provide information and feedback to the patient by means of a suitable user interface.

In some situations, it is undesirable for an electrically powered auto-injector to be fully disposable. Auto-injectors disclosed herein, in certain embodiments, include both a re-useable drive unit comprising an electrically powered source of axial drive and a cassette unit comprising a syringe, which releasably interfits with the drive unit and can be arranged to be disposable. The housing of the drive unit defines a docking cavity arranged for docking receipt of the cassette unit at a docking position. Such auto-injectors may be 'environmentally friendly,' where the majority of components are retained to be used for further injection procedures. It also allows for the drive unit to be fitted with additional features such as electronics, which may not be cost effective on a completely disposable device.

The cassette unit comprises a cassette unit housing defining a cassette unit housing cavity and a needle projection aperture. The cassette unit housing cavity is arranged for receipt of a standard syringe comprising a barrel for containing a volume of a liquid drug formulation, a hollow needle at a front end of said barrel defining a needle tip for dispensing of the liquid drug formulation and a plunger that is axially movable within the barrel. Either the syringe or the cassette unit and syringe held thereby is movable within the drive unit housing from a rest position, in which the needle tip of the syringe is within the drive unit housing to a use position, in which the needle tip protrudes from a needle delivery aperture of the drive unit housing. In embodiments, the cassette unit is also provided with a removable cap that fits over and thereby, acts such as to close off, the needle projection aperture. In embodiments, connecting to the removable cap, there is also provided a needle cover defining a needle sheath arranged in a sheathing configuration for sheathing of said needle tip.

The drive unit includes a drive arrangement comprising an electrically powered source of axial drive. In certain implementations, the drive unit includes a first drive transfer element for transferring the axial drive to the cassette unit for advancing the syringe to said use position, and a second drive transfer element for subsequently transferring the axial drive to the plunger of the syringe for moving the plunger into the barrel of the syringe to eject at least part of the volume of liquid drug formulation.

The cassette unit may be provided with a cassette unit end cap that is in capping relationship with a rearward entrance thereof. The cassette unit end-cap may be arranged to define a drive rod-receiving opening for receipt of a second drive transfer element in the form of a drive rod for providing forward axial drive to the plunger of the syringe.

One possible problem with such cassette units is to prevent unintended movement of the syringe relative to the cassette unit (e.g. rattling about of the syringe within the cassette unit) such as may arise during transport thereof.

A further possible problem associated with the use of such an auto-injector having a re-useable drive unit and a separate cassette unit is that of accommodating different syringe sizes within a common (i.e. the same) cassette unit geometry. Often encountered sizes of syringe include the 2.25 ml syringe and the 1 ml 'long' syringe, which has a smaller syringe barrel diameter. Thus, the accommodation of syringes of both different length and barrel girth is desirable.

In solution to one or both of the above problems, the cassette unit herein is provided with a biasing element (e.g. a spring) defining a biasing relationship (e.g. a sprung biasing relationship) between the cassette unit end-cap and the flange of the syringe, thereby urging the syringe forwards in relation to the cassette unit end cap and so reducing unintended movement thereof.

The accommodation of multiple syringe sizes within the same cassette unit geometry is achievable by selecting a spring form that is tailored both to the particular sizing of the barrel of each different syringe and to the geometry of the common cassette unit. In embodiments, the spring may be selected such as to effectively (i) to increase the effective length of the syringe; and/or (ii) to provide a degree of stability to the proximal end of the assembly.

In embodiments, the spring may take any suitable form including tension and torsion springs, but also may be comprised of materials that provide natural spring or biasing properties (e.g. sponge). In embodiments, the spring is either provided as a separate component to the cassette unit end-cap or integrally with the cassette unit end-cap.

In embodiments, the cassette unit is also provided with a sleeve form adapter arranged for receipt by the syringe barrel and to fit at least partly over the syringe barrel. Thus, the accommodation of multiple syringe sizes within the same cassette unit geometry is further achievable by selecting a sleeve form adapter tailored both to the particular sizing of the barrel of each different syringe and to the geometry of the common cassette unit. In embodiments, the sleeve form adapter acts such as to (i) increase the effective diameter of the syringe barrel; and/or (ii) to provide reinforcement to the syringe; and/or (iii) to increase the effective length of the syringe.

The sleeve form adapter may also be provided with one or more shoulder support features for supporting the forward shoulder of the syringe. In use, the one or more shoulder support features act to direct a major part of an applied load (e.g. drive) path to travel through the shoulder at the forward end of the syringe and lesser load to pass through the flange at the rear end of the syringe. Any risk of damage to the syringe during an injection operation is thereby reduced.

According to one aspect there is provided a cassette unit for use with an auto-injector having an electrically powered drive unit, said cassette unit comprising:
  a cassette unit housing defining a cassette unit housing cavity, a rearward entrance to said cavity and a forward needle projection aperture;
  said cassette unit housing cavity arranged for receipt of a syringe comprising:
    a barrel for containing a volume of a liquid drug formulation, said barrel defining a flange at the rear end thereof and a forward shoulder at the forward end thereof;
    a hollow needle at a front end of said barrel, said hollow needle defining a needle tip for dispensing of said liquid drug formulation; and
    a plunger that is axially movable within the barrel; and
  in capping relationship with said rearward entrance of the cassette unit housing, a cassette unit end-cap, said cassette unit end-cap defining a drive rod-receiving opening for receipt of a drive rod for providing forward axial drive to said plunger; and
    a biasing element defining a biasing relationship between the cassette unit end-cap and the flange of the syringe, thereby urging the syringe forwards in relation to the cassette unit end cap.

According to another aspect there is provided an auto-injector comprising
  (a) a cassette unit as described herein; and
  (b) a drive unit.

In certain implementations, the drive unit includes a housing defining a docking cavity and a needle delivery aperture, wherein said docking cavity is arranged for docking receipt of said cassette unit at a docking position. The cassette unit and/or said syringe is movable from a rest position, in which the needle tip of the syringe is within the drive unit housing to a use position, in which the needle tip protrudes from said needle delivery aperture.

The auto-injector may also include a drive arrangement comprising
  one or more electrically powered sources of axial drive;
  a first drive transfer element for transferring said axial drive to the cassette unit and/or to the syringe for advancing the syringe to said use position; and
  a second drive transfer element for subsequently transferring the axial drive to the plunger slaving part and hence, to the plunger of the syringe for moving the plunger into the barrel of the syringe to eject at least part of said volume of liquid drug formulation.

According to another aspect, there is provided a cassette unit comprising a housing defining a housing cavity arranged for receipt of a syringe; a cassette unit end-cap defining a drive rod-receiving opening for receipt of a drive rod for providing forward axial drive to a plunger provided within the syringe; and a biasing element defining a biasing relationship between the cassette unit end-cap and a flange of the syringe, for urging the syringe forwards in relation to the cassette unit end-cap. In certain implementations, said drive rod-receiving opening is defined by a periphery, said periphery is provided with a forward skirt and said biasing element is arranged for receipt about said forward skirt. In certain implementations, the biasing element may be provided as a separate component to the cassette unit end-cap, or the biasing element may be provided integrally with the cassette unit end-cap. In certain implementations, the biasing element is configured to abut a forward end of the cassette unit end-cap and to abut the flange of the syringe so as to define a sprung biasing relationship between said end-cap and said flange.

According to another aspect, there is provided a cassette unit comprising a housing defining a housing cavity arranged for receipt of a syringe; means for providing forward axial drive to a plunger provided within the syringe; and means for biasing the forward axial drive means and a flange of the syringe, for urging the syringe forwards in relation to the forward axial drive means.

These and other embodiments are set forth in the later description, which describes for illustrative purposes only various embodiments thereof.

In relation to aspects of the auto-injector device described herein the term 'forward' is used to mean that end of the device, which locates closest to the injection site in use (i.e.

the needle tip end) and the term 'rear' or 'rearward' is used to mean that end of the device, which locates furthest from the injection site in use.

There is provided an auto-injector device that is arranged for use with a syringe that contains a liquid drug formulation. The syringe is arranged to be suitable for use in the injected delivery of the liquid drug formulation to a patient.

The auto-injector comprises both a drive unit and a cassette unit receivable by the drive unit. The individual drive unit and cassette unit parts thereof comprise further separate aspects of the present application. In embodiments the drive unit and cassette unit are provided as a kit of parts.

Auto-injectors comprising both a drive unit comprising an electrically powered source of axial drive and a cassette unit comprising a syringe, which releasably interfits with the drive unit already have been described in Applicant's PCT publications WO2012/164,390; WO2012/164,402; WO2012/164,404; WO2012/164,389; WO2012/164,397; WO2012/164,394; WO2013/001378; WO2012/164,406; and WO2012/164,403, the contents of all of which are incorporated by reference in their entirety and made part of this application.

Cassette Unit

The cassette unit comprises a cassette unit housing defining a cassette unit housing cavity. The cassette unit housing cavity is arranged for receipt of a syringe and is therefore typically sized and shaped for this purpose. The cassette unit housing may be arranged as a single part or a multi-part (e.g. two part) cassette unit housing assembly.

In embodiments, the syringe is held in generally fixed fashion within the cassette unit housing. In other embodiments, the syringe is movable within the cassette unit housing such as in a direction parallel with or along the drive axis.

In embodiments, wherein the syringe is held in generally fixed fashion within the cassette unit housing, at least the needle tip of the syringe normally protrudes out of the cassette unit housing cavity such as from a needle projection aperture thereof.

In other embodiments, the syringe is movable within the cassette unit housing from a first position, in which the needle tip of the syringe is within the cassette unit housing to a second position, in which at least the needle tip protrudes from a needle projection aperture thereof. The syringe that is receivable within the cassette unit housing cavity comprises a syringe barrel for holding a volume of the liquid drug formulation; a hollow needle at a front end of the barrel, the hollow needle defining a needle tip for dispensing of said liquid drug formulation; and a plunger (e.g. in the form of a rubber stopper) that is axially movable within the syringe barrel. The syringe plunger is movable axially within the barrel so as to enable the liquid drug formulation to be expelled from the barrel and thence through the hollow needle via the dispensing tip for injection into the patient. The syringe barrel is typically, comprised of glass but may also be comprised of a relatively hard plastic polymer such as hardened polyethylene, polycarbonate or cyclic olefin polymers.

In embodiments, the plunger is comprised of a natural or synthetic polymer friction material, which frictionally interacts with the side wall of the syringe barrel. Suitable plunger materials include natural or synthetic rubbers or elastomeric materials.

In more detail, the syringe barrel is selected such as to define a barrel chamber for containing a suitable volume of the liquid drug formulation. In embodiments, that suitable volume is selected to correspond to a single dose of the drug formulation to be delivered to the patient. In other words, delivery of that single dose involves expelling all of the liquid drug formulation contents of the barrel chamber through the hollow needle for injection into the patient.

In embodiments, the rear end of the syringe barrel is provided with an end flange. In embodiments, the forward end of the syringe barrel is shaped to provide a shoulder. In embodiments, forward of that shoulder the syringe narrows further into a neck, which typically forms the needle-holding part thereof.

In embodiments, the needle barrel is provided with a barrel sleeve that is arranged to fit over part or all of the length of the needle barrel. The barrel sleeve may also extend out beyond the syringe barrel to wholly or partly enclose a length of the forward shoulder of the syringe barrel and of the hollow needle that extends from (the forward shoulder) of the syringe barrel. In embodiments, the cassette unit is arranged to accommodate multiple syringe sizes. Common sizes of syringe include the 2.25 ml syringe and the 1 ml 'long' syringe, which has a smaller syringe barrel diameter.

In embodiments, accommodation of multiple syringe sizes within the same cassette unit geometry is achievable by providing suitable adapters to the barrel of the syringe. In embodiments, sleeve form adapters are employed.

In embodiments, the sleeve form adapter is arranged for receipt by the syringe barrel and fits at least partly over the flange of the rear end of the syringe barrel. In embodiments, the sleeve adapter is arranged for snap fitting over the end flange of the syringe. In embodiments, the flange is effectively capped by the relevant 'end flange' part of the sleeve form adapter.

In embodiments, a major portion of the syringe barrel and end flange thereof is in use, sleeved by the sleeve form adapter. The overall effect of this sleeving of a major portion is firstly to increase the effective diameter of the syringe barrel; secondly to provide strengthening reinforcement to the end flange; and thirdly to increase the effective length of the syringe.

In one particular embodiment, the cassette unit is shaped and sized based on the geometry of the larger 2.25 ml syringe. A syringe having a smaller outer dimension (e.g. a 1 ml 'long' syringe) may then be accommodated in this same cassette unit by use of a sleeve adapter that effectively functions to adapt the outer syringe geometry (e.g. the outer diameter thereof) to closely correspond to or to be identical with that of the 2.25 ml syringe.

In embodiments, adding a sleeve adapter to the smaller diameter 1 ml 'long' syringe can make it slightly longer than the 2.25 ml syringe. In embodiments, when the cassette unit is assembled with the 2.25 ml syringe, an adapter ring may be added underneath the syringe flange to make its effective flange thickness the same as that of a smaller 1 ml syringe with a sleeve adapter.

In embodiments, the sleeve adapter is provided with one or more slits in the wall(s) of the sleeve adapter such as to define flexible fingers, which allow the adapter to flex open. In embodiments, the presence of such flexible fingers is of utility during assembly of the sleeved syringe as the needle cover (e.g. rigid needle shield), which typically has a larger diameter than the syringe barrel, passes through the centre of it when the syringe is pressed into the adapter. In embodiments, the end flange at the rear end of the syringe then snaps into the rear end of the adapter such that the syringe is locked into the adapter once assembled.

In embodiments, one or more positioning and/or retaining features are provided to the cassette unit housing for positioning and/or retaining the syringe and sleeve form adapter in the cassette unit housing cavity. In embodiments, the one or more positioning and/or retaining features comprise one or more snap features provided interiorly to the cassette unit housing.

In certain implementations, the ability of the cassette unit to accommodate syringes of different sizes confers certain advantages. In the case of drive units with a variable performance across the injection stroke it may be advantageous in some circumstances to use a syringe of larger bore diameter because the same volume of drug can be delivered from a shorter injection stroke, thereby enabling the drive unit performance to be optimized.

Similarly, for a given combination of needle and drug (same needle bore and viscosity) the volume injected per unit displacement of the plunger is greater in the case of a wider bore syringe by a factor proportional to the square of the difference in syringe diameter. A faster injection can therefore be achieved for the same plunger displacement velocity. In this case the force applied by the plunger will be greater in the larger syringe due to the increase in volumetric flow rate. This may be useful in cases where the maximum displacement velocity is limiting.

Also, the flexibility in dose delivery rate provided by variable syringe sizes may also be beneficial in optimizing the power requirements of the electrically powered drive unit. Thus, in embodiments this may limit peak current drain of the batteries thereby enabling smaller batteries to be used, maximizing the time between recharge or replacement and/or prolonging their useful life.

It has been appreciated that to reduce the risk of the syringe shattering under the loads associated with injecting the drug, it is important for a majority of the load path to travel through the shoulder at the forward end of the syringe and lesser load to pass through the flange at the rear end of the syringe.

In embodiments, the forward shoulder of the syringe is provided with one or more shoulder support features. In embodiments, the one or more shoulder support features are integral (e.g. integrally formed) with the cassette unit housing. In other embodiments, the one or more shoulder support features are defined by one or more separate shoulder support parts provided to the cassette unit.

In embodiments, the one or more shoulder support features locate (e.g. in snap-fit arrangement) between the needle cover (e.g. rigid needle shield) and the forward shoulder of the syringe. In embodiments, the sleeve adapter as described above, is provided with such one or more shoulder support features that in embodiments, snap-fit between the needle cover (e.g. rigid needle shield) and the forward shoulder of the syringe. This snap fitting is typically enabled after the syringe assembly has been pressed through the sleeve adapter during the assembly operation.

In embodiments, a clearance space is defined between the bottom of the syringe flange and the closest surface of the sleeve adapter. In embodiments, the sleeve form adapter acts to space the end flange of the syringe from the inner walls of the cassette unit housing. In embodiments, when the syringe is loaded within the cassette unit housing the flange of the syringe is spaced from the inner walls of the cassette unit housing and/or the sleeve adapter and in embodiments, is not in contact with anything.

In embodiments, a ring of (e.g. compliant such as resilient or flexible) material such as rubber or a suitable synthetic polymeric material is employed to bear some of the load on the flange and/or to accommodate tolerances. In embodiments, that ring of material is arranged for receipt over the shoulder support feature. In embodiments, the ring of material acts such as to secure the shoulder support feature in place such as by securing a snap-fit arrangement in place.

In embodiments, at least part of the syringe or syringe/sleeve adapter combination interacts with (e.g. inserts into) a constraining feature of the cassette unit housing that has a tight clearance between its inner walls and the outside diameter of the standard (e.g. 2.25 ml) syringe. In embodiments, this constraining feature of the cassette unit housing interacts with the shoulder and/or neck of the syringe. In embodiments, this feature is the only surface acting to constrain the position of the syringe within the cassette unit housing (e.g. during injection). In embodiments, the constraining feature of the cassette unit housing that constrains the syringe also prevents the sleeve adapter from flexing outwards when the injection loads are applied to the syringe. With the rear end of the sleeve adapter (e.g. any defined fingers thereof) securely snapped under the shoulder of the syringe and so prevented from flexing outwards, the syringe is effectively secured within the cassette unit housing. In embodiments, if this were not the case the force applied to the syringe during injection could push the fingers open and enable the syringe to push through.

The hollow needle defines a needle bore, which is most typically of circular cross-section and of selected bore diameter. It may be appreciated that in embodiments, the bore diameter may affect the force required to expel the liquid drug formulation through the needle and also the velocity at which the liquid drug formulation is expelled.

The selected needle bore may also, in embodiments affect the degree of patient discomfort during injection. Smaller bore diameters, typically provide more patient comfort, whereas larger bore diameters enable more rapid/lower force delivery of the liquid through the needle. A compromise is therefore needed in selecting a needle bore to provide acceptable patient comfort and liquid delivery through the needle characteristics.

Examples of typical needles that are suitable for use therein include 12.5 mm ("half inch") long thin wall needles of grade 23 G, 25 G or 27 G. These have a needle bore of from about 0.2 to 0.4 mm such as from 0.25 to 0.35 mm. Other examples include both regular and thin wall needles used in conventional syringes including those with bevels such as 3 and 5 bevels.

The cassette unit housing and any inner cassette unit housing sub assembly thereof is shaped to define a cassette unit housing cavity within which the syringe is receivable, and in embodiments, a needle projection aperture. The cassette unit housing cavity is typically cylindrical in form, thereby matching the typically cylindrical outer profile of a syringe. The cassette unit housing cavity may be further shaped with any manner of grooves, indentations or other shaping or surface details to define a 'lock and key' relationship between the cassette unit housing and any inner cassette unit housing sub assembly thereof and the syringe. Colour guides, arrows and any other surface markings may also be employed.

Typically, the cassette unit housing and/or any inner cassette unit housing sub assembly thereof is provided with a barrel receiving part for receiving the barrel of the syringe; a plunger receiving part for receiving the plunger of the syringe; and in embodiments, a needle receiving part for receiving the hollow needle of the syringe.

In embodiments, the plunger receiving part of the cassette unit housing and/or any inner cassette unit housing sub assembly thereof allows the plunger within the syringe barrel to be received thereby and for the plunger to be movable (e.g. axially) therein from a first position to a second position, in which it is moved somewhat into the syringe barrel. During use the plunger is in embodiments, movable to a fully plunged position in which most, in embodiments all of the liquid drug formulation contents of the barrel have been expelled.

In embodiments, the needle receiving part of the cassette unit housing and/or any inner cassette unit housing sub assembly thereof includes a needle projection aperture through which the hollow needle may protrude from the housing, for example during expelling of the liquid drug formulation through the hollow needle and its needle tip for delivery to the patient.

In embodiments, the syringe is movable within the cassette unit housing cavity from a rest position, in which the needle tip is within the cassette unit housing to a use position, in which the needle tip protrudes from the needle projection aperture. In other embodiments, the syringe is in fixed relationship with the cassette housing in which, typically the needle tip protrudes from the needle projection aperture.

Where the syringe is movable in the cassette unit housing, it may desirable for safety and hygiene reasons that the needle does not protrude from (i.e. out with) the cassette unit housing other than when expelling the liquid drug formulation during an injection procedure. Thus, the cassette unit housing and/or any inner cassette unit housing sub assembly thereof and cassette unit housing cavity defined thereby is generally arranged such that the needle receiving part thereof allows for the needle of the syringe to be axially moveable therein from a first position in which the needle is wholly housed (or shrouded) by the needle receiving part to a second position in which at least the tip of the needle protrudes from that needle receiving part of the cassette unit housing.

In embodiments, where the syringe is movable within the cassette unit the cassette unit housing includes biasing means (e.g. a spring) arranged such that the needle is normally biased towards the first position, wherein such biasing means are overcome during the actuation of the syringe (e.g. by an actuating mechanism) to allow for movement of the needle to the second position.

In embodiments, it is desirable for cassette unit housing to allow for the needle of the syringe to be retracted into the housing after use. Thus, it is desirable to be able to retract the needle back into the needle receiving part of the cassette unit housing after the injection procedure, that is to say to retract the needle from the second position to a retracted position that may in embodiments, correspond to the first position or in other embodiments, correspond to a third position, which in embodiments is further away from the needle projection aperture. A needle retract mechanism may thus, be provided to the cassette unit housing (e.g. responsive to a biasing means such as a light return spring) to retract the syringe needle back into the cassette unit housing.

In embodiments, it is desirable for the cassette unit housing to allow for the needle of the syringe to be shrouded by a needle shroud element after use. Thus, in particular it is desirable to be able to provide a means of shrouding the needle of the syringe that is moved or otherwise brought into operation after completion of the injection procedure. Such means in embodiments comprises a movable shroud element that is adapted to be movable to a shrouding configuration at the end of the injection procedure.

In embodiments, the cassette unit housing is provided with a removable cap that fits over and thereby, acts such as to close off, the needle projection aperture. It may therefore, be appreciated that when in the capped position, the removable cap acts such as to prevent ingress of contaminants into the needle receiving part of the housing.

In embodiments, the syringe further comprises a needle cover defining a needle sheath arranged in a sheathing configuration for sheathing (e.g. sealing) of the needle tip.

In embodiments, the needle sheath is comprised of a (e.g. resiliently) compressible material such as a natural or synthetic rubber material. In a storage configuration, the needle tip sticks into (e.g. is spiked or staked into) the needle sheath such that sealing of the needle tip is achieved. Usually, at least the first 3 to 4 mm of the needle tip end is so sheathed. It will be appreciated that for clinical reasons, the sealing of the needle tip acts in embodiments, such as to prevent passage of contaminant, bacterial or otherwise, through the needle tip and thus into the needle bore and syringe barrel chamber. Sterile sealing is preferred.

In embodiments, the needle cover is provided with a needle sheath cover for covering the needle sheath thereof. In embodiments, the needle sheath cover is comprised of a rigid material (e.g. polypropylene). In embodiments, the needle sheath cover is provided with one or more gripping elements (e.g. hooks) arranged for gripping of the needle sheath. In embodiments, the needle sheath is provided with one or more features arranged for receipt of the one or more gripping elements such as one or more indents, grooves or cavities.

In embodiments, the needle cover is provided to (e.g. fixed to or integral with) a removable cap for the cassette unit housing. Thus, in embodiments, the needle cover projects within the cap such that when the removable cap is in the capped position the needle sheath and any needle sheath cover therefor projects towards the needle tip of the syringe. In such embodiments, when in the capped position, the needle tip is sheathed by the needle sheath, and when the cap is removed the needle sheath and any needle sheath cover therefor are also removed such as to thereby, unsheathe the needle tip. In embodiments, the removable cap defines an essentially closed cylindrical cap chamber, optionally tapering, and the needle sheath and any needle sheath cover are provided along the axis of that cylindrical chamber.

In embodiments, the interior of the removable cap is provided with a connector defining one or more needle cover gripping elements for gripping the needle cover (i.e. gripping the needle sheath and/or any needle sheath cover therefor). In embodiments, such gripping elements are arranged for gripping of the needle cover when in the capping position. In embodiments such gripping elements are (e.g. additionally) arranged for gripping of the needle cover on removal of the cap such that removal of the cap also results in removal of the needle cover and hence, unsheathing of the needle tip. In embodiments, the needle cover gripping elements are arranged to project away from the top inner surface (e.g. of the cylindrical cap chamber) of the removable cap and towards its open end.

In embodiments, the connector comprises one or more needle cover gripping elements (e.g. gripping legs) attaching to a central hub. In embodiments, the connector is in the form of a cage-like needle cover gripper. In embodiments, each gripping element (e.g. leg) is provided (e.g. at the foot thereof) with one or more gripping protrusions such as one or more internally facing hooks or barbs. In embodiments, the internally facing hooks or barbs are disposed at an angle with respect to the gripping leg. In embodiments, the connector locates within the removable cap such that the central hub locates adjacent to or slightly spaced from the top inner cap wall or surface and the gripping legs project away from the top inner cap wall or surface and towards the open end of the cap. Other needle cover gripper arrangements are disclosed in Applicant's co-pending PCT publication no. WO2009/081103 the entire contents of which are incorporated herein by reference.

In embodiments, the removable cap is provided with a connector. The connector is shaped to fit within and engage the needle cover and to engage the inner part of the removable cap. In embodiments, the connector includes one or more needle gripper elements in the form of first legs attaching to a central hub and spaced symmetrically away from one another, each first leg having one or more internally facing barbs pointing toward a forward region of the connector and adapted to engage a proximal region of the needle cover. In embodiments, the one or more internally facing barbs are disposed at an angle with respect to the first leg. In embodiments, the connector also includes one or more second legs spaced symmetrically away from one another, each second leg having one or more externally facing barbs located in the forward region of the connector and adapted to engage a forward region of the inner part of the removable cap. In embodiments, the one or more first legs are biased initially at about 60 to 80 degrees with respect to the horizontal. Arrangements of removable cap and connector of this type are disclosed in Applicant's co-pending PCT publication no. WO2009/090499 the entire contents of which are incorporated herein by reference.

In embodiments, the geometry of the removable cap is selected to allow for the needle cover to be sufficiently aligned with the needle of the syringe so that on re-capping the needle does not undesirably catch on the needle sheath inside the needle cover. In embodiments, wherein the connector comprises one or more needle cover gripping elements (e.g. gripping legs) attaching to a central hub, Applicant has found that to assist re-sheathing of the needle cover it is desirable to position the connector within the removable cap such that the central hub is in spaced relationship to the top inner cap wall of the removable cap. When so-positioned, the gripping legs project away from the top inner cap wall and towards the open end of the cap. Applicant has found that having the central hub in somewhat spaced relationship to the top inner cap wall allows for a certain 'give' in the axial position of the needle cover such that in the event of any snagging of needle cover by the needle tip during re-sheathing, the connector and/or needle cover is free to move into the 'give' space, thereby ensuring that the snagging event does not result in any bending, or in a worst case scenario snapping, of the needle. The occurrence of any needle stick hazards during re-capping and re-sheathing is thus, minimized. In addition, the presence of 'give' space ensures that it is possible to refit the cap, which may otherwise be prevented by needle snagging.

In embodiments, the removable cap is provided with a spacer insert and the connector is provided to (e.g. locates within) the spacer insert. In these embodiments, the function of the spacer insert is effectively to assist in defining of the 'give' space as described above. In embodiments, the spacer insert defines a central end hub and an inner boss, which extends from the central end hub to define a chamber for receiving the connector and in embodiments also, in use for receiving the needle cover as gripped by the connector. In embodiments, the spacer insert also defines an outer boss, which extends from the end hub and in embodiments, also extends about (e.g. circumferentially about) the inner boss. In embodiments, the outer boss includes crenellated portions therein. In embodiments, the outer boss defines flexible fingers, which splay out from the central end hub and thus, extend about the outer surface (e.g. of the lower part of) the outer boss. In embodiments, the flexible fingers of the outer boss locate within the crenellated portions of the outer boss. In embodiments, the spacer insert is comprised of a plastic (e.g. a plastic polymer) material and thus, may be referred to as a plastic 'outer flower' structure. In embodiments, the chamber of inner boss of the spacer insert is provided with a connector (e.g. a needle cover gripper such as in the form of a cage-like structure) and defining plural gripping elements arranged about a central hub. In embodiments, the connector is comprised of a metal and may thus, be referred to as a metal 'inner flower' structure.

To assist with re-sheathing of the needle cover on re-capping of the cassette unit after an injection procedure, the position of spacer insert and connector held there-within is in embodiments, arranged within the removable cap such that central end hub of the spacer insert is in spaced relationship to the effective end wall of the removable cap. By effective end wall it is meant either the actual end wall of the removable cap or a structure (e.g. ledge-like structure) that functions as a seat for the central end hub of the spacer insert and thus, defines the minimum spaced relationship between that central end hub and the end of the removable cap. Having the central end hub of the spacer insert in somewhat spaced relationship to the effective end wall of the removable cap allows for a certain 'give' in the axial position of the connector and needle cover gripped thereby such that in the event of any snagging of needle cover by the needle tip during re-sheathing, the spacer insert, connector and needle cover are free to move into the 'give' space, thereby ensuring that the snagging event does not result in any bending, or in a worst case scenario snapping, of the needle. The occurrence of any needle stick hazards during re-capping and re-sheathing is thus, minimized.

In embodiments, the removable cap is provided with a finger-grip feature that is sized and shaped for gripping by the finger of a user and to provide a ready means for removing the cap and needle cover attached thereto. In embodiments, the finger-grip feature is shaped to provide a ring (e.g. a gripping ring or ring pull) for ready finger gripping by the user by placing a finger or thumb inside the ring.

In embodiments, the removable cap in a capping position, fits over and thereby, acts such as to close off, the needle projection aperture of the cassette unit housing.

In embodiments, the cassette unit housing is provided with one or more first engagement features arranged for reversibly engaging one or more second engagement features of the removable cap for reversible lock engagement of the removable cap to the cassette unit housing.

In embodiments, the first engagement features of the removable cap and the second engagement features of the cassette unit housing are arranged to have a mutually engaging form selected from the group consisting of latching, peg and socket and snap-fit.

In embodiments, the cassette unit housing is provided at the forward end thereof with one or more axially protruding legs each having a first engagement feature arranged thereon, the one or more legs arranged to extend up into the removable cap when the cap is in the capping position and the one or more second engagement features are defined as sockets of the removable cap.

In embodiments, the one or more legs are arranged in a circumferential arrangement about the forward end of the cassette unit housing and said sockets of the removable cap adopt a corresponding circumferential arrangement.

In embodiments, each of the one or more first engagement features of the one or more legs is in the form of a protruding heel having a shaped tip.

In embodiments, the geometry of the removable cap is selected to allow for the needle cover to be sufficiently aligned with the needle of the syringe so that on re-capping the needle does not undesirably catch on the needle sheath inside the needle cover. In embodiments, the geometry of the first engagement features of the cassette unit housing and/or second engagement features of the removable cap is selected to allow for such ease of re-capping. In embodiments, once the first engagement features of the cassette unit housing begin to engage with the second engagement features of the removable cap it is held concentrically enough to prevent the needle from catching on the needle sheath. This is important to ensure that on re-capping the needle cover is able to fully sheathe the used needle to minimize the occurrence of any needle stick hazards.

In embodiments, the cassette unit is provided with a cap lock (i.e. cap removal prevention) feature for selectively preventing removal of the removable cap. In embodiments, the cap lock feature is movable from a first cap locking position in which it prevents removal of the cap from the cassette unit to a second cap un-locking position in which it no longer prevents such cap removal.

In embodiments, the cassette unit is provided with a shuttle lock control defining one or more blocking elements for selectively blocking movement of said one or more first engagement features of the cassette unit housing relative to the one or more second engagement features of the removable cap.

In embodiments, the shuttle lock control is axially movable relative to the cassette unit housing between:
  (i) a first 'cassette unused' position, in which said one or more blocking elements block movement of the one or more first engagement features relative to the one or more second engagement features, thereby keeping the removable cap in locked relationship to the cassette unit housing;
  (ii) a second 'cassette unlocked' position, in which said one or more blocking elements no longer block movement of the one or more first engagement features relative to the one or more second engagement features, thereby allowing for unlocking of the removable cap from the cassette unit housing and for removal and replacement thereof; and
  (iii) after replacement of the removable cap, a third 'cassette used' position, locating intermediate said first and second positions, in which the one or more blocking elements again block movement of the one or more first engagement features relative to the one or more second engagement features, thereby restoring the locked relationship between the removable cap and the cassette unit housing.

In embodiments, the shuttle lock is biased from the second position to the third position.

In embodiments, in use, on removal of the removable cap the shuttle lock control is in the second position; during use of the cassette for injection the shuttle lock control is biased into the third position; and during replacement of the removable cap the shuttle lock control is in the second position.

In embodiments, the shuttle lock control is further provided with an axial position locator, which defines three distinct axial positions of the shuttle lock control relative to cassette unit housing and corresponding to the first, second and third positions.

In embodiments, the axial position locator comprises one or more axial protrusions each having a follower arranged thereon for receipt within a corresponding axial track of the inner cassette unit housing such as to define an axial track-follower relationship therebetween.

In embodiments, the first and second positions correspond to the opposite extremes of the axial track-follower relationship.

In embodiments, each of the one or more axial protrusions of the axial position locator comprises a first latch element arranged for selective latching relationship with a corresponding second latch element of the inner cassette unit housing.

In embodiments, the first latch element defines an axial latching slot and the second latch element comprises a latching foot selectively receivable thereby and movable therewithin such as to define an axial foot-in-slot relationship therebetween.

In embodiments, in the first position the axial latching slot and latching foot are in non-latching relationship and in the second and third positions the axial latching slot and latching foot are in latching relationship, wherein the second and third positions respectively correspond to opposing slot ends of the axial latching slot.

In embodiments, the cassette unit (e.g. at the shuttle lock control) additionally comprising a non-return feature arranged such that when the first and second latch elements have come into latching relationship return to a non-latching relationship is prevented.

In embodiments, as part of the non-return feature the first latch element defines a forward ramped surface and the second latch element defines a corresponding ramped surface such as to facilitate ramping over each other when coming into latching relationship.

In embodiments, the shuttle lock control is marked with a 'used cassette' flag arranged to be brought into registration with an indicator opening or window of the cassette unit housing at the third 'cassette used' position.

In embodiments, the cap lock (i.e. cap removal prevention) feature selectively prevents removal of the removable cap until either the cassette unit locates at the docking position within the drive unit housing or until a release mechanism is activated. In embodiments, the cap lock feature of the cassette unit is only movable from a cap locking position to a cap non-locking position when the cassette unit locates at the docking position within the drive unit housing. In embodiments, the cap lock feature is in the first position during insertion of the cassette unit into the drive unit and moves to the second position when the cassette unit is in the docking position in the drive unit.

In embodiments, the drive unit includes a cap lock release feature arranged such that on moving of the cassette unit towards the docking position in the drive unit said cap lock release feature interacts with the cap lock feature of the cassette unit to move the cap lock feature to the second cap unlocking position when the cassette unit is at the docking position in the drive unit.

In embodiments, the cassette unit includes a plunger slaving part, which is axially movable within the barrel of the syringe for forward movement into contact with the plunger. In embodiments, the plunger slaving part defines a circumferential wall arranged for frictional sliding relationship with the inner wall of the barrel, a rear drive-receiving face and a front plunger-contacting face.

In injected use, the plunger slaving part is in embodiments, brought into contact with the plunger of the syringe and is axially movable within the barrel. In embodiments, the plunger slaving part arranged such that when a drive load is applied to the rear drive-receiving face to bring the front plunger-contacting face into contact with the plunger the drive load is evenly transmitted to the plunger.

In embodiments, the front plunger-contacting face of plunger slaving part is arranged for engagement with the plunger. In embodiments, the diameter of the plunger slaving part corresponds to the diameter of the plunger.

In embodiments, the plunger is made of a material that is resiliently compressible (e.g. rubber or an organic polymeric material) and the plunger slaving part is made of a less compressible material. In embodiments, the plunger slaving part is made of a rigid material (e.g. a hard plastic polymer material such as poly propylene).

In embodiments, the rear drive-receiving face of the plunger slaving part has a central recess for receipt of a drive transfer element. In embodiments, the central recess is shaped such that the drive transfer element is rotatable therein. In embodiments, the central recess is of conical form. In embodiments, the central recess tapers to a square-cut end or to a neb end.

In embodiments, the slaving part may be configured to perform a second purpose of providing an easy-to-identify visual indicator of the plunger's position within the syringe so that the patient can visually confirm the drug had been fully injected. In this embodiment, the slaving part may also be called a stopper position indicator.

In embodiments, the circumferential wall of the plunger slaving part is provided with one or more slide restrictors that restrict frictional sliding movement thereof in relation to the inner wall of the barrel. In embodiments, the one or more slide restrictors are arranged to increase the resistance thereof to frictional sliding movement.

In embodiments, each of the one or more slide restrictors comprises a flexible vane arranged to flex slightly in response to frictional sliding movement of the plunger slaving part.

In embodiments, the one or more slide restrictors are arranged to increase the initial resistance to forward frictional sliding movement but to impart lesser resistance to said forward frictional sliding movement once movement is underway.

In embodiments, the one or more slide restrictors are arranged to more greatly increase the resistance to a backward frictional sliding movement than to the forward frictional sliding movement.

In embodiments, the one or more slide restrictors are arranged at evenly spaced intervals around the circumferential wall.

In embodiments, the cassette unit housing defines a rearward entrance to the cassette unit housing cavity, additionally comprising in capping relationship with a rearward entrance of the cassette unit housing, a cassette unit end-cap. In embodiments, the cassette unit end-cap defines a drive rod-receiving opening for receipt of a drive rod for providing forward axial drive to said plunger slaving part.

In embodiments, in a pre-use configuration, the plunger slaving part is shaped for releasable engagement with the cassette unit end-cap.

In embodiments, the drive rod-receiving opening is defined by a periphery and the plunger slaving part is shaped for releasable engagement in the pre-use configuration with the periphery.

In embodiments, the drive rod-receiving opening is defined by a peripheral rim and said plunger slaving part is shaped for releasable engagement in the pre-use configuration with the peripheral rim.

In embodiments, the drive rod-receiving opening is defined by a periphery, the periphery is provided with a forward skirt and the plunger slaving part is shaped for releasable engagement in the pre-use configuration with the forward skirt.

In embodiments, the forward skirt is provided with an inner-facing rim and the plunger slaving part is shaped for releasable engagement in the pre-use configuration with the inner-facing rim.

In embodiments, the plunger slaving part defines a circumferential rim for releasable engagement in the pre-use configuration with the cassette unit end-cap.

In embodiments, the plunger slaving part defines a circumferential trough for releasable engagement in the pre-use configuration with the cassette unit end-cap.

In embodiments, the plunger slaving part is releasable from the cassette unit end-cap in response to forward axial drive provided to the rear drive-receiving face thereof.

In embodiments, the end-cap is arranged for snap-fit relationship with the cassette unit housing.

In embodiments, the cassette unit additionally comprises a biasing element (e.g. a spring) defining a biasing relationship (e.g. a sprung biasing relationship) between the cassette unit end-cap and the flange of the syringe, thereby urging the syringe forwards in relation to the cassette unit end cap.

In embodiments, the drive rod-receiving opening of the cassette unit end cap is defined by a periphery, the periphery is provided with a forward skirt and said biasing element (e.g. a spring) is arranged for receipt about the forward skirt.

In embodiments, the biasing element (e.g. a spring) is provided as a separate component to the cassette unit end-cap. In other embodiments, the biasing element (e.g. a spring) is provided integrally with the cassette unit end-cap.

In embodiments, the cassette unit additionally comprises one or more shoulder support features for supporting the forward shoulder of the syringe.

In embodiments, the cassette unit further comprises a needle cover defining a needle sheath for sheathing of the needle tip, wherein the one or more shoulder support features locate between the needle cover and the forward shoulder of the syringe.

In embodiments, the needle cover is provided with a needle sheath cover for covering the needle sheath thereof and the one or more shoulder support features locate between the needle sheath cover and the forward shoulder of the syringe.

In embodiments, the needle sheath cover is comprised of a rigid material.

In embodiments, the one or more shoulder support features are in snap-fit arrangement between the needle cover and the forward shoulder of the syringe.

In embodiments, the one or more shoulder support features are defined by one or more separate shoulder support parts provided to the syringe.

In embodiments, the one or more shoulder support features include a split-cylindrical form arranged for receipt by the barrel of the syringe.

Drive Unit

The auto-injector herein is arranged to allow for actuation (i.e. firing) of the syringe and hence, to allow for injected delivery of drug to a patient. The auto-injector thus, also includes a drive unit for transferring axial drive to the syringe.

The drive unit comprises a drive unit housing defining a docking cavity and a needle delivery aperture. The docking cavity is arranged for docking receipt of the cassette unit at a docking position, whereupon said cassette unit and/or the syringe is movable from a rest position, in which the needle tip of the syringe is within the drive unit housing to a use position, in which the needle tip protrudes from said needle delivery aperture. The docking cavity and receivable part of the cassette unit are correspondingly sized and shaped to facilitate the intended docking relationship. The drive unit housing may be arranged as a single part or a multi-part (e.g. two part) drive unit housing assembly.

The drive arrangement comprises at least one electrically powered source of axial drive. The electrical power may be provided by mains electrical supply or by a battery, which in embodiments may be rechargeable.

Electrical energy may be conserved by a variety of means to enable the auto-injector to operate for longer on a given source of energy, such as a battery. Energy conservation or saving methods have additional advantages in terms of reducing the size requirements of the power source (e.g. battery) and thus the weight and portability of the auto-injector.

Electrical energy saving methods may be employed to reduce power consumption of the drive unit. One such method is to use a clock or timer circuit to switch the power on and off at regular or predetermined intervals. In another method a power management system is employed to selectively switch on/off specific electronic functions, such as visual display units or sensors, in order to power these functions only when they are required to perform a particular sequence of events. Thus different electronic functions may be switched on and off at varying intervals and for varying periods under control of a power management system.

In embodiments, the at least one electrically powered source of axial drive comprises an electrically powered motor. The motor may provide linear or rotary drive, but in general, rotary motors used in combination with suitable gearing arrangements are most suitable. The motor may for example, comprise a DC electric motor, a piezoelectric (PZ) motor, an ultrasonic motor, a solenoid motor or a linear motor. In embodiments, the electronic drive system comprises a DC motor, a PZ motor, a stepper motor or an ultrasonic motor. Embodiments are envisaged in which, plural electrically powered sources of axial drive are employed such as a different drive source (e.g. motor) for each of the first and second drive transfer elements.

The drive arrangement comprises a first drive transfer element for transferring axial drive to the cassette unit and/or the syringe for advancing the syringe to said use position; and a second drive transfer element for subsequently transferring axial drive to the plunger of the syringe for moving the plunger into the barrel of the syringe to eject at least part of the volume of liquid drug formulation.

In embodiments, the first and second drive transfer elements are configured as separate parts. In other embodiments, the first and second drive transfer elements are in coupling relationship (e.g. via one or more coupling elements) or form an integral part of a single (i.e. composite) drive transfer element.

In embodiments, the source of axial drive is configured to selectively confer axial drive to the first and second drive transfer elements. Any manner of gearing and/or coupling arrangements may be employed to achieve this purpose.

In embodiments, the drive arrangement comprises one or more lead screw drive mechanism. In other embodiments, the drive arrangement comprises one or more rack and pinion drive mechanisms. In embodiments, any of such drive mechanisms directly comprise the first and/or second drive transfer elements. In other embodiments, any of such drive mechanisms may be arranged to communicate with the first and/or second drive transfer elements by suitable gearing or coupling arrangements.

In embodiments, the electrically powered source of drive is able to exert an axial drive force of up to 60N via the first and/or second drive transfer elements to the syringe. In embodiments, the force exerted may be arranged to vary over the actuation profile such as from a range of 60 to 40N at the start of actuation to from 40 to 20N at the end of the actuation profile.

In embodiments, release of axial drive force (e.g. actuation of the electrically powered source of drive) is responsive to a trigger (e.g. a user-actuable trigger). In embodiments, the trigger comprises a button, switch or lever arrangement. In other embodiments, a press actuation mechanism that is actuable in response to pressing of the drive unit housing against the skin of a patient is also envisaged. In other embodiments, a skin sensor mechanism is provided to the drive unit housing that is actuable in response to sensing of the skin of the patient.

Axial drive force applied to the first drive transfer element results in drivable movement of the syringe from the rest to the use position. In embodiments, the first drive transfer element communicates directly with (e.g. contacts or abuts) the syringe barrel for transferring drive thereto. In embodiments, the first drive transfer element communicates directly with (e.g. contacts or abuts) the cassette unit for transferring drive thereto, and thus results in drive being transferred to the syringe barrel. In embodiments, the first drive transfer element communicates indirectly with (e.g. via a slaving or coupling element) the syringe barrel and/or the cassette unit for transferring drive thereto.

In embodiments, the first drive transfer element communicates directly or indirectly with a cassette unit holder that holds the cassette unit and syringe thereof within the drive unit such as to transfer drive to the cassette unit holder to thereby result in drivable movement of the syringe from the rest to the use position.

Axial drive force applied to the second drive transfer element (e.g. plunger rod) results in drivable movement of the plunger within the syringe barrel, ultimately to a fully plunged position when most, in embodiments all, of the liquid drug formulation contents of the syringe barrel have been drivably expelled therefrom.

In embodiments, the second drive transfer element communicates directly with (e.g. contacts or abuts) the plunger of the syringe for transferring drive thereto. In embodiments, an end portion of the second drive transfer element directly communicates with (e.g. contacts or abuts) the plunger. In other embodiments, the second drive transfer element communicates indirectly with (e.g. via a slaving or coupling element) the plunger of the syringe for transferring drive thereto. In certain other embodiments, an end portion of the second drive transfer element indirectly communicates with the plunger such as via a washer or other intermediate element.

In embodiments, the first and/or second drive transfer element takes the form of a screw drive element or rod drive element, but other suitable forms are also envisaged.

In embodiments, the drive arrangement includes a first coupling for coupling the first drive transfer element to the cassette unit and/or to syringe barrel of the syringe, wherein said first coupling is a reversible coupling arranged for decoupling when the syringe moves to the use position. Thus, in the initial rest position, application of axial drive force to the first drive transfer element results in movement of the syringe as a whole, but in embodiments, not of the plunger relative to the syringe barrel. It may be appreciated that this preferred initial absence of relative plunger movement is favoured if the frictional forces to be overcome in moving the syringe barrel within the housing are arranged to be much less than for moving the plunger within the syringe barrel. This is typically so since the plunger is often a natural or synthetic rubber element, which frictionally interacts with the sidewall of the syringe barrel. In embodiments, the first coupling is a friction clutch coupling arranged for decoupling by declutching thereof when the syringe moves to the use position.

In embodiments, once the syringe is in the use position (i.e. needle protruding) the first coupling decouples (e.g. demounts) such that no coupling then exists between the first drive transfer element and the syringe barrel. All further axial drive force applied to the second drive transfer element therefore results in plunging axial movement of the plunger within the syringe barrel, which acts to drive the liquid drug formulation contents of the syringe barrel into the hollow needle for injected delivery from the needle tip.

In embodiments, the first and second drive transfer elements are comprised as a single drive shuttle element. In embodiments, the shuttle has an axially symmetric form such as cylindrical form. Guides (e.g. a central aperture of an end wall) may be provided to the shuttle to assist that axial receipt.

In embodiments, a reset mechanism is provided for resetting the drive arrangement after actuation thereof. In embodiments, the reset mechanism is responsive to the electrically powered source of drive.

It is noted that fundamentally any electrically powered source of drive herein converts electrical energy (e.g. stored in batteries) into mechanical motion for movement of the syringe and/or cassette unit and/or the plunger. Electric motors typically use electrical energy to produce rotational motion in the form of a rotating shaft. Various methods are well known for conversion of rotational energy into linear displacement of the plunger. Conceivable methods are a lead screw and worm gear arrangement, cams, a rack and pinion system or a system of rigid linkages using the lever principle. The various methods have certain advantages and disadvantages in terms of complexity, efficiency, mechanical advantage, gearing, maximum displacement velocity, maximum force etc.

Applicant has appreciated that generally for an injection, it is desirable to maintain a constant force over the full displacement stroke of the plunger. The performance in terms of maximum velocity and maximum force of cam and lever based mechanisms will typically vary with position along the injection stroke such that at extremes of the displacement range the maximum force or velocity of the plunger may be substantially different from that in the centre of the displacement range. The lead screw and worm gear or rack and pinion systems have the advantage that they can maintain constant forces over their full displacement range. The velocity of the plunger displacement determines the injection time, which is a parameter in determining patient comfort. Finally, the maximum force that the electrically powered source of drive of the drive unit can produce will determine the limits of drug viscosity and/or needle bore that the device can use in injections. In general, the maximum plunger velocity and maximum force will be inversely related. That is, higher injection force will limit the velocity achievable.

Interaction of Cassette Unit with Drive Unit

The syringe is movable within the drive unit housing from a rest position, in which the needle tip of the syringe is within the drive unit housing to a use position, in which the needle tip protrudes from the needle delivery aperture of the drive unit housing.

In embodiments, the syringe is in fixed relationship to the cassette unit housing and the required movement of the syringe is by movement of the cassette unit housing and syringe fixed thereto within the drive unit housing.

In other embodiments, the syringe is in movable relationship to the cassette unit housing and the required movement of the syringe is by movement of the syringe within the cassette unit housing.

In other embodiments, composite arrangements are envisaged, in which the syringe movement is achieved by a combination of both movement of the syringe within the cassette unit housing and by movement of the cassette unit housing within the drive unit housing.

In embodiments, the drive unit housing and/or any inner drive unit housing sub assembly thereof includes a needle projection aperture through which the hollow needle may protrude, for example during expelling of the liquid drug formulation through the hollow needle and its needle tip for delivery to the patient.

In embodiments, it is desirable for safety and hygiene reasons that the needle does not protrude from (i.e. out with) the drive unit housing other than when expelling the liquid drug formulation during an injection procedure. Thus, the drive unit housing and/or any inner drive unit housing sub assembly thereof and drive unit housing cavity defined thereby is generally arranged such that a needle receiving part thereof allows for the needle of the syringe to be axially moveable therein from the rest position in which the needle is wholly housed (or shrouded) by the needle receiving part to the use position in which at least the tip of the needle protrudes from that needle receiving part of the drive unit housing.

In embodiments, the drive unit housing includes biasing means (e.g. a spring) arranged to act on the syringe and/or the cassette unit housing such that the needle of the syringe is normally biased towards the rest position, wherein such biasing means are overcome during the actuation of the syringe (e.g. by an actuating mechanism) to allow for movement of the needle to the use position.

In embodiments, it is desirable for drive unit housing to allow for the needle of the syringe to be refracted into the housing after use. Thus, it is desirable to be able to retract the needle back into the needle receiving part of the housing after the injection procedure, that is to say to retract the needle from the use position to a retracted position that may in embodiments, correspond to the rest position or in other embodiments, correspond to a third position, which in embodiments is further away from the needle delivery aperture. A needle retract mechanism may thus, be provided (e.g. responsive to a biasing means such as a light return spring or by reverse action of the drive mechanism) to retract the syringe needle back into the drive unit housing.

In embodiments, it is desirable for the drive unit housing to allow for the needle of the syringe to be shrouded by a needle shroud element after use. Thus, in particular it is desirable to be able to provide a means of shrouding the needle of the syringe that is moved or otherwise brought into operation after completion the injection procedure. Such means in embodiments comprises a movable shroud element that is adapted to be movable to a shrouding configuration at the end of the injection procedure.

In embodiments, the drive unit includes a cassette unit holder for holding the cassette unit within the drive unit housing. In embodiments, the cassette unit holder defines one or more inner walls against at least a part of which the cassette unit seats when held within the cassette unit holder.

In embodiments, the cassette unit holder is sized and shaped such as to allow for a relatively tight clearance between the cassette unit and the inner walls of the cassette unit holder. Such tight tolerances allow for reliable positioning of the cassette unit within the cassette unit holder and drive unit.

In embodiments, the cassette unit holder is mounted within the drive unit for movement along the drive axis, which corresponds to the injection axis, thereby allowing for movement of the cassette unit and syringe within the drive unit between its rest and in use (i.e. injected) positions. In embodiments, the cassette unit holder mounts to a linear slide that orients along a direction that is parallel with or corresponds to the drive axis.

In embodiments, the cassette unit holder is provided with one or more cassette unit locking features for reversibly locking the cassette unit within the holder and hence, within the drive unit.

In embodiments, the one or more cassette unit locking features are arranged to be in a locking position when the cassette unit is in the docking position.

In embodiments, in the locking position the one or more locking features of the cassette unit housing align with corresponding features (e.g. apertures) of the cassette unit holder.

In embodiments, movement of the cassette unit from the intermediate pre-docking position to the docking position results in movement of the one or more locking features from the non-locking to the locking position.

In embodiments, each cassette unit locking feature comprises a latching feature, lock tab feature or snap-lock feature. In embodiments, engagement of the locking feature provides tactile or audible feedback to the user as an indication that the cassette unit has been correctly received within the cassette unit holder of the drive unit.

In embodiments, the cassette unit holder is provided with one or more cassette unit locking features protruding from the inner wall(s) thereof. In embodiments, the cassette unit locking features are biased towards (e.g. in response to biasing means) or naturally bias towards the cassette locking position.

In embodiments, the cassette unit holder has plural (e.g. two) cassette unit locking features (e.g. snap lock-tabs) integral with and protruding inwards from the walls thereof.

In embodiments, each of the cassette unit locking features has one or more angled faces arranged such that the locking feature may be pushed outwards as a result of force applied to the angled face.

In embodiments, each cassette unit locking feature (e.g. lock tab) has angled faces at the top and bottom thereof arranged such that the locking feature (e.g. lock tab) flexes outwards when a force (e.g. from an edge of another mechanical part) is pushed into them from either direction. In embodiments, the angled face at the bottom side of the locking feature allow for it to flex out of the way as the cassette unit is inserted into the cassette unit holder until the cassette unit is inserted to a holding and locking position, wherein the locking feature flexes back to its original position and lockingly engages the cassette unit housing. In this position the cassette unit is held in the cassette unit holder by the locking features (e.g. lock-tabs) because the top faces of the locking features (e.g. lock-tabs) support the cassette unit. The angled faces on the top of the locking features (e.g. lock-tabs) also allow for the cassette unit to be pulled out of the cassette unit holder by having the lock-tabs flex outwards in a similar fashion as when a cassette unit is inserted into the cassette unit holder of the drive unit of the auto-injector.

In embodiments, once the cassette unit has been inserted initially into the cassette unit holder, a reader of the drive unit reads an identifier on the cassette unit to verify details relating to it. Once positive verification has been established, the cassette unit is transported to the docking position such as by drawing it into the drive unit. In embodiments, this receipt of the cassette into the cassette unit holder corresponds to the pre-docking intermediate position referred to hereinafter.

In embodiments, as the cassette is transported to the docking position within the drive unit, the one or more locking features of the cassette unit holder are aligned with rigid features within the drive unit that maintain the locking features in the locking position such as by preventing lock-tabs from flexing outwards. Thus, the cassette unit is effectively locked within the drive unit when the locking features are aligned with these rigid features of the drive unit.

In embodiments, the length of the rigid features of the drive unit are arranged such that the cassette unit cannot be locked in the drive unit with the needle protruding from the needle delivery aperture such as at any insertion depth of the needle. Typically during the injection process, high loads are transmitted from the plunger through the cassette unit and reacted on the top surfaces of the locking features (e.g. lock-tabs). In embodiments where the top surface is angled, there is a horizontal component to the reaction load that attempts to flex the locking features (e.g. lock-tabs) outwards. However, where the locking features (e.g. lock-tabs) are aligned with (e.g. behind) the rigid features of the drive unit they cannot be flexed outwards and the cassette unit remains rigidly fixed in the drive unit.

In embodiments, once the cassette unit has been received at the docking position the removable cap and needle cover attached thereto is removed. Where in embodiments, there is a cap lock feature, this is first released. In embodiments, as the cassette is moved to the docking position (e.g. by being drawn fully up into the drive unit) the cassette unit is also brought into contact with cap lock unlocking features, which in embodiments comprise one or more (e.g. two) rigid arms, which extend into the cassette unit to depress, and thereby to unlock, the cap lock feature. In embodiments, the cap lock unlocking features are not rigidly fixed within the drive unit, and the rigid arms thereof that move into the cassette unit to depress, and thereby to unlock, the cap lock feature pass through cut-outs in the top of the cassette unit holder.

In embodiments, the drive unit is provided with a timer (e.g. timer function) that starts a time count on removal of the removable cap and needle cover from the cassette unit. In embodiments, the timer function is initiated by the removal of the removable cap and needle cover from the cassette unit. In embodiments, the timer counts upwards (i.e. from zero) on removal of the removable cap and needle cover). In other embodiments, the timer counts downwards (i.e. from a pre-determined time count) on removal of the removable cap and needle cover. Thus, for example an indication of time remaining to safely use the device may be calculated.

In embodiments, the timer is arranged such that on reaching a certain, pre-determined time count a stop command to stop the drive functioning of the drive unit is generated. Drive action of the drive unit is thus, prevented. In embodiments, the stop command is to disable (e.g. switch off or de-power) said one or more electrically powered sources of axial drive. In embodiments, the stop command is to initiate a blocking function that acts to block the movement of said first and/or second drive transfer elements. In embodiments, the timer therefore acts to ensure that drug is delivered to the patient within a set time limit following removal of the removable cap and needle cover from the syringe of the cassette unit.

In embodiments, one or more cap removal sensors (e.g. cap removal sensing means) are provided to detect removal of the removable cap and needle cover from the cassette unit. In embodiments, the one or more cap removal sensors communicate with the timer (e.g. via an electronic data unit or control unit) to send a cap removal detection signal to the timer to initiate the time count thereof.

In embodiments, the drive unit includes an electronic display and the time count is displayed on the electronic display.

In embodiments, to move the cassette unit within the drive unit, a first drive transfer element (e.g. a lead-screw) connects to (e.g. by threading through) a flange connecting to the cassette unit holder.

In embodiments, the cassette unit holder mounts to a linear slide such that it is slidably movable in a direction parallel to or corresponding to the drive axis. In embodiments, the first drive transfer element (e.g. lead-screw) couples to the output shaft of a motor/gear-head assembly such as via a universal joint. The universal joint allows for misalignment between the drive axis and the linear slide, which allows that the cassette unit holder and motor can be held rigidly in the drive unit without over-constraining the positioning of the cassette unit holder. Over-constraining the cassette unit holder could cause excessive friction or binding in the threads of the lead-screw and nut and so make high accelerations and velocities of the cassette unit holder difficult to achieve.

In embodiments, the lead-screw has four starts and a lead of 6.35 mm. Such a high lead allows for rapid linear accelerations of the cassette unit holder so that the needle can reach a velocity of 100 mm/sec before it pierces the patient's skin. In embodiments, this mechanism is arranged such as to be back-drivable.

In embodiments, the nut attached to the cassette unit holder has a specific linear travel for a given rotation of the screw. In consequence, the depth the needle is inserted into the patient is set by the rotational position of the screw. The position of the screw can be determined using several means including encoders and monitoring step-counts, in cases in which the motor being used is a stepper motor.

In embodiments, the drive unit can be configured to provide any suitable needle insertion depth with a typical needle insertion depth being between about 4 and 8 mm. Once the needle has been inserted into the patient, the injection of drug may be initiated. To inject the drug, axial drive force is applied to the second drive transfer element (e.g. plunger rod) to drivably move the plunger within the syringe barrel.

In embodiments, to apply the necessary driving load to the syringe plunger a second drive transfer element in the form of lead screw (e.g. a plunger screw) is rotated through a nut that is fixed relative to the syringe. Since the nut is fixed, the lead screw advances linearly as it is rotated. Having the nut fixed relative to the syringe allows for the plunger screw to stay fixed relative to the syringe when the cassette unit holder is moved within the device for needle insertion or retraction in an emergency. Otherwise, in embodiments, the plunger screw would be required to travel the distance that the cassette unit holder moves during needle insertion prior to its being able to make contact with the syringe to apply drive load to the syringe plunger. In embodiments, in the case of emergency retraction when the cassette unit holder needs to be moved into the drive unit in the middle of an injection, the plunger screw would have to be moved into the drive unit before the cassette unit could be rapidly retracted into the drive unit.

In embodiments, during an injection, loads reaching near 60N are applied to the syringe plunger via the second drive transfer element (e.g. the plunger screw).

In embodiments, the second drive transfer element (e.g. the rotating plunger screw) could direct undesirably high (e.g. torsion) drive loads on the system if the second drive transfer element makes direct contact with the syringe plunger. To minimize these torsion loads, the syringe barrel of the cassette unit may be provided with a plunger slaving part. Thus, the second drive transfer element acts to transfer axial drive to the plunger slaving part and hence, to the plunger of the syringe for moving the plunger into the barrel of the syringe to eject at least part of said volume of liquid drug formulation.

In embodiments, the plunger slaving part is in contact with the plunger of the syringe and is axially movable within the barrel. In embodiments, the plunger slaving part is arranged such that when a drive load is applied to a rear (e.g. top) drive-receiving face thereof the drive load is evenly transmitted to the plunger. In embodiments, the plunger slaving part engages (e.g. is in threaded engagement) with the plunger. In embodiments, the diameter of the plunger slaving part corresponds to the diameter of the plunger.

In embodiments, the plunger is made of a material that is resiliently compressible (e.g. rubber or an organic polymeric material) and the plunger slaving part is made of a less compressible material. In embodiments, the plunger slaving part is made of a rigid material (e.g. a hard plastic polymer material such as poly propylene).

In embodiments, the rear face of the plunger slaving part has a central recess for receipt of a drive transfer element. In embodiments, the central recess is of conical form. Thus in embodiments, the second drive transfer element defines a drive end arranged for receipt by the central recess of the rear drive-receiving face of the plunger slaving part. In embodiments, the drive end defines a conical tip and said central recess is of conical form to guide and centre said conical tip therein. In embodiments, the angle of the conical recess is greater than the angle of the conical tip.

In embodiments, the slaving part may be configured to perform a second purpose of providing an easy-to-identify visual indicator of the plunger's position within the syringe so that the patient can visually confirm the drug had been fully injected. In this embodiment, the slaving part may be called a stopper position indicator.

In the above described plunger screw embodiment, the plunger screw is rotated through a fixed nut. In consequence, the combination of the high linear force with the rotating plunger screw could result in high torsion loads on the system if the plunger screw makes direct contact with the syringe plunger. To minimize these torsion loads, the plunger screw is in embodiments, provided with a pointed tip to give rise to a point load instead of a face load. The pointed tip of the plunger screw makes contact with a slaving part, which is made of a hard material, thus acting to reduce friction and torsion loads on the system. The slaving part contacts (e.g. engages) the plunger such that when a load is applied to its top face the load is evenly transmitted directly into the plunger. In embodiments, the top of the slaving part has a conical recess to guide and centre the pointed end of the plunger screw as it is lowered into contact. In embodiments, the angle of the conical recess is greater than the angle of the conical end of the plunger screw to achieve point contact between the tip of the plunger screw and the top surface, while also guiding the syringe plunger during its travel.

In embodiments, the plunger screw is rotated by a screw gear, which receives drive force from the source of axial drive. In embodiments, the plunger screw slide fits through the center of the gear and is keyed to gear via a flat. Since in this embodiment, the plunger screw has a flat, there are sharp corners where the flat is cut across the threads. In consequence, reliefs are provided in the walls of pass-through hole in the screw gear to eliminate the possibility of the thread corners from catching on the screw gear as the plunger screw slides through it. In embodiments, the screw gear is fixed within the device via a press-fit with a ball bearing that is fixed within the drive unit.

In embodiments, to control the position and angular velocity of the screw gear, and thus the position and velocity of the plunger screw, the screw gear is arranged to mesh with a gear mounting to the shaft of a motor/gearhead assembly. In embodiments, the rotation and angular velocity of the output of the motor/gearhead shaft directly correlates to the position and velocity of the plunger screw. Thus, the position of the plunger screw is determined by the rotational position of the screw. This position of the plunger screw is in embodiments, monitored using encoders anywhere in the drive train that has rotating components or by monitoring step-counts if using a stepper motor.

In embodiments, the drive unit is arranged to initially receive the cassette unit housing at an intermediate pre-docking position for subsequent transport of the cassette unit to the docking position.

In embodiments, the drive unit is arranged to initially receive the cassette unit housing at the intermediate pre-docking position for automated verification thereof. Such verification can for example, be for the purpose of checking of drug and dosage information, checking that the drug is not past its expiry date and/or checking that the cassette has not been used previously.

In embodiments, the cassette unit is receivable by a cassette unit holder of the drive unit and the position corresponding to (e.g. initial) receipt of the cassette into the cassette unit holder corresponds to the intermediate position at which the automatic verification step is carried out.

In embodiments, the cassette unit further comprises an identifier. The identifier comprises data in a form that may be readily subject to interrogation. The drive unit comprises a reader for reading (interrogating) the identifier of the cassette unit and, in communication with the reader, a verifier for verifying the identifier.

In embodiments, the drive unit is arranged such that transport of the cassette unit to the docking position is permitted only following positive verification of the identifier. Thus, only appropriately identified cassette units are finally receivable into the device to enable injected drug delivery there from.

In embodiments, the identifier may include labelling selected from the group consisting of visual text, machine-readable text, bar codes, and dot codes. In embodiments, the identifier is in the form of a passive transceiver (e.g. an RFID tag) that is interrogable by means of an active transceiver (e.g. an RFID reader). In embodiments, the identifier is in the form of a bar code that is interrogable by means of a bar code reader.

In embodiments, the cassette unit comprises a first transceiver for transmitting and receiving data and the drive unit comprises a second transceiver for transmitting and receiving data, wherein data is transferable at least from the first transceiver to the second transceiver, and in embodiments in two-way fashion from the first transceiver to the second transceiver. The data is in embodiments in digital form and suitable for transfer by electronic, radio or optical means.

An advantage of embodiments of this type is the ability to store many types of information in different parts of the memory structure of the transceivers. The information is furthermore stored in a form, which is readily and accurately transferable. The information could for example, include manufacturing and distribution compliance information written to the memory at various points in the manufacturing or distribution process, thereby providing a detailed and readily accessible product history of the cassette unit housing. Such product history information may, for example, be referred to in the event of a product recall. The compliance information could, for example, include date and time stamps. The information could also include a unique serial number stored in encrypted form or in a password protectable part of the memory, which uniquely identifies the drug product and therefore may assist in the detection and prevention of counterfeiting. The information could also include basic product information such as the nature of the drug and dosing information, customer information such as the name of the intended customer, and distribution information such as the intended product destination.

On loading the drive unit with the cassette unit housing the second transceiver may, for example, read the unique serial number, batch code and expiry date of the drug and any other information on the first transceiver. In this way the nature and concentration of the drug in the syringe of the cassette unit, may be determined. Other information, such as the date and time of administration of the drug, or environmental exposure data such as the minimum/maximum temperatures or levels of humidity the cassette unit has been exposed to, may also be read and displayed to the user. In embodiments, this information is displayed to the patient on a visual display unit.

Data may also be transferred to and from any transceiver during the period of use of the auto-injector by the patient. For example, the auto-injector may include an electronic data system having various sensors associated therewith. Any data collected by the sensors or from any data collection system associated with the electronic data system including a clock or other date/time recorder is transferable. Data may be transferred each time the patient uses the auto-injector. Or alternatively, data may be stored in a database memory of the electronic data system and periodically downloaded to any transceiver. In either case, a history of the usage of the auto-injector may be built up in the memory of any transceiver.

In embodiments, the first and second transceiver each comprise an antenna or equivalent for transmitting or receiving data and connecting thereto a memory. The memory will typically comprise an integrated circuit chip. Either transceiver may be configured to have a memory structure, which allows for large amounts of information to be stored thereon. The memory structure can be arranged such that parts of the memory are read-only, being programmed during/after manufacture, other parts are read/write and further parts are password protectable. Initial transfer of information (e.g. at the time of manufacture or of dispensing) to or from any transceiver can be arranged to be readily achievable by the use of a reader which is remote from the auto-injector, thereby minimising the need for direct product handling.

In embodiments, data is transferable (e.g. in two-way fashion) between the first transceiver on the cassette unit and second transceiver on the drive unit without the need for direct physical contact therebetween. In embodiments, data is transferable wirelessly between the first and second transceiver.

In embodiments, the second transceiver on the drive unit is an active transceiver and the first transceiver on the cassette unit is a passive transceiver. The term active is used to mean directly powered and the term passive is used to mean indirectly powered.

In embodiments, the first transceiver on the cassette unit comprises an identifier or tag comprising an antenna for transmitting or receiving interrogating energy; and an integrated circuit chip connecting with said antenna, and the second transceiver on the drive unit comprises a reader for said identifier or tag. In this case the identifier or tag is a passive transceiver and the reader is an active transceiver. In embodiments, the reader is not in direct contact with the tag or identifier that is to be read.

In embodiments, the integrated circuit chip has a read only memory area, a write only memory area, a read/write memory area or combinations thereof. In embodiments, the integrated circuit chip has a one-time programmable memory area. In embodiments, the one-time programmable memory area contains a unique serial number. In embodiments, the integrated circuit chip has a preset memory area containing a factory preset, non-changeable, unique data item. In embodiments, the preset memory item is in encrypted form. In embodiments, the integrated circuit chip has plural memory areas thereon. In embodiments, any memory area is password protected. In embodiments, any memory area contains data in encrypted form. Electronic methods of checking identity, error detection and data transfer may also be employed. In embodiments, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

In embodiments, the tag is on a carrier and the carrier is mountable on the cassette unit. In embodiments, the carrier comprises an insulating material such as a glass material or, a paper material or an organic polymeric material such as polypropylene.

The interrogating energy may be in any suitable form including ultrasonic, infrared, radiofrequency, magnetic, optical and laser form. Any suitable channels may be used to channel the energy including fibre optic channels.

In embodiments, the first transceiver on the cassette comprises a radiofrequency identifier (RFID) comprising an antenna for transmitting or receiving radiofrequency energy; and an integrated circuit chip connecting with said antenna, and the second transceiver comprises a reader for said radiofrequency identifier. In this case the radiofrequency identifier is a passive transceiver and the reader is an active transceiver. An advantage of radiofrequency identifier technology is that the reader need not be in direct contact with the radiofrequency identifier tag or identifier to be read.

The radiofrequency identifier can be any known radiofrequency identifier. Such identifiers are sometimes known as radiofrequency transponders or radiofrequency identification (RFID) tags or identifiers. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

In embodiments, the antenna of the RFID tag is capable of transmitting or receiving radiofrequency energy having a frequency of from 100 kHz to 2.5 GHz. Preferred operating frequencies are selected from 125 kHz, 13.56 MHz and 2.4 GHz.

In embodiments, the first transceiver on the cassette unit comprises a magnetic identifier or tag comprising an antenna for transmitting or receiving magnetic field energy; and an integrated circuit chip connecting with said antenna, and the second transceiver on the drive unit comprises a reader for said magnetic identifier or tag. In this case the magnetic identifier or tag is a passive transceiver and the reader is an active transceiver.

In embodiments, the first transceiver on the cassette unit comprises a microelectronic memory chip and the second transceiver on the drive unit comprises a reader for said microelectronic memory chip. The microelectronic memory chip may comprise an Electrically Erasable Programmable Read Only Memory (EEPROM) chip, a SIM card-type memory chip or a flash type memory chip. In this case the microelectronic memory chip is a passive transceiver and the reader is an active transceiver.

Once the reader has read (or interrogated) the identifier of the cassette unit, that identifier data is communicated to a verifier, which conducts a verification step.

In embodiments, the verifier carries out the verification by comparing one or more pieces of data read from the identifier with acceptable data values. In embodiments, the comparison makes reference to a look-up table of acceptable values, which may include data that is patient specific. In one embodiment, the acceptable values of look-up table are pre-loaded into an electronic data unit of the drive unit. In another embodiment, the acceptable values of look-up table are downloadable to an electronic data unit of the drive unit (e.g. by communicating with an online data source). In one embodiment, the acceptable values of look-up table are calculable by an electronic data unit of the drive unit (e.g. based on data input by the user or feed-ins from sensors of the device). In one example, the data relates to type of drug with a comparison being made between the type of drug contained within the syringe and that required by the patient. In another example, the data relates to the 'use by' date of the drug with verification being made by reference to an electronic calendar of the electronic data unit of the drive unit with positive verification being registered only if the 'use by' date of the drug has not been exceeded. In another example, the data relates to the 'lot number' of the cassette unit and a check is made against whether that 'lot number' has been subject to a recall or not.

In embodiments, the drive unit is arranged such that transport of the cassette unit from the intermediate position to the docking position is permitted only following positive verification of the identifier. Thus, only appropriately verified cassette units are finally receivable into the device for drug delivery there from.

In embodiments, that transport of the cassette unit to the docking position is by automatic control under the action of the electrically powered source of drive. Thus, in embodiments positive verification of the cassette unit gives rise to a 'transport to docking position' signal from the electronic data unit to the source of drive, which results in the required transporting action.

In embodiments, the drive unit comprises a compartment for storage of one or more cassette units.

Electronic Data System

In embodiments, the auto-injector additionally comprises an electronic data system, typically under the control of one or more microcomputers. In embodiments, the electronic data system has input/output capability and comprises a memory for storage of data; one or more microprocessors for performing operations on said data; and a transmitter for transmitting a signal relating to the data or the outcome of an operation on the data. In embodiments, the electronic data system is arranged to be responsive to or activated by the voice of a user. Thus, for example the electronic data system may be switched on or off in response to a voice command.

In embodiments, the electronic data system is integral with the drive unit. Alternatively, the electronic data system forms part of an electronic data unit such as on a circuit board or plug-in, which is reversibly associable with the drive unit.

In embodiments, the drive unit or separable electronic data unit additionally comprises a data input system for user input of data to the electronic data system. In embodiments, the data input system comprises a man machine interface (MMI) in embodiments selected from a keypad, voice recognition interface, graphical user interface (GUI) or biometrics interface.

In embodiments, the electronic data system additionally comprises a visual display unit for display of data to the user. The display may for example, comprise a screen such as an LED or LCD screen. In embodiments the visual display unit is associable with the drive unit.

In embodiments, the auto-injector additionally comprises a data link for linking to a local data store to enable communication of data between the local data store and the electronic data system. The data store may also comprise data management, data analysis and data communication capability.

The data store may itself form part of a portable device (e.g. a handheld device) or it may be sized and shaped to be accommodated within the patient's home. The data store may also comprise a physical storage area for storage of replacement cassette units. The data store may further comprise an electrical recharging system for recharging any electrical energy store of the drive unit, particularly a battery recharging system.

The data link may for example enable linking with a docking station, a personal computer, a network computer system or a set-top box by any suitable method including a hard-wired link, an infrared link or any other suitable wireless communications link.

In embodiments, the auto-injector additionally comprises a communicator for wireless communication with a network computer system to enable transfer of data between the network computer system and the electronic data system. In embodiments, the communicator enables two-way transfer of data between the network computer system and the electronic data system. Wi-Fi enabled communicators are envisaged.

In embodiments, the data is communicable between the network computer system and the electronic data system in encrypted form. All suitable methods of encryption or partial encryption are envisaged. Password protection may also be employed. In embodiments, the communicator employs radiofrequency or optical signals.

In embodiments, the communicator communicates via a gateway to the network computer system. In another aspect, the communicator includes a network server (e.g. a web server) such that it may directly communicate with the network.

In a further aspect, the communicator communicates with the gateway via a second communications device. In embodiments, the second communications device is a telecommunications device, more in embodiments a cellular phone or pager. In embodiments, the communicator communicates with the second communications device using spread spectrum radiofrequency signals. A suitable spread spectrum protocol is the Bluetooth (trade mark) standard, which employs rapid (e.g. 1600 times a second) hopping between plural frequencies (e.g. 79 different frequencies). The protocol may further employ multiple sending of data bits (e.g. sending in triplicate) to reduce interference.

In embodiments, the network computer system comprises a public access network computer system. The Internet is one suitable example of a public access network computer system, wherein the point of access thereto can be any suitable entry point including an entry point managed by an Internet service provider. The public access network computer system may also form part of a telecommunications system, which may itself be a traditional copper wire system, a cellular system or an optical network.

In another aspect, the network computer system comprises a private access network computer system. The private access network system may for example, comprise an Intranet or Extranet, which may for example, be maintained by a health service provider or drug manufacturer. The network may for example include password protection; a firewall; and suitable encryption means.

In embodiments, the communicator enables communication with a user-specific network address in the network computer system. The user-specific network address may be selected from the group consisting of a web-site address; an e-mail address and a file transfer protocol address. In embodiments, the user-specific network address is accessible to a remote information source such that information from said remote information source might be made available thereto.

In embodiments, information from the user-specific network address is made available to the remote information source. In embodiments, the remote information source is a source of drug prescriptions, for example a doctor's practice or a hospital; a pharmacy; an emergency assistance provider; a manufacturer of drugs; or a research establishment.

In embodiments, the auto-injector additionally comprises a geographic positioning system such as a global positioning system or a system, which relies on the use of multiple communications signals and a triangulation algorithm.

In embodiments, the auto-injector additionally comprises an orientation sensor for checking on the orientation thereof. In embodiments, the auto-injector is arranged to operate only when in certain defined orientations (e.g. upright or nearly so).

Kit of Parts

In embodiments, there is also provided a kit of parts comprising a cassette unit (absent syringe) as described above; and a syringe containing a liquid drug formulation.

In embodiments, there is further provided a kit of parts comprising a cassette unit (which may in embodiments, be in kit of parts form) as described above; and a drive unit as described above.

In embodiments, there is further provided a kit of parts comprising an auto-injector (which may in embodiments, be in kit of parts form) as described above; and packaging therefor. Suitable packaging typically comprises a storage container for the drive unit and one or more cassette units.

In certain implementations, an injection kit includes a cassette unit housing having an inner surface and a plurality of syringe barrels having different physical dimensions. The kit may also include a plurality of sleeve form adapters configured to receive at least one of the syringe barrels, where the sleeve form adapter has an outer surface configured to interfit with the inner surface of the cassette unit housing.

In certain embodiments, each syringe barrel has a unique circumference size or a unique contoured surface that mates with the sleeve form adapter.

Method of Assembling a Medicament-Injector

In certain implementations, a method of assembly a medicament-injector includes selecting a syringe barrel among a plurality of syringe barrels, each of the plurality of syringe barrels having a different physical dimension than is found in the other of the plurality. The method may also include selecting a sleeve form adapter configured to mate with the selected syringe barrel, interfitting the syringe barrel within the sleeve form adapter, and installing the sleeve form adapter within a cassette unit. In certain embodiments, each syringe barrel has a unique circumference size or a unique contoured surface that mates with the sleeve form adapter.

BRIEF DESCRIPTION OF THE DRAWINGS

The disclosure is further described with reference to the accompanying drawings, in which:

FIGS. 6a and 6b are perspective and cross sectional view of a first needle cover for use with the first cassette unit of FIGS. 1 to 4;

FIGS. 7a and 7b are perspective and cross sectional view of a rigid needle shield for use with the needle cover of FIGS. 6a and 6b;

FIGS. 24a to 24i are sectional views also showing sequential use steps of a first drive unit of FIGS. 17 to 20 with a first cassette unit of FIGS. 1 to 4, but with the view rotated 135° compared to those views of FIGS. 23a to 23i;

DETAILED DESCRIPTION

To provide an overall understanding of the systems, devices and methods described herein, certain illustrative embodiments will now be described. For the purpose of clarity and illustration these systems and methods will be described with respect to auto-injectors that employ electrically powered drive units and cassette units that receive medicament syringes. It will be understood by one of ordinary skill in the art that the systems, devices and methods described herein may be adapted and modified as is appropriate, and that these systems, devices and methods may be employed in other suitable applications, such as for other types of drive units and cassette units, and that other such additions and modifications will not depart from the scope hereof.

Figure 1:
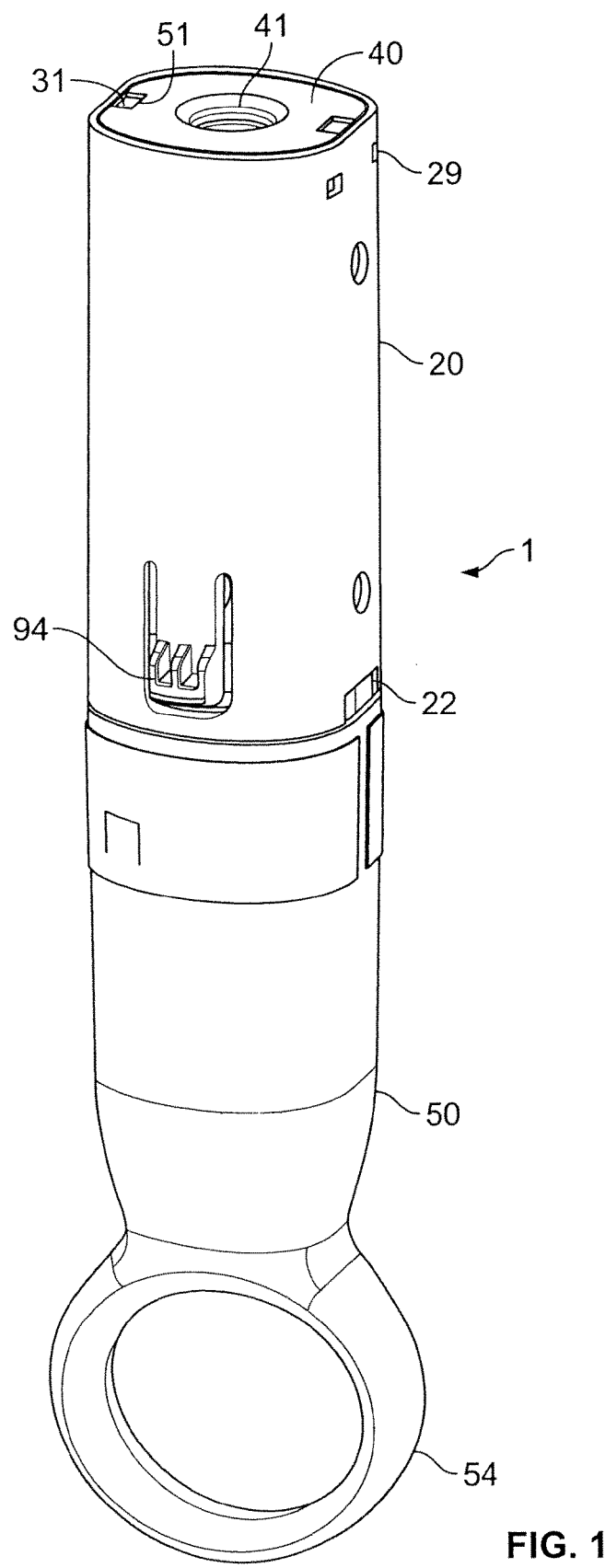
FIG. 1 is a perspective view of a first cassette unit of an auto-injector herein and shown in the 'pre-use' configuration.
Figure 2:
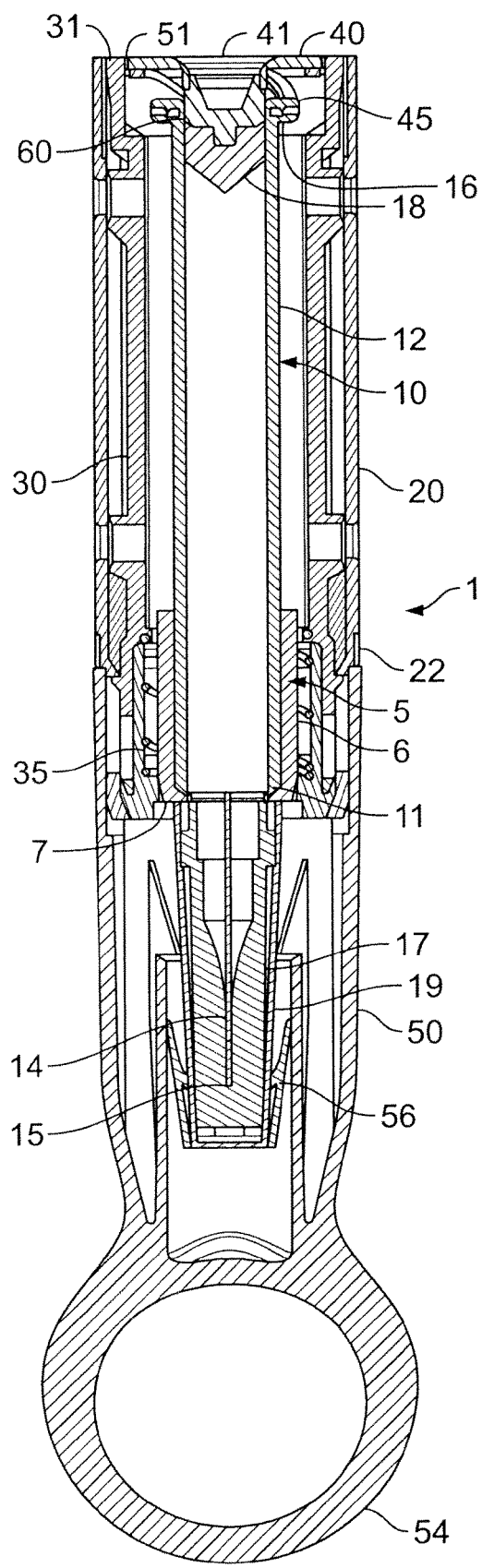
FIG. 2 is a sectional view of the first cassette unit of FIG. 1 arranged for use with a 1 ml syringe also in the 'pre-use' configuration.
Figure 3:
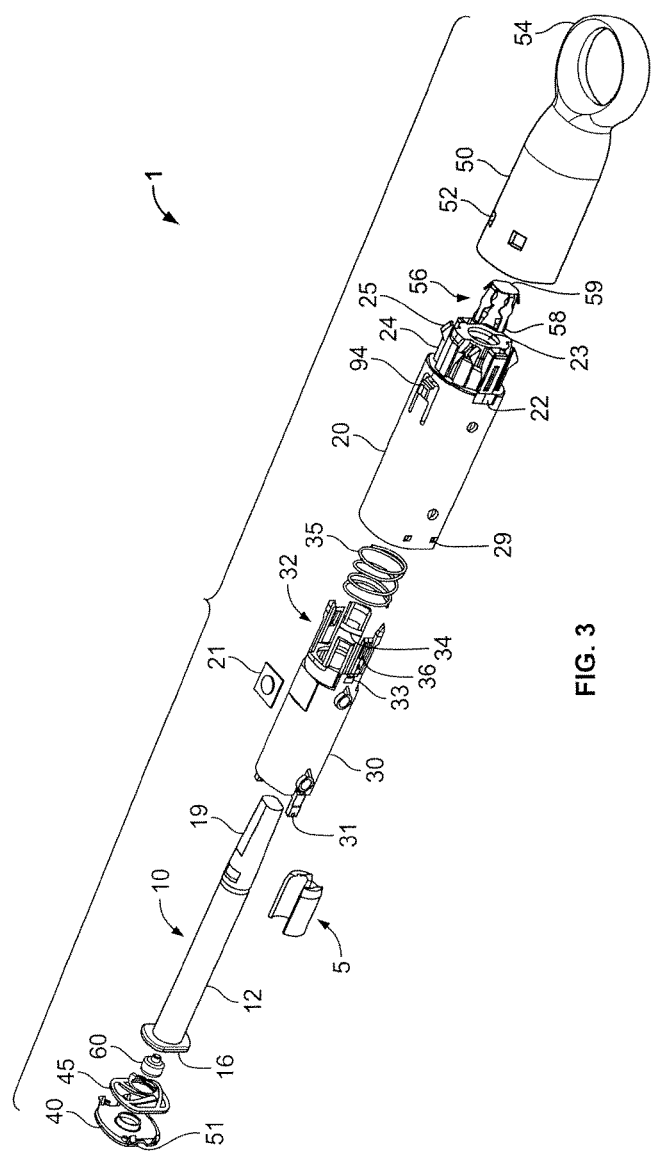
FIG. 3 is an exploded view of the first cassette unit of FIG. 1.
Figure 4:
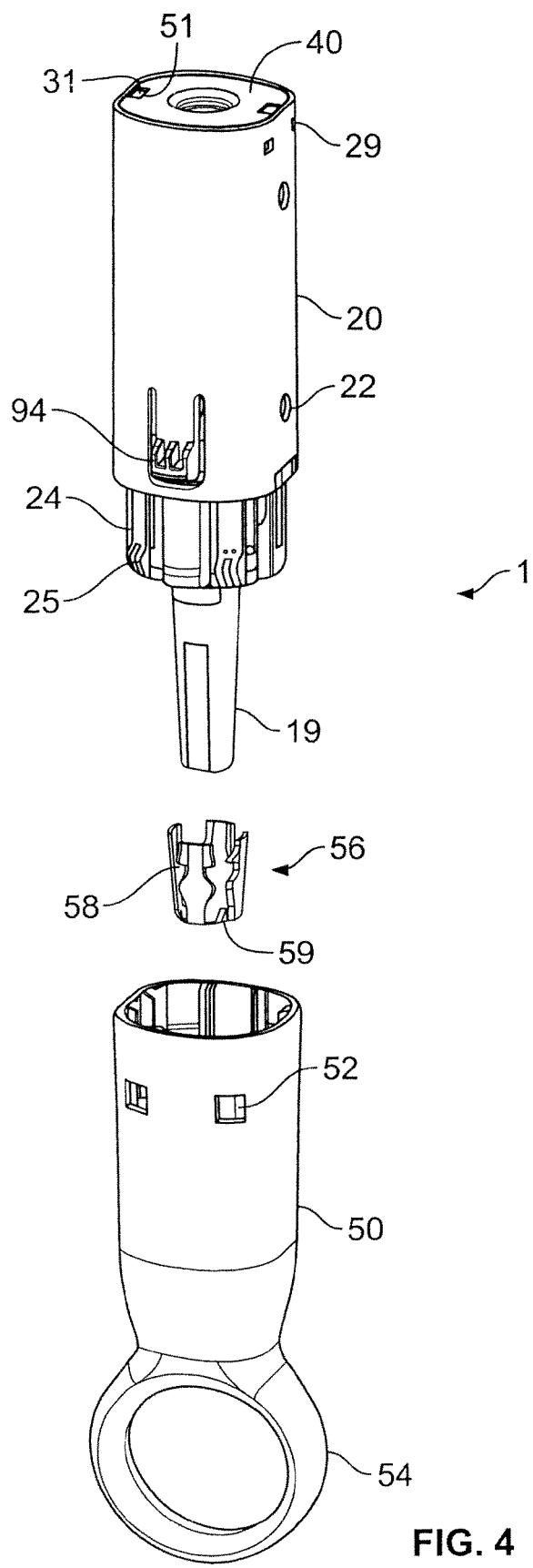
FIG. 4 is a part-exploded view of the first cassette unit of FIG. 1 showing in greater detail the relation between needle cover, needle cover gripper and removable cap.

FIGS. 1 to 4 show a first cassette unit 1 of an auto-injector herein arranged for use with a 1 ml syringe 10 that contains a liquid drug formulation (not shown). The cassette unit 1 comprises an elongate form cassette unit housing 20 having an end cap 40 that is arranged for receipt of the syringe 10 and is sized and shaped for this purpose. The cassette unit housing 20 is provided with a viewing window 22 that allows for viewing of a 'used cassette flag' 33 provided to inner housing sleeve 30 to provide a visual indication of use, the operation of which will be described in more detail hereinafter. The cassette unit housing 20 is further provided with security label 21, which may in aspects be an RFID tag label for use in verification purposes. The cassette unit 1 is provided with a removable cap 50 that is arranged to engage the needle cover 19 of the syringe 10 that is shown at FIGS. 1 and 2 in the capped position. The cap 50 is provided at the brim thereof with a peripheral arrangement of through-hole (i.e. socket like) first engagement features 52 (not visible on FIG. 2). The cap 50 is shaped to define a ring pull 54 for receipt by the finger of a user.

Needle cover gripper 56 in the form of a cage-like (or 'flower') structure and defining plural gripping elements 58 arranged about a central hub 59 is further provided to the removable cap 50. Such gripping elements 58 are arranged for gripping of the rigid needle sheath shield 19 on removal of the removable cap 50 such that removal of the cap 50 also results in removal of the rigid needle sheath shield 19 and needle sheath 17 enclosed thereby, and hence, unsheathing of the needle tip 15.

The gripping ring 54 of the removable cap defines a finger aperture to receive a patient's thumb or other preferred finger for pulling the removable cap away from the cassette unit 1 to expose the needle 14. In certain embodiments, the finger aperture is adapted to receive a hook that some patients use to pull the removable cap 50 away from the cassette unit 1. The removable cap 50 with gripping ring 54 makes it easier for patients to engage and disengage the needle cover 17 and rigid needle shield 19 from the syringe barrel 12 as it does not require the patient to contort their fingers by pressing on the sides of a narrow needle cover 17/19. As noted before, the present auto-injector is intended for use by patients having compromised manual dexterity who may therefore experience difficulty pulling a conventional needle cover 17 and/or rigid needle shield 19 off the syringe 10 before self-injection. The gripping ring 54 addresses this need by allowing the patient to simply put the thumb or other preferred finger through the finger aperture 54 and pull on the removable cap to thereby remove the needle cover 17 and rigid needle shield 19.

The syringe 10 is of a standard 1 ml type and comprises a barrel 12 with end flange 16 for holding a liquid drug formulation; a hollow needle 14 at one end of the barrel 12; and a syringe plunger 18 in the form of a rubber stopper that is arranged for axial movement within the barrel 12 such as to enable the liquid drug formulation to be expelled through the hollow needle 14. As shown at FIG. 2, the syringe plunger 18 is at the 'pre-use' position. The hollow needle 14 defines a needle bore, which is of circular cross-section (e.g. 23 G, 25 G or 27 G diameter) and a needle tip 15. The needle tip 15 is sheathed by needle sheath 17, which is also provided with rigid needle sheath shell 19. More detail of this relationship is now described by reference to FIGS. 6A to 7B, which illustrate an exemplary arrangement of needle sheath 17 and needle cover 19.

FIG. 6a depicts a perspective view of an exemplary embodiment of a sheath-like needle cover 17, which is cylindrical in shape and defines a shoulder 17a at the rear end. The needle sheath 17 may be made out of rubbery material that allows a portion of the connector 56 to dig into the outer surface thereof, such as that defined by the shoulder 17a to permanently engage the needle sheath 17 to the connector 56. FIG. 6b shows a cross sectional view of the same needle sheath 17. As depicted, the needle cover 17 includes a needle receiving portion 17b that is arranged in use, for piercing receipt of the tip 15 of the needle 14 as for example, shown at FIG. 2. In embodiments, the needle receiving portion 17b is made from butadiene rubber. In certain embodiments, the needle sheath 17 is hollow, but other shaped arrangements of the interior of the needle sheath 17 are also possible.

FIGS. 7a and 7b show views of a rigid needle shield 19 for use with the needle sheath 17 of FIGS. 6a and 6b. Rectangular openings 19a are provided at the rear end of the needle shield for receipt of the shoulder 17a of the needle sheath 17 to enable the forming of a needle cover as may be seen at FIG. 2.

The cassette unit housing 20 of the cassette unit 1 is arranged to define a cassette unit housing cavity that is sized and shaped for generally fixed receipt of the syringe 10. The cassette unit housing 20 defines at its forward end a needle delivery aperture 23 through which in use, the hollow needle 14 of the syringe 10 and a portion of the glass hub thereof protrudes on removal of the cap 50 there from. The cassette unit housing 20 defines at its rearward end an end cap 40 adjacent to which the end flange 16 of the syringe 10 seats.

The cassette unit housing 20 is provided with a radial arrangement of first engagement features in the form of movable locking legs 24 defining angled tips 25 (not visible on FIG. 2) thereon arranged for reversibly engaging the corresponding radial arrangement of second engagement features in the form of socket through holes 52 of the removable cap 50 for reversible lock engagement of the removable cap 50 to the cassette unit housing 20.

The cassette unit 1 is provided with an inner housing sleeve 30 for sleeved receipt of the syringe 10. The rear part of the inner housing sleeve 30 is provided with a spaced pair of rearward protruding arms 31. The inner housing sleeve 30 also forms a shuttle lock control feature 32 defining a radial arrangement of blocking elements 34 for selectively blocking movement of the movable locking legs 24 of the cassette unit housing 20 relative to the socket holes 52 of the cap 50, thereby providing for selective control of cap locking/unlocking, more details of which are described hereinafter with reference to FIGS. 8a to 11c.

Figure 5A:
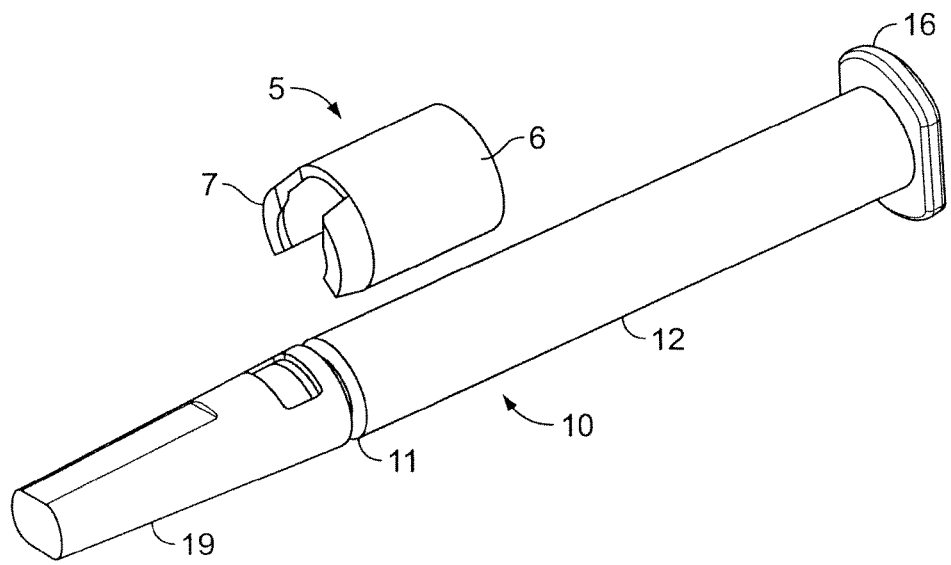
FIG. 5A is a part-exploded view of a syringe with shoulder support assembly suitable for use with the cassette unit of FIGS. 1 to 4.
Figure 5B:
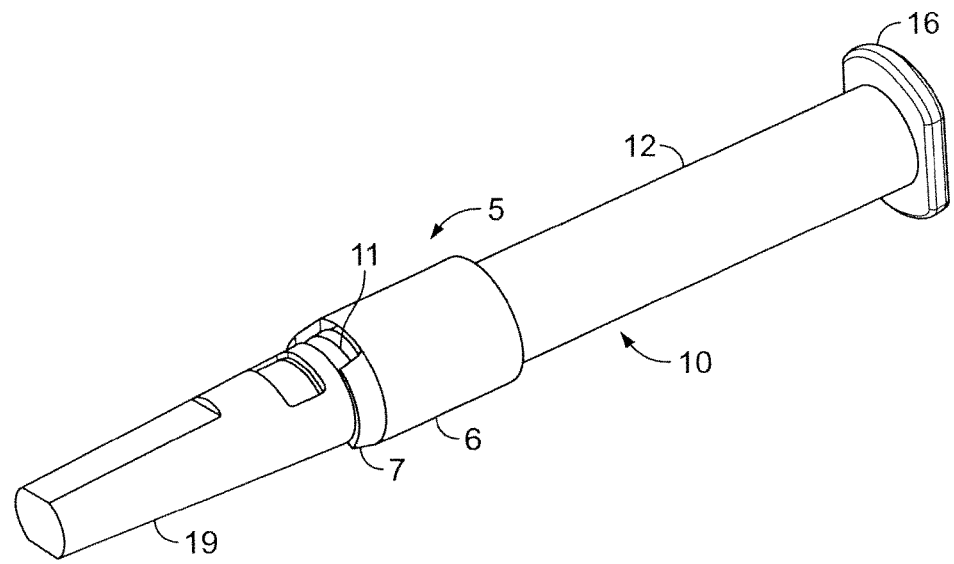
FIG. 5B is a perspective view of the syringe with shoulder support assembly of FIG. 5A.
Figure 5C:
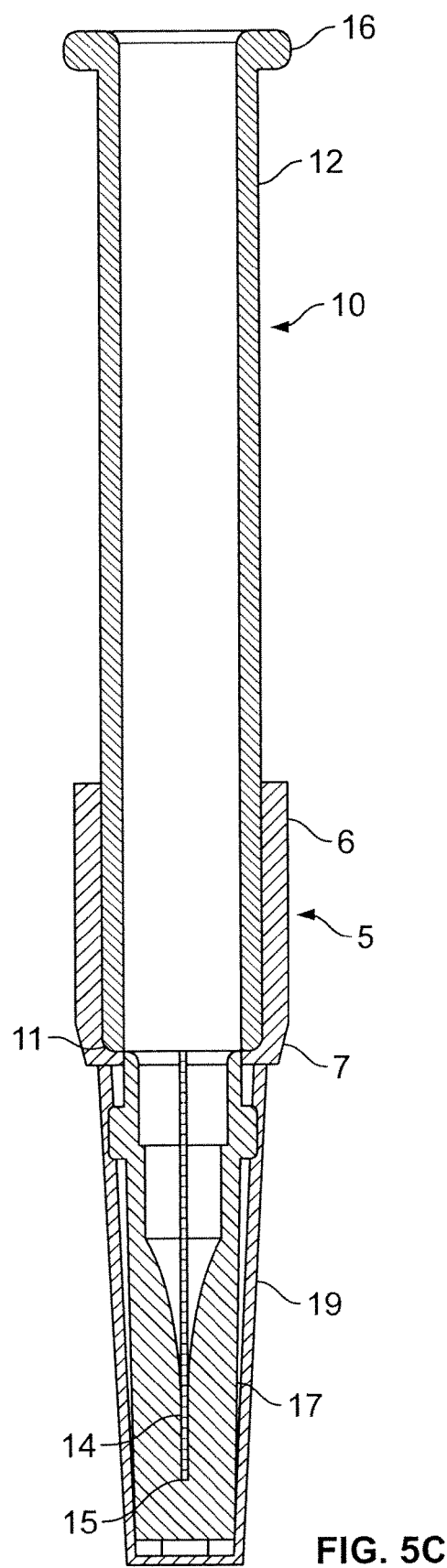
FIG. 5C is a sectional view of the syringe with shoulder support assembly of FIGS. 5A and 5B.

Applicant has found that to reduce the risk of the syringe 10 fracturing under the loads associated with injecting the drug, it is important for a majority of the load path to travel through the forward shoulder 11 of the syringe barrel 12 and lesser load to pass through the flange 16 at the rear end thereof. Thus, as further shown at FIGS. 5a to 5c but with syringe plunger 18 absent, the syringe 10 of the cassette unit 1 additionally comprises a shoulder support feature 5 for supporting the forward shoulder 11 of the syringe. The shoulder support feature 5 may also used to adapt a 1 ml syringe for use in the cassette unit 1. It supports the 1 ml syringe shoulder 11, and transmits the load through to the same surface that would support a 2.25 ml syringe shoulder directly.

The shoulder support feature 5 may be seen to comprise a split-barrel 6 that is sized and shaped for receipt by the syringe barrel 12 and a forward split lip 7 that is arranged to locate in snap-fit fashion between the rigid needle sheath shell 19 and the forward shoulder 11 of the syringe 10. In embodiments, the use of such a shoulder support feature 5 is to adapt the smaller diameter 1 ml syringe to the rigid shell 19 designed to support the 2.25 ml syringe shoulder 11. Provision may also made for poor dimensional control in the production of glass syringes.

Within the cassette unit 1, the shoulder support feature 5 for the syringe 10 interacts with the inner wall of the cassette unit housing 20, which thereby acts to constrain the position of the shoulder support feature 5 and syringe 10 within the cassette unit housing 20. The inner wall of the cassette unit housing 20 also prevents the forward split lip 7 of the shoulder support feature 5 from flexing outwards when injection loads are applied to the syringe 10. Thus, the forward shoulder 11 of the syringe 10 effectively captures the forward split lip 7 of the shoulder support feature. Also, the rearward split-barrel part 6 of the shoulder support feature 5 acts to sleeve a portion of the syringe barrel 12.

An additional consequence of this part-sleeved relationship between shoulder support feature 5 and syringe barrel 12 is to increase the effective diameter of the syringe barrel 12. By choice of different sizes, particularly inner diameters, of shoulder support feature 5 different syringe 10 sizes may be accommodated within the same cassette unit housing 20. Thus, the shoulder support 5 may also effectively be used as a syringe size adapter feature.

The syringe plunger 18 is provided with a plunger slaving part 60 that is axially movable within the syringe barrel 12 and for receipt by the rear end of the plunger 18. The syringe plunger 18 is made of a material that is resiliently compressible and the plunger slaving part 60 is made of a less compressible material, typically a rigid material.

Further structural details of the plunger slaving part 60 may be seen by reference to FIGS. 12, 13 and 14a to 14c. Thus, the plunger slaving part 60 defining a circumferential wall 62 arranged for frictional sliding relationship with the inner wall 12a of the syringe barrel 12, a rear drive-receiving face 63 and a front plunger-contacting face 64. The slaving part 60 is arranged to function such that when a load is applied to its drive-receiving face 63 the load is evenly transmitted directly into the plunger 18. As may be seen at FIGS. 13 and 14b, the rear drive-receiving face 63 of the plunger slaving part 60 has a central recess 65 for receipt of a drive transfer element. The central recess 65 is shaped such that the drive transfer element is rotatably receivable therein and has a recess form 65 that tapers to a square-cut end 66. The front plunger-contacting face 64 defines a protruding plug end 67 that is arranged for receipt by the rear end of the syringe plunger 18. In embodiments, the plug end 67 is designed to prevent collapse in use, of the plunger 18, which has a cavity in its centre into which a plunger rod may be screwed for manual syringe applications.

The circumferential wall 62 of the plunger slaving part is provided with an evenly spaced radial arrangement of slide restrictors 68 that function to restrict frictional sliding movement thereof in relation to the inner wall of the syringe barrel 18. Each of the slide restrictors comprises a flexible vane 68 arranged to flex slightly in response to frictional sliding movement of the plunger slaving part 60 and to thereby to increase the resistance of the plunger slaving part 60 to frictional sliding movement. In embodiments, the flexible vanes 68 are arranged to increase the initial resistance to forward frictional sliding movement but to impart lesser resistance to said forward frictional sliding movement once movement is underway. In embodiments, the flexible vanes 68 are arranged to more greatly increase the resistance to a backward frictional sliding movement than to the forward frictional sliding movement.

In embodiments, the slaving part 60 is coloured and performs a second function of providing an easy-to-identify visual indicator of the position of the plunger 18 within the syringe 10 so that the patient can visually confirm the drug had been fully injected. The flexible vanes 68 act such as to maintain the plunger slaving part 60 in the 'after use' (i.e. post-injection) position such that this indicator can be relied upon to signal this 'after use' state. In embodiments, the plunger slaving part 60 has a third function; one of tamper evidence: If an attempt is made to access the syringe 10 via the end-cap 40, the plunger slaving part 60 will be pushed out of engagement with the end-cap 40, resulting in visible evidence of tamper.

The cassette unit 1 includes, in capping relationship with a rear opening of the cassette unit housing 20, a cassette unit end-cap 40. Further structural details of the cassette unit end-cap 40 may be seen by reference to FIGS. 12 and 13. The cassette unit end-cap 40 defines a drive rod-receiving opening 41 for receipt of a drive rod (part of the drive unit, not shown) for providing forward axial drive to the plunger slaving part 60. Four fixing legs 39 with heels 38 locate at spaced intervals about the inner end wall of the end-cap 40 and protrude forwards for fixing receipt (not visible on FIG. 13) with fixing sockets 29 of the cassette unit housing 20.

The cassette unit end cap 40 also defines a spaced pair of cut-away apertures 51 positioned such that when the cassette unit end-cap 40 is in capped relationship with the cassette unit housing 20 the cut-away apertures 51 are in registration with the protruding arms 31 of the inner housing sleeve 30. Each cut-away aperture 51 is designed allow for insertion of a pushing member (e.g. a pin) such that forward pushing force may be applied to the top of the protruding arms 31 to push the inner housing sleeve 30 forward, thereby allowing for actuation of the shuttle lock control 32, as described in more detail hereinafter.

Figure 13:
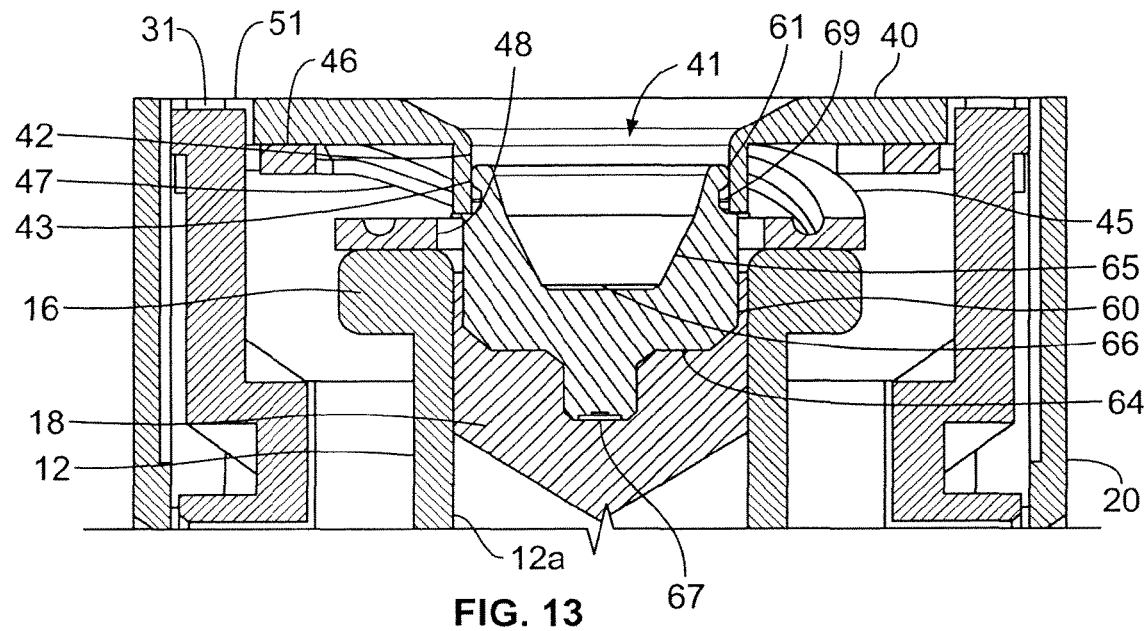
FIG. 13 is a sectional view of the upper part of the first cassette unit of FIGS. 1 to 4 showing details of end cap, end cap spring and plunger slaving part interaction with the rearward flange of the syringe within the cassette unit housing.
Figure 14A:
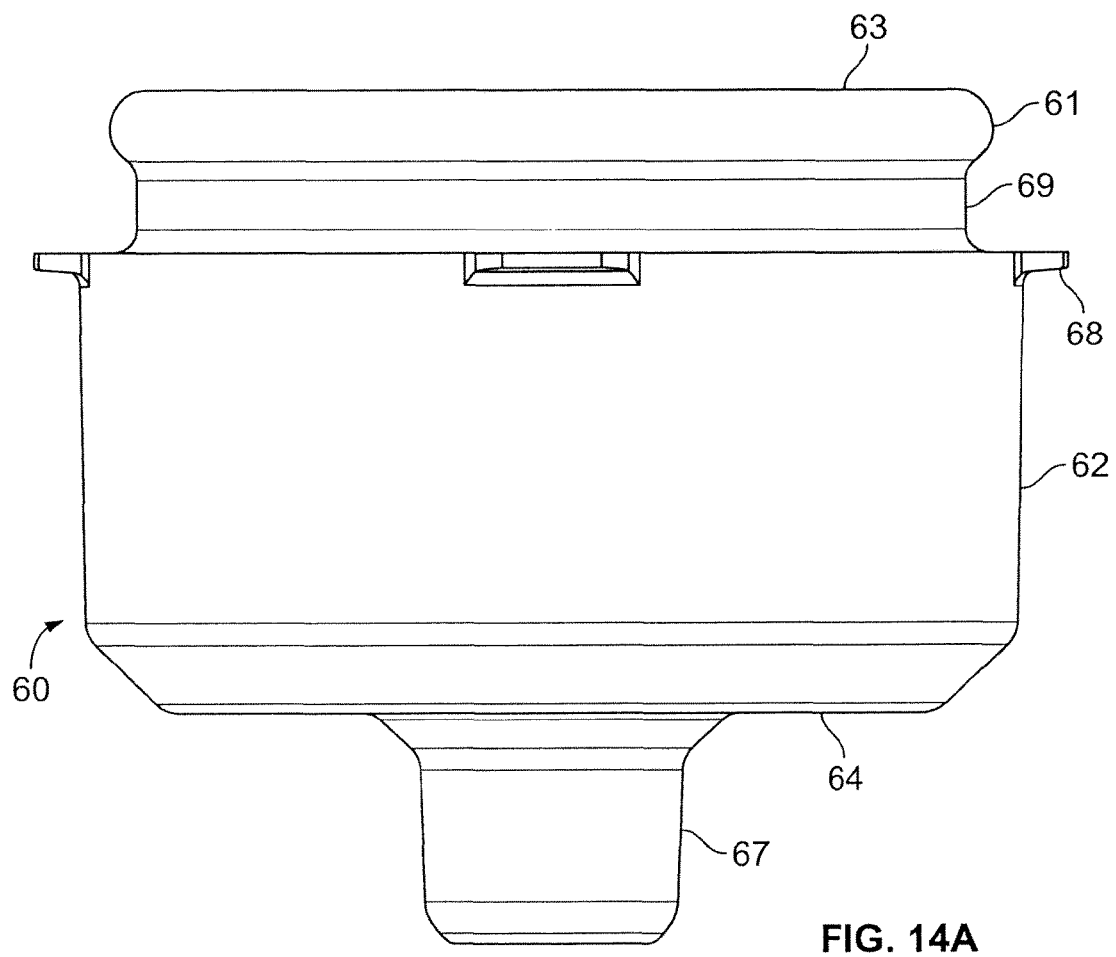
FIGS. 14a to 14c are side, rear plan and front plan views of a plunger slaving part for use with the first cassette unit of FIGS. 1 to 4.
Figure 14B:
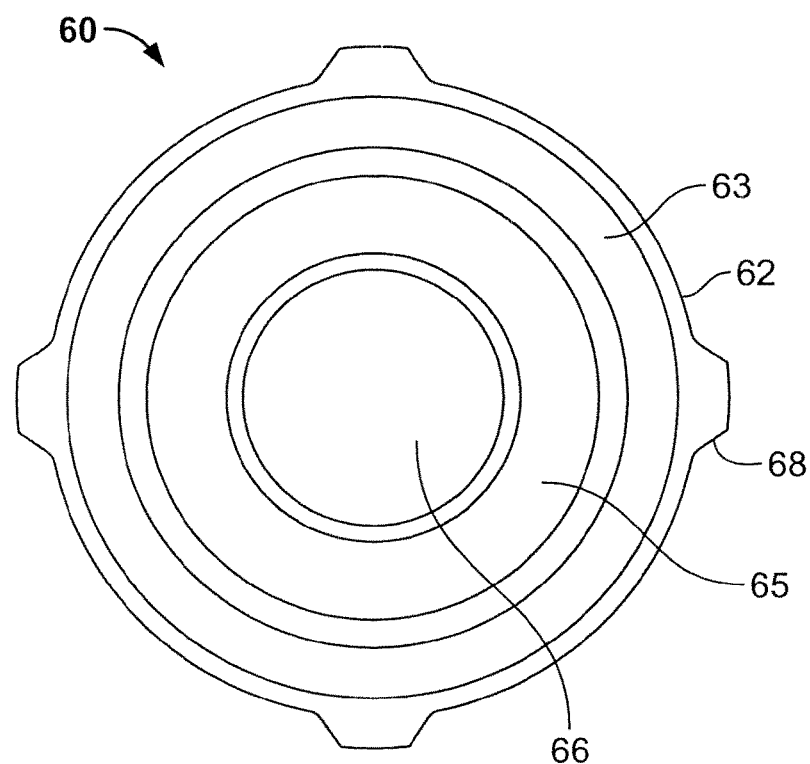
Figure 14C:
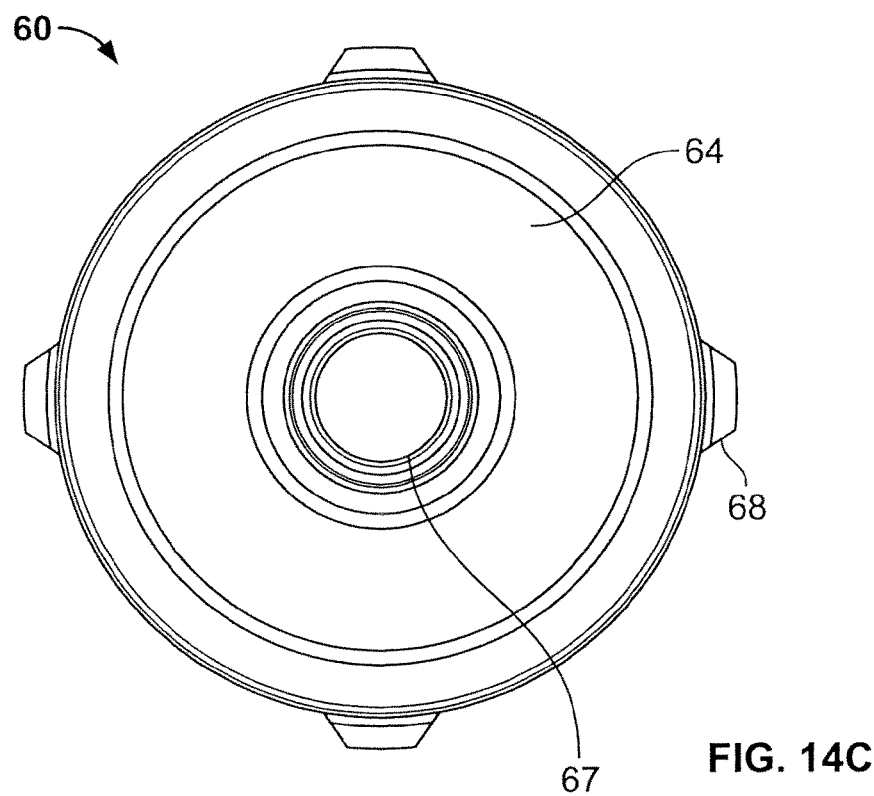
Figure 15A:
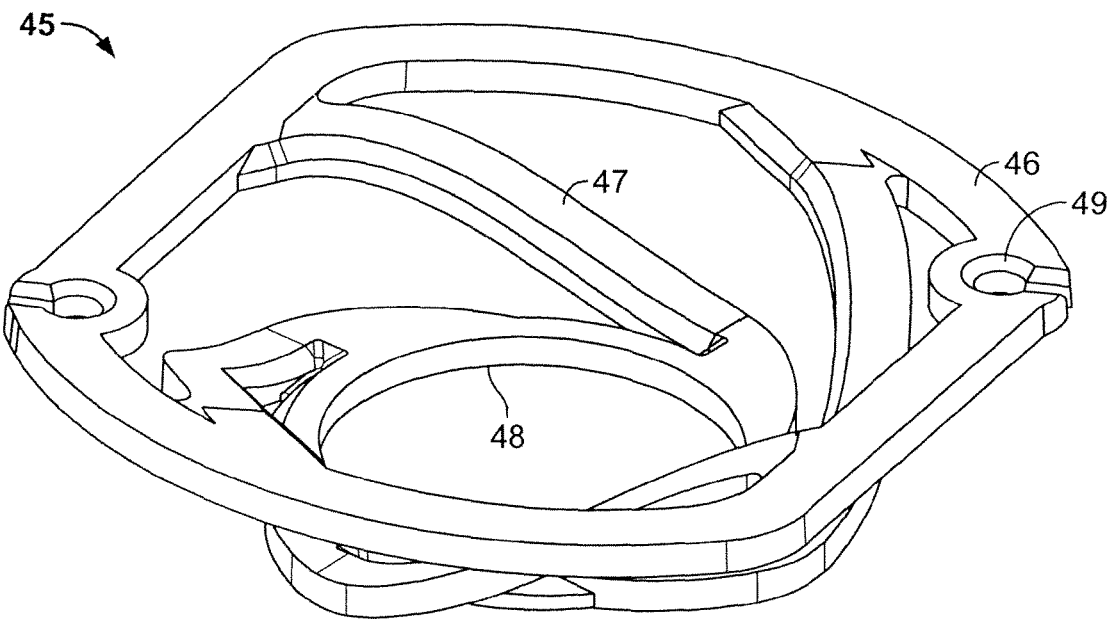
FIGS. 15a to 15d are perspective, side, rear plan and front plan views of an end cap spring for use with the first cassette unit of FIGS. 1 to 4.
Figure 15B:
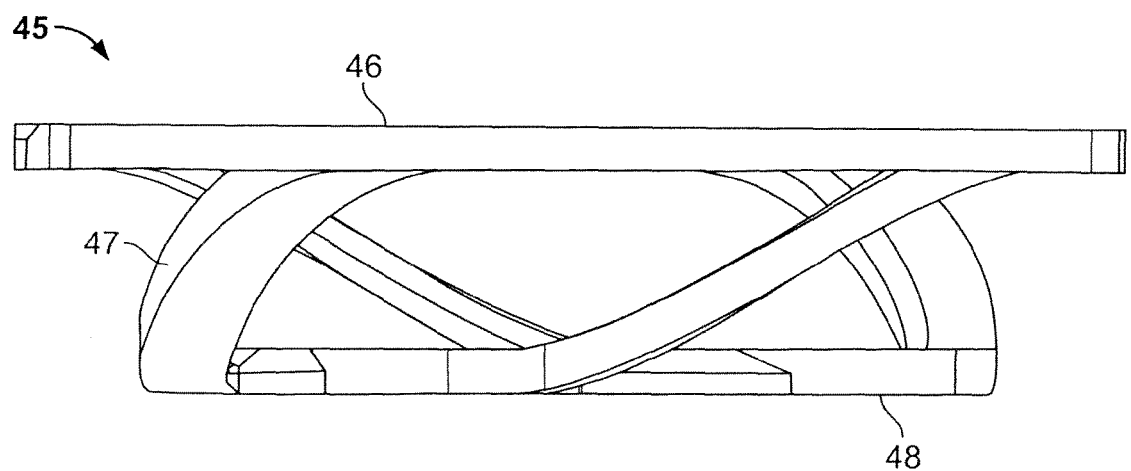
Figure 15C:
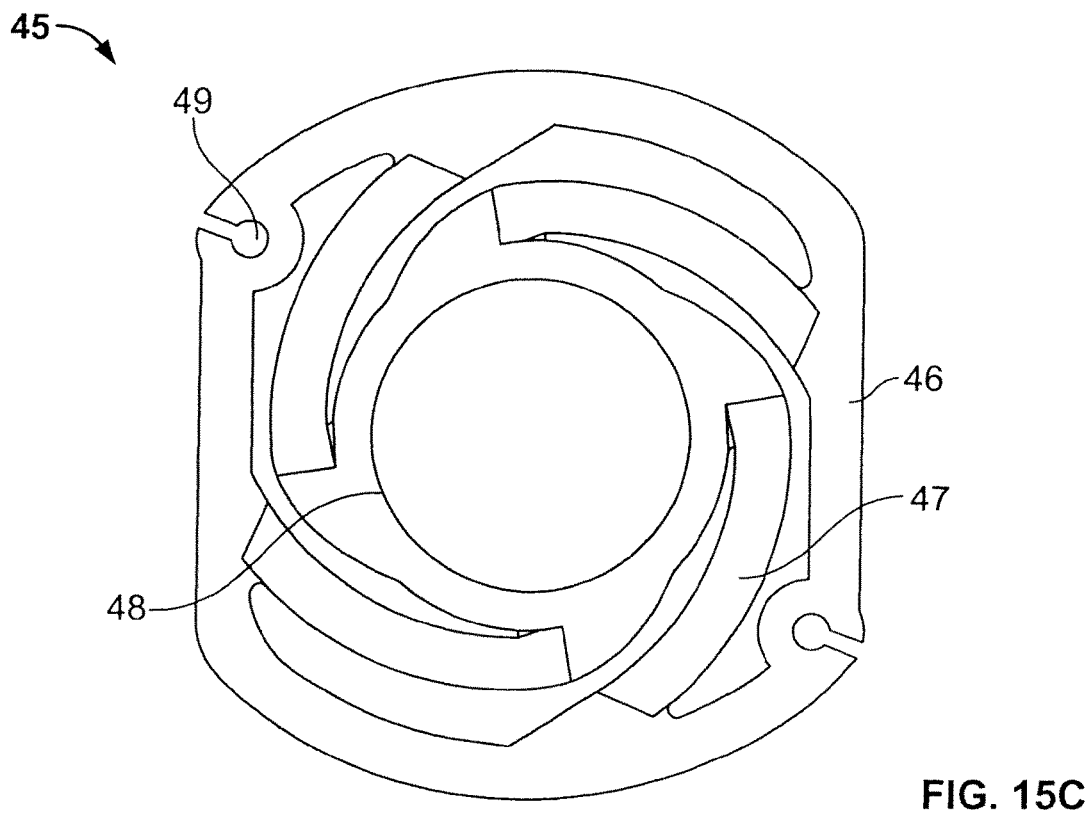
Figure 15D:
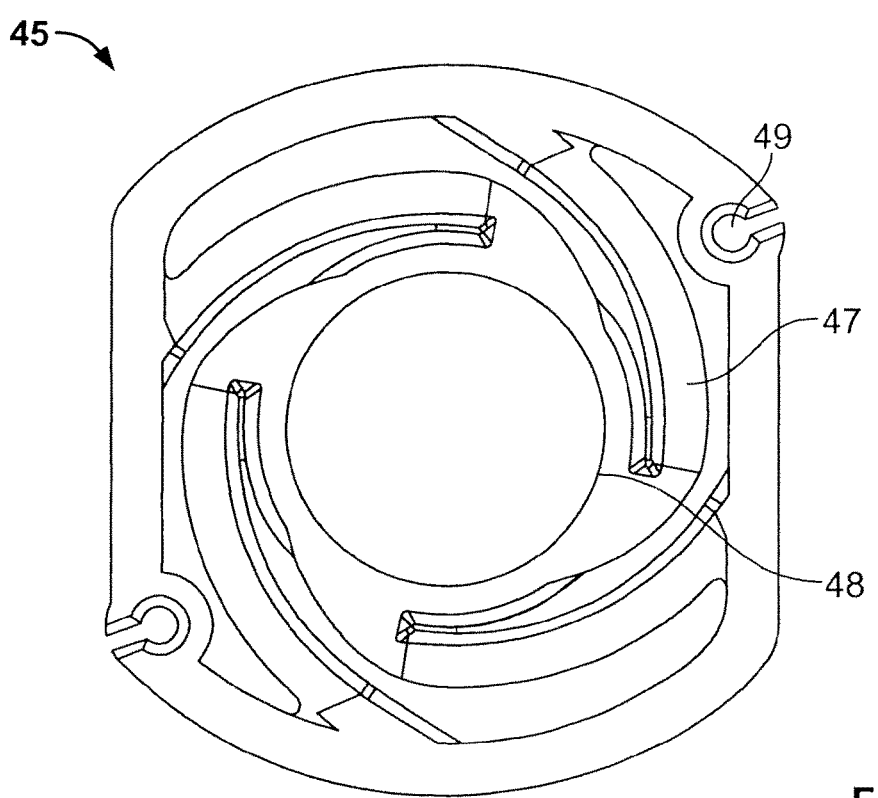
Figure 16A:
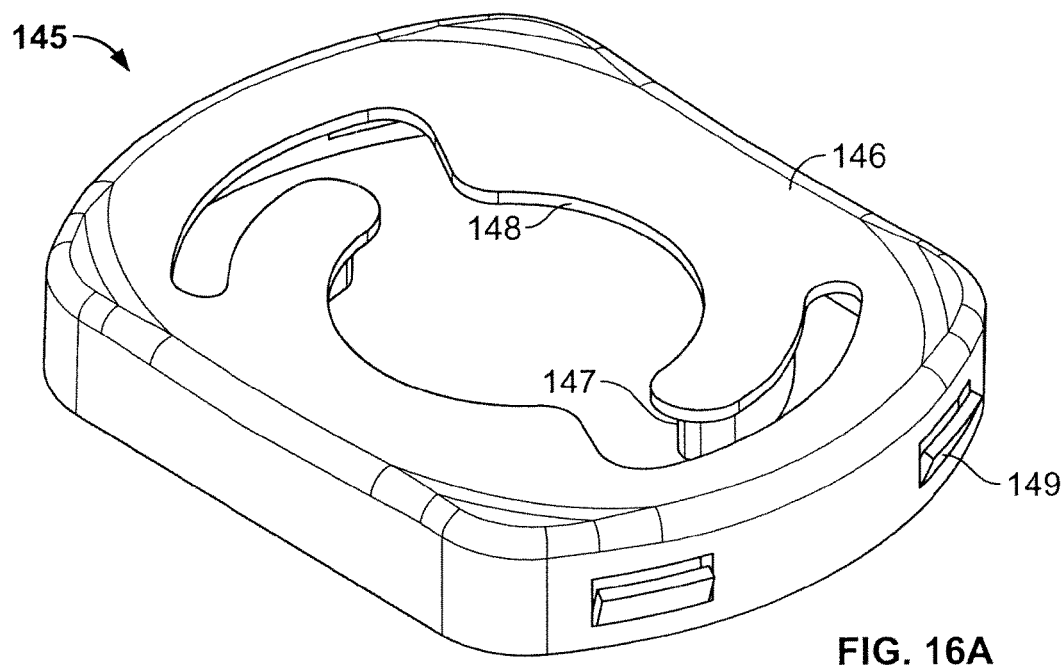
FIGS. 16a to 16e are perspective, rear plan, front plan, side and side rotated by 90° views of an alternative metal end cap spring for use with the first cassette unit of FIGS. 1 to 4.
Figure 16B:
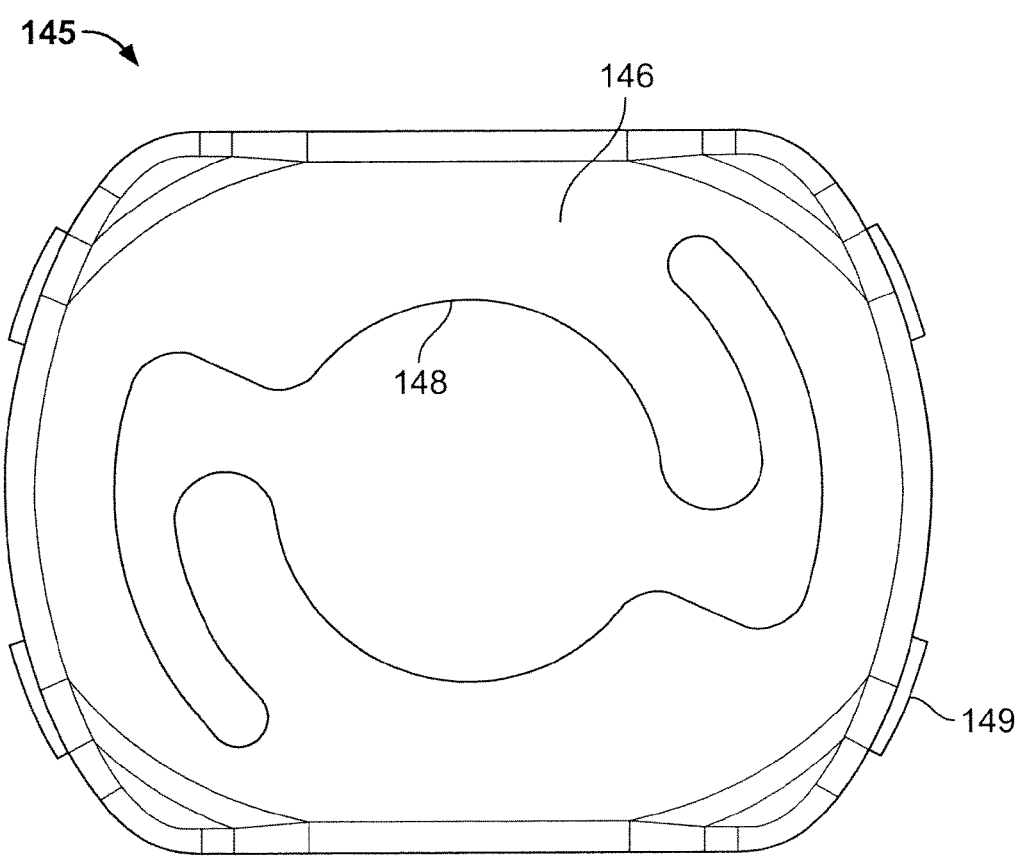
Figure 16C:
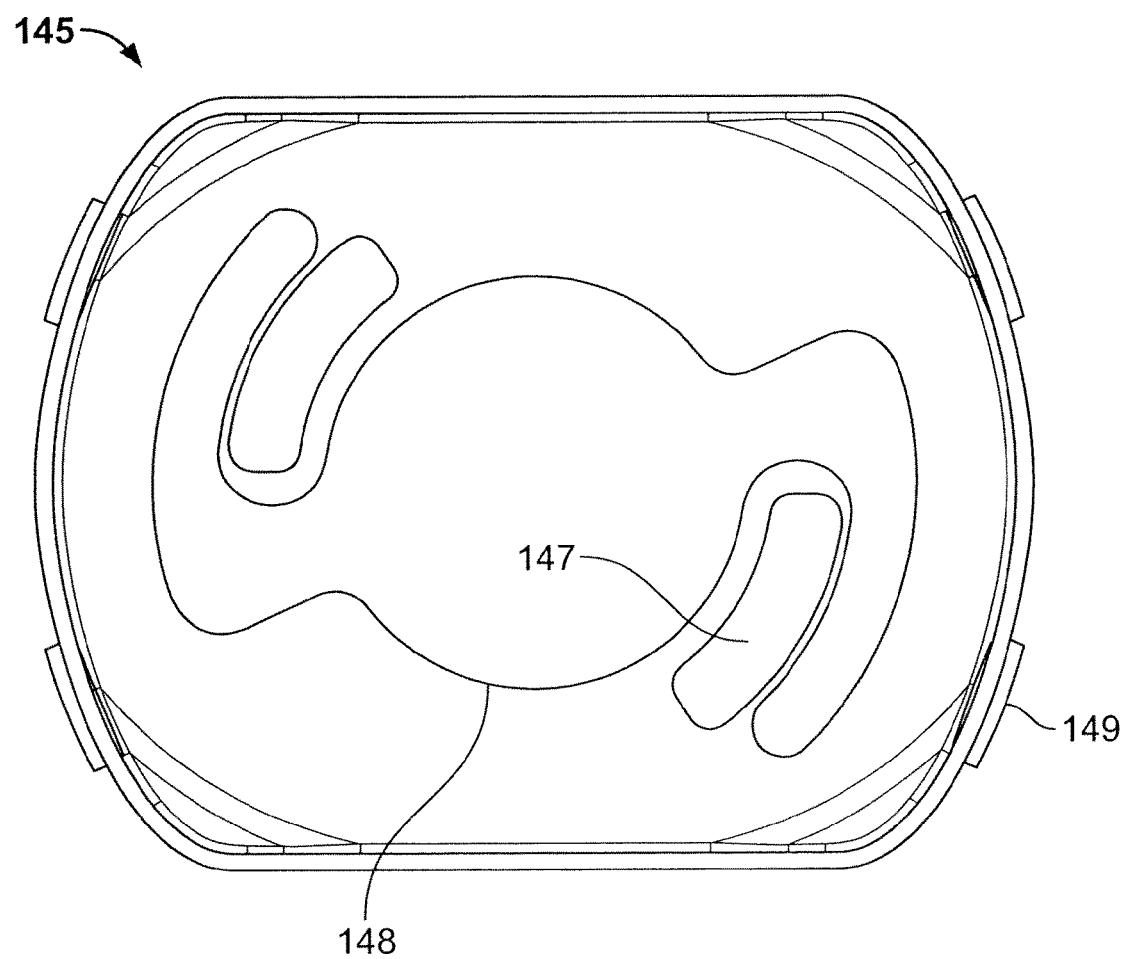
Figure 16D:
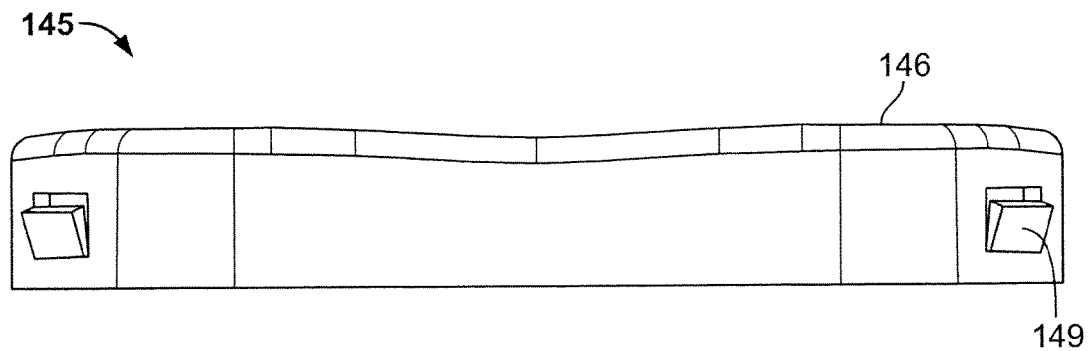
Figure 16E:
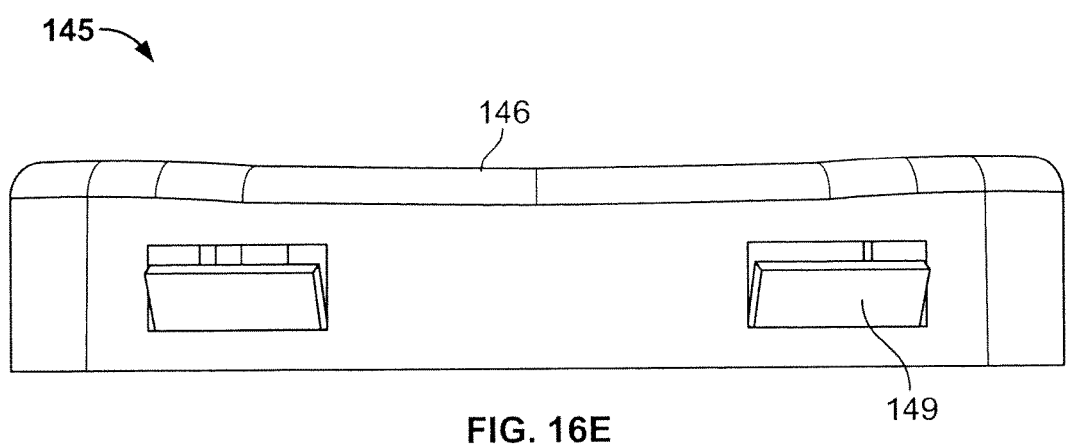

In the pre-use configuration (e.g. as shown at FIGS. 2 and 13), the plunger slaving part 60 is in releasable engagement with the cassette unit end-cap 40. Structurally, the drive rod-receiving opening 41 is defined by a periphery, which is provided with a forward skirt 42 and the plunger slaving part 60 is shaped for releasable engagement in the pre-use configuration with the forward skirt 42. In more detail and with particular reference to FIG. 13, the forward skirt 42 is provided with an inner-facing rim 43 and the plunger slaving part 60 defines a circumferential rim 61 and trough 69 shaped for releasable engagement in the pre-use configuration with the inner-facing rim 43 of the end-cap 40. In use, the plunger slaving part 60 is releasable from the cassette unit end-cap 40 in response to forward axial drive provided to said rear drive-receiving face 63, 66 thereof.

The cassette unit 1 additionally comprises an end-cap spring 45 defining a sprung biasing relationship between the cassette unit end-cap 40 and the flange 16 of the syringe 10, thereby urging the syringe 10 forwards in relation to the cassette unit end cap 40. The effect of this sprung relationship is to better hold the syringe 10 within the cassette unit housing 20, and in particular to minimize any potential for the syringe to 'rattle about' within the cassette unit housing 20. It will also be appreciated, particularly when reference is made to FIG. 2, that the effect of such urging forwards of the syringe 10 is also to bring the forward shoulder 11 of the syringe 10 into closer relationship with shoulder support feature 5, which sits between that forward shoulder 11 and the rigid needle sheath cover 19. Overall, thus the forward end of the syringe 10 thus, tends to be more supported. An additional effect of the spring 45 is to prevent rearward movement of the syringe 10 during needle insertion, ensuring that full insertion depth is achieved.

Further structural details of the end-cap spring 45, which is typically comprised of a polymeric material, may be seen by reference to FIGS. 12, 13 and 15a to 15d. The rear end 46 of the end-cap spring 45 defines an essentially flat profile, which allows it to seat up against the inner end wall of the end-cap 40 where it is held in place by the interaction of pegs 44 on the inner wall of the end-cap 40 with peg-sockets 49 on the rear end 46 of the end-cap spring 45. Sprung arms 47 extends forwards in spiral fashion and meet at circular ring 48 at the forward end of the end-cap spring 45. Within the cassette unit, this ring 48 is sized and shaped to fit about the forward skirt 42 of the end-cap 40 and when the plunger slaving part 60 is engaged with the end-cap 40 (e.g. as shown at FIGS. 2 and 13) about the outer circumferential wall 62 of the plunger slaving part 60.

In another embodiment shown at FIGS. 16a to 16e, an alternative end-cap spring 145 is constructed from metal. Whilst the detailed shaping of this alternative end-cap spring 145 varies from that of the end-cap spring 45 of FIGS. 15a to 15d its essential function is the same. The rear end 146 of the alternative end-cap spring 145 defines an essentially flat profile, which allows it to rest a small distance away from the inner end wall of the end-cap 40. The alternative end-cap spring is held in place by the interaction of the inner side wall of the cassette unit housing 20 with clips 149 on the side wall of the alternative end-cap spring 145. Sprung arms 147 extends forwards in part-spiral fashion about a central ring aperture 148. Within the cassette unit, this ring aperture 148 is sized and shaped to fit about the forward skirt 42 of the end-cap 40 and when the plunger slaving part 60 is engaged with the end-cap 40 (e.g. at a position corresponding to that shown at FIGS. 2 and 13) about the outer circumferential wall 62 of the plunger slaving part 60.

Figure 25:
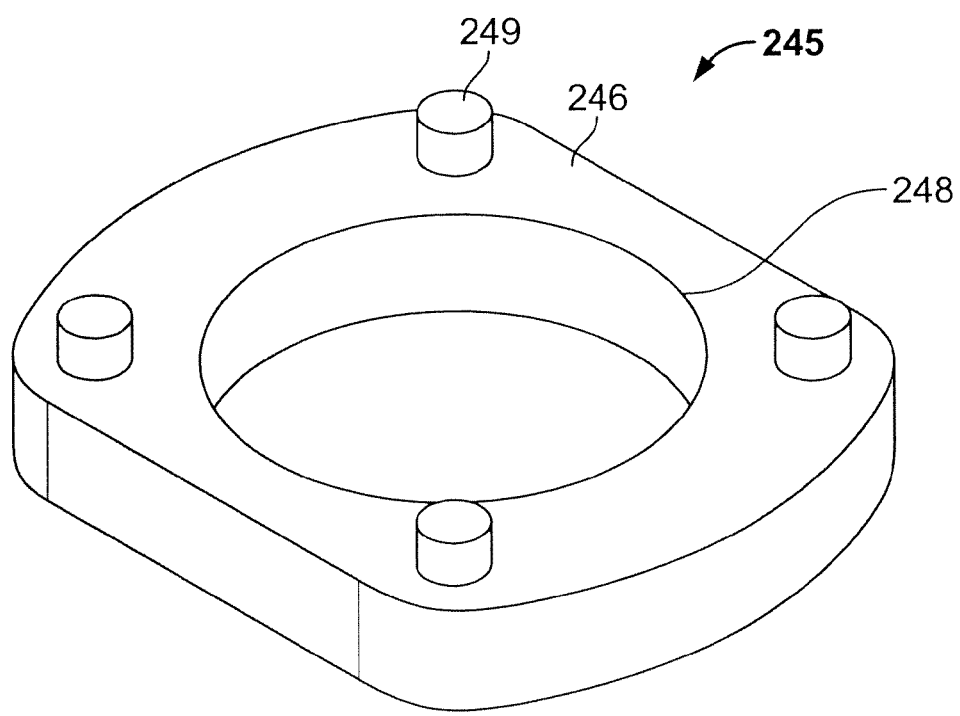
FIG. 25 is a perspective view of an alternative foam ring end cap spring for use with the first cassette unit of FIGS. 1 to 4.

In a further embodiment shown at FIG. 25, a second alternative end-cap spring 245 is constructed from a ring of a resiliently flexible material such as a rubbery, foamed or sponge-like material. Again, whilst the detailed shaping of this second alternative end-cap spring 245 varies from that of the end-cap spring 45 of FIGS. 15a to 15d its essential function is the same. The rear end wall 246 of the alternative end-cap spring 245 defines an essentially flat profile, which allows it to seat up against the inner end wall of the end-cap 40. This alternative end-cap spring is held in place by the interaction of the inner end wall of the end-cap 40 and/or with pegs 249 on the rear end wall of the alternative end-cap spring 245. The body of the end-cap spring comprises a ring of material arranged about a central ring aperture 248. Within the cassette unit, this ring aperture 248 is sized and shaped to fit about the forward skirt 42 of the end-cap 40 and when the plunger slaving part 60 is engaged with the end-cap 40 (e.g. at a position corresponding to that shown at FIGS. 2 and 13) about the outer circumferential wall 62 of the plunger slaving part 60.

Figure 8A:
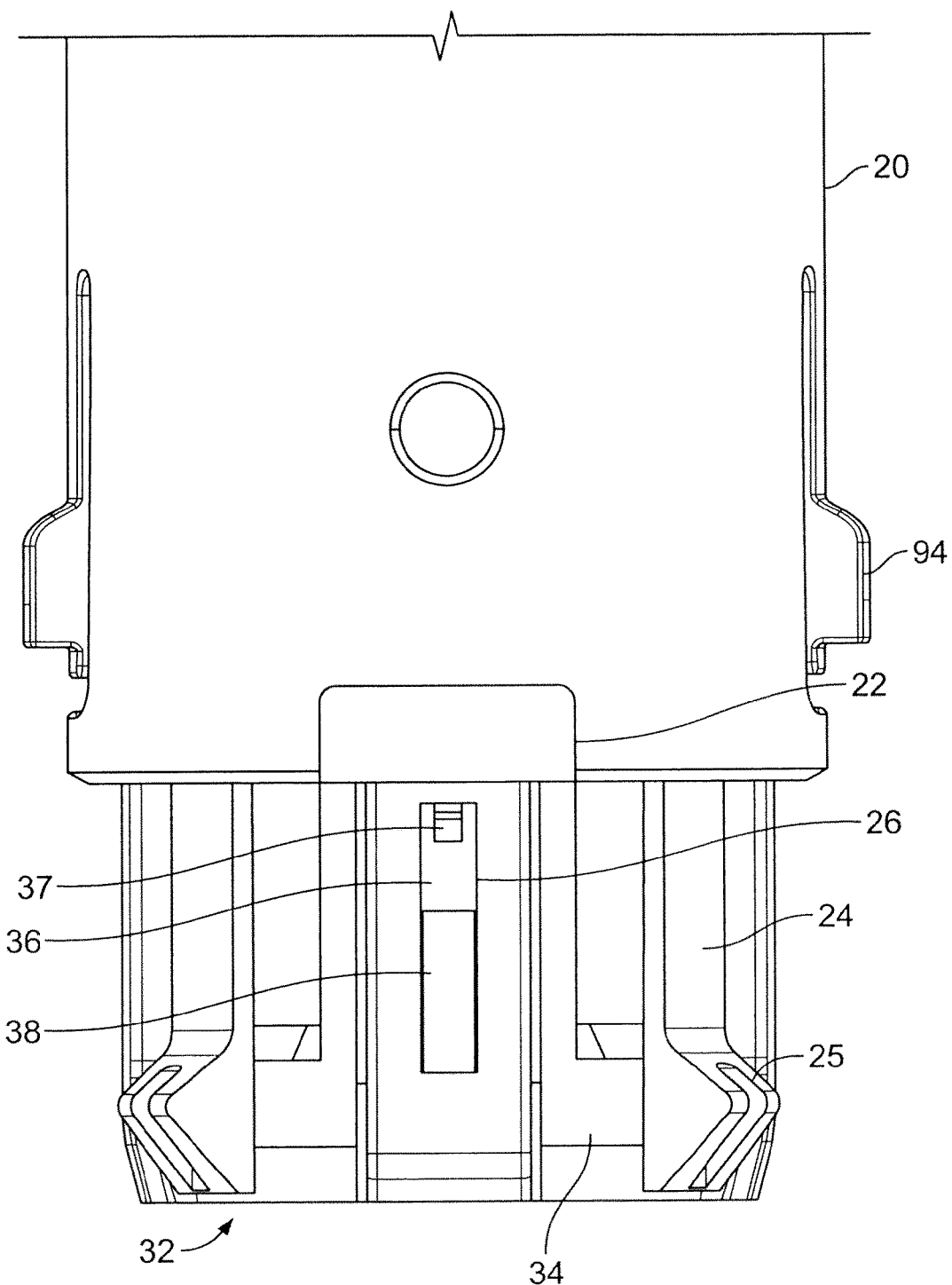
FIGS. 8a and 8b are perspective side-on views of a cassette unit housing and shuttle lock control part-assembly of the first cassette unit of FIGS. 1 to 4 at respective, first 'cassette unused' and third 'cassette used' positions.
Figure 8B:
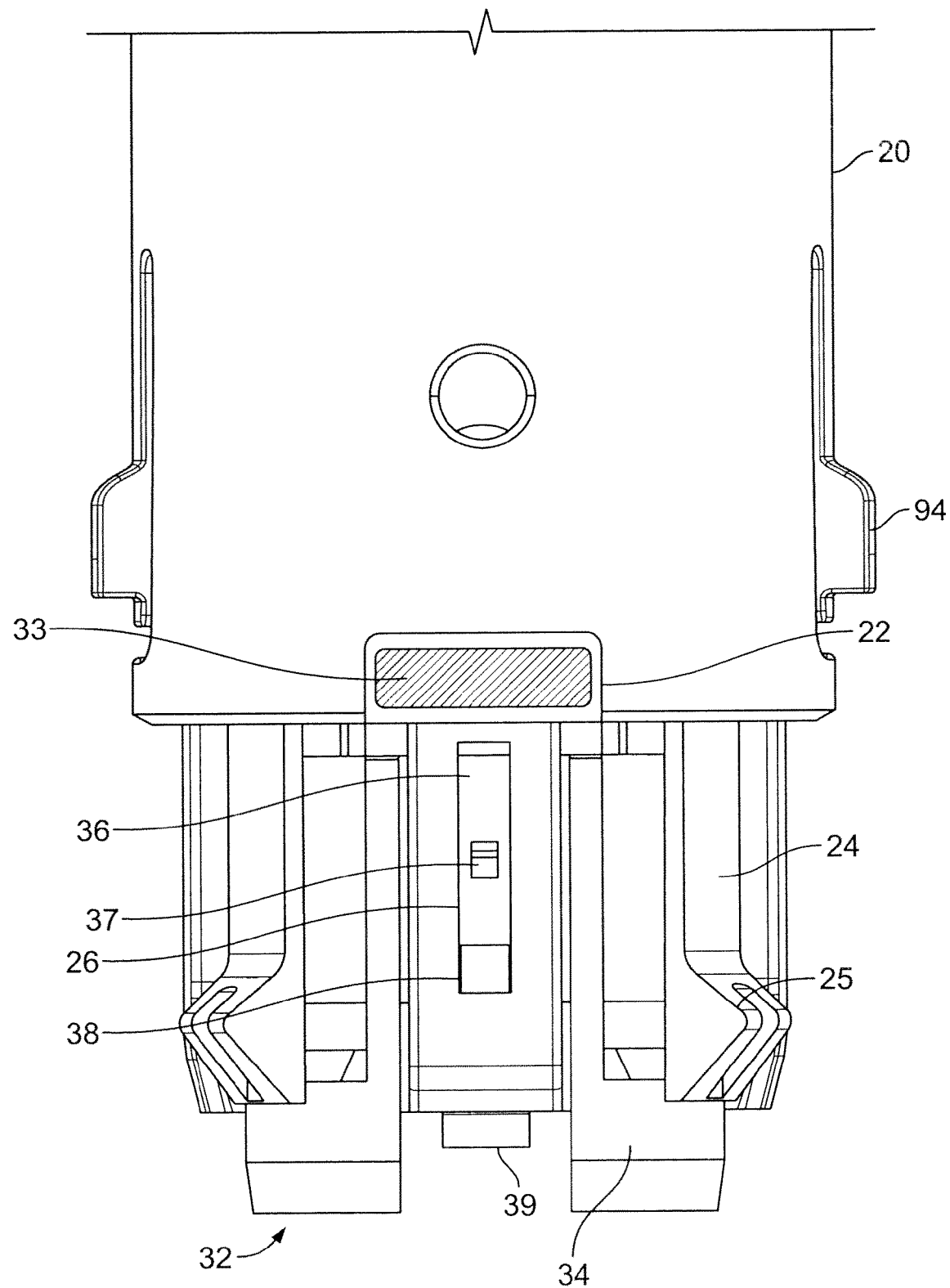
Figure 8C:
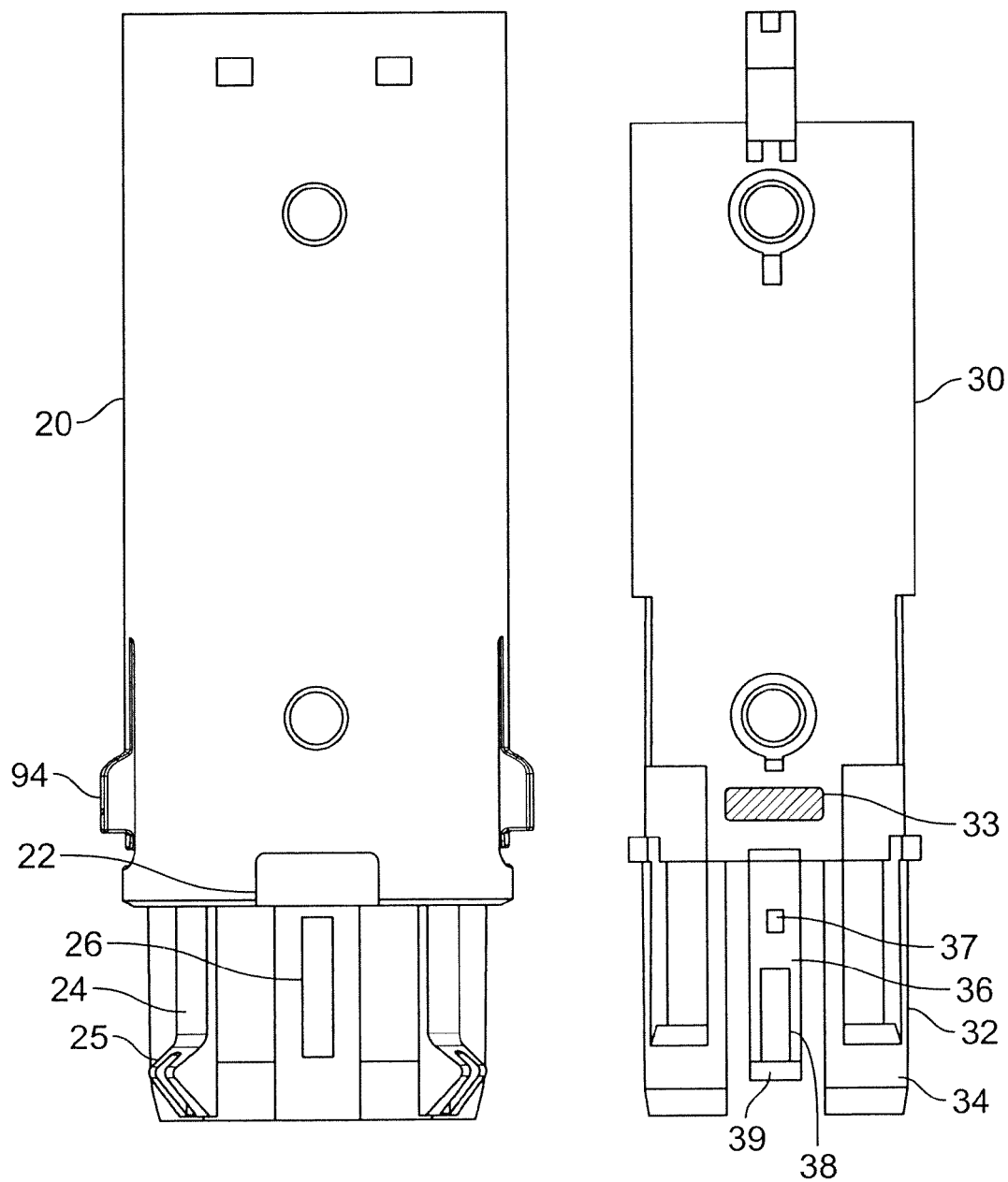
FIG. 8c shows the separate cassette unit housing and shuttle lock control parts of the part-assembly of FIGS. 8a and 8b.

Details of the selective control of cap locking/unlocking of the first cassette unit 1 are now described by reference to FIGS. 8a to 11c. It will be noted that for illustrative purposes only, FIG. 8c shows the separate cassette unit housing 20 and shuttle lock control 32 parts of the part-assembly of FIGS. 8a and 8b.

The cassette unit housing 20 is provided with a radial arrangement of first engagement features in the form of axially protruding locking legs 24 having heels defining angled tips 25 movable by flexing action and arranged for reversibly engaging a corresponding radial arrangement of second engagement features in the form of socket through holes 52 of the removable cap 50 (see FIGS. 3 and 4) for reversible lock engagement of the removable cap 50 to the cassette unit housing 20. In a secondary aspect, this arrangement also acts to prevent rotation of the cap 50 relative to the cassette unit housing 20.

The inner housing sleeve 30 defines a shuttle lock control feature 32 comprising a radial arrangement of blocking elements 34 for selectively blocking inwardly flexing movement of the movable locking legs 24 of the cassette unit housing 20 relative to the socket holes 52 of the cap 50, thereby providing for selective control of cap locking/unlocking.

Figure 9A:
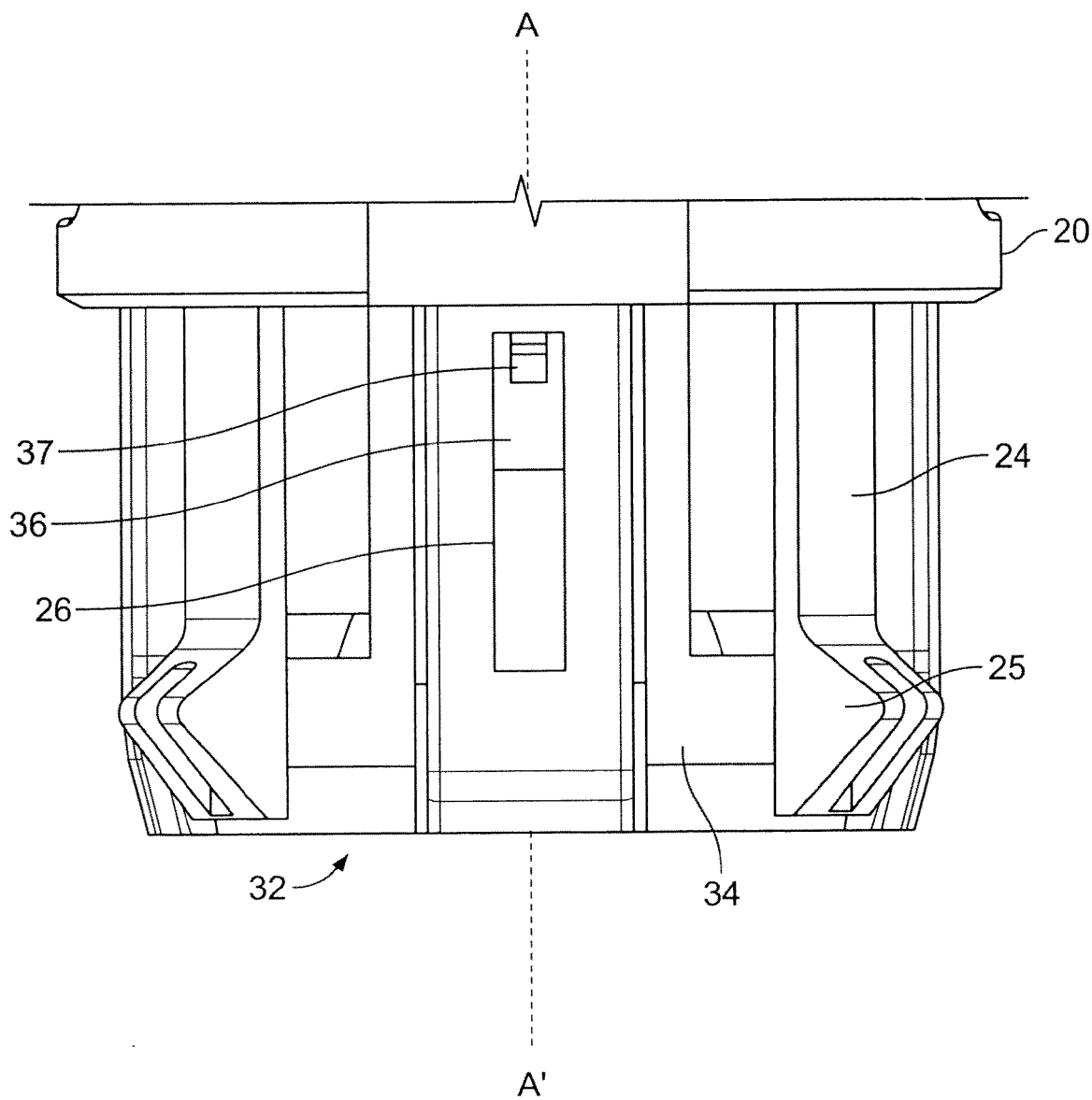
FIGS. 9a to 9c are close-up perspective side-on views of the cassette unit housing and shuttle lock control part-assembly of FIGS. 8a and 8b at respective, first 'cassette unused', second 'cassette unlocked' and third 'cassette used' positions.
Figure 9B:
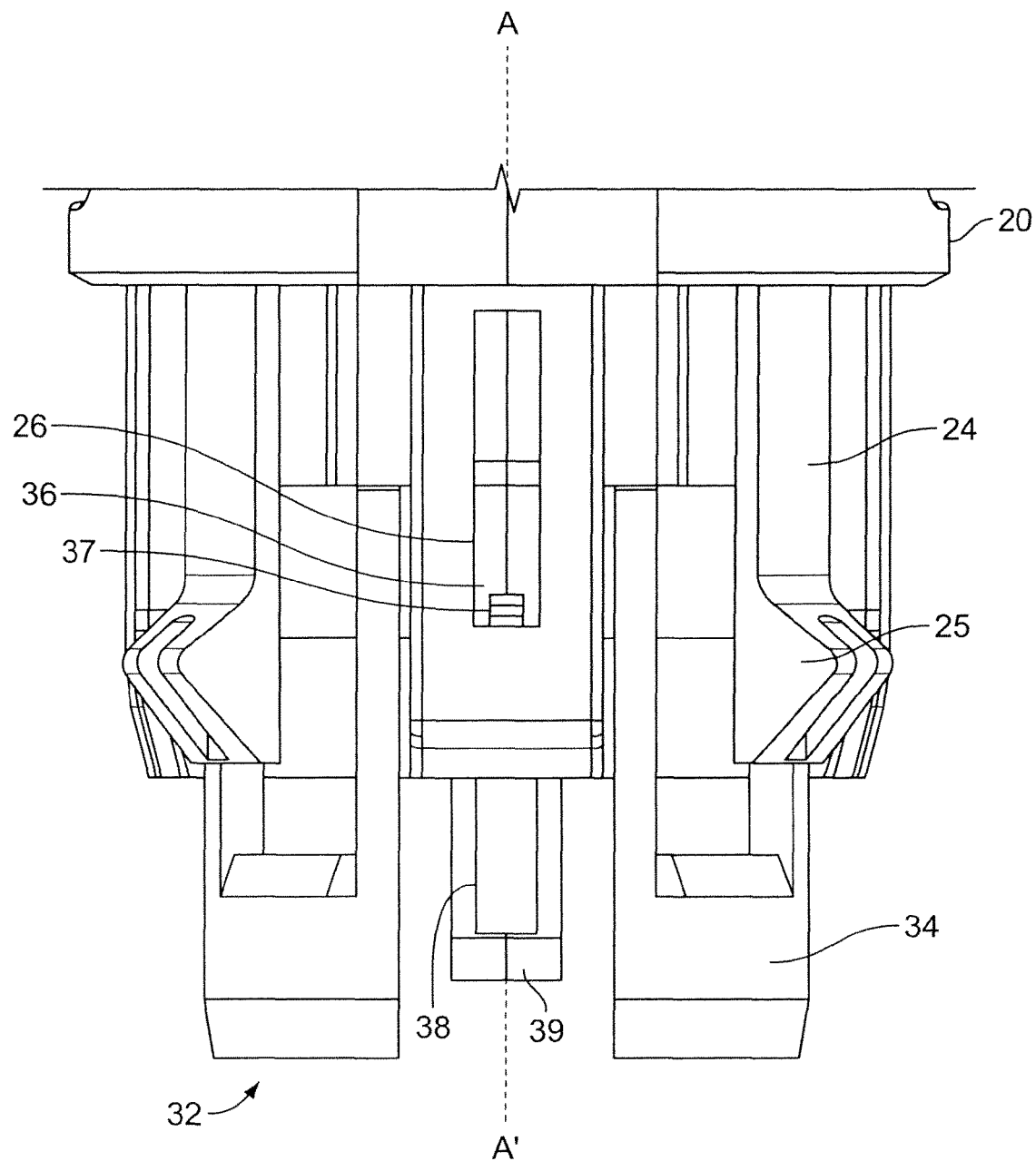
Figure 9C:
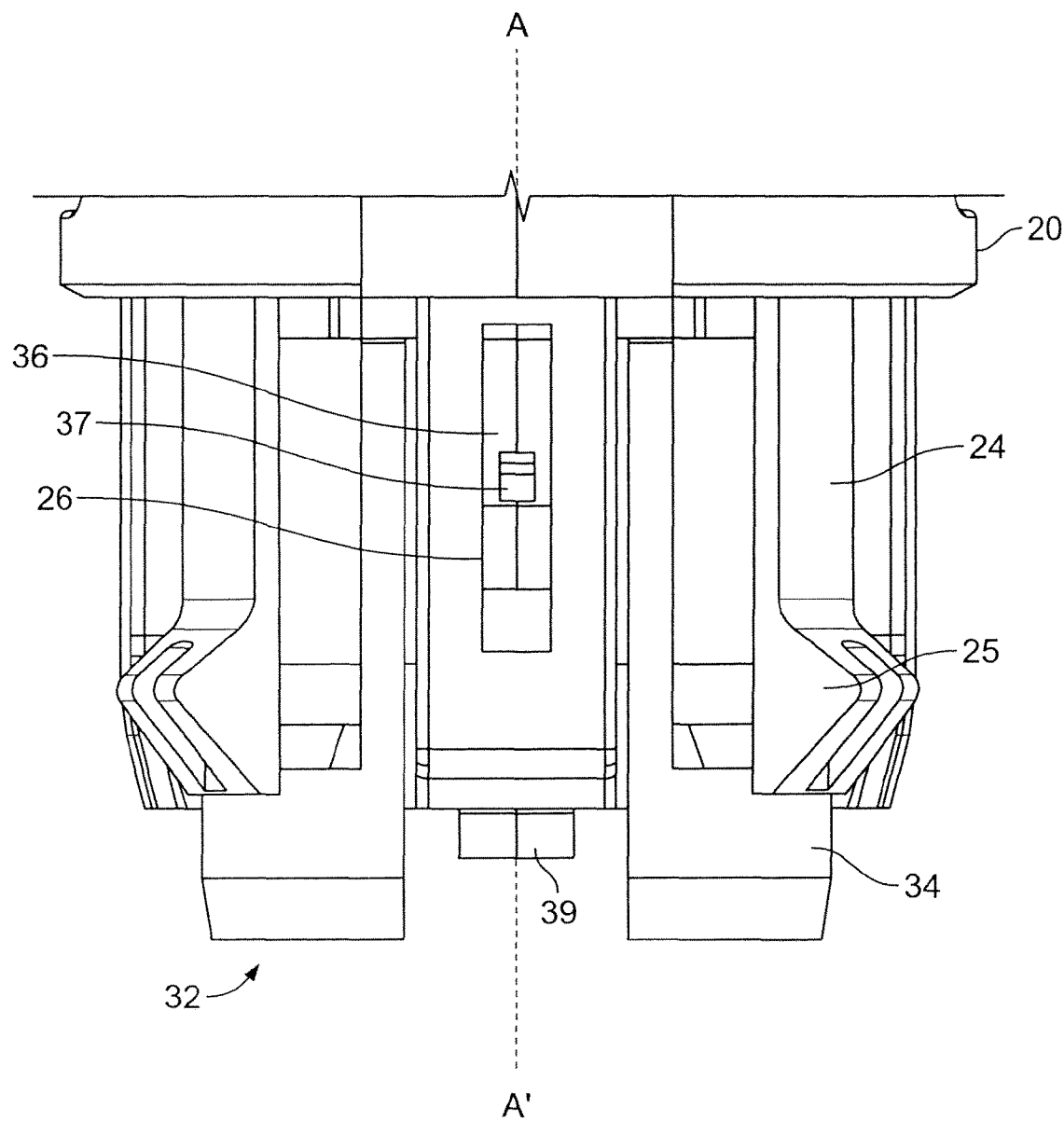
Figure 10A:
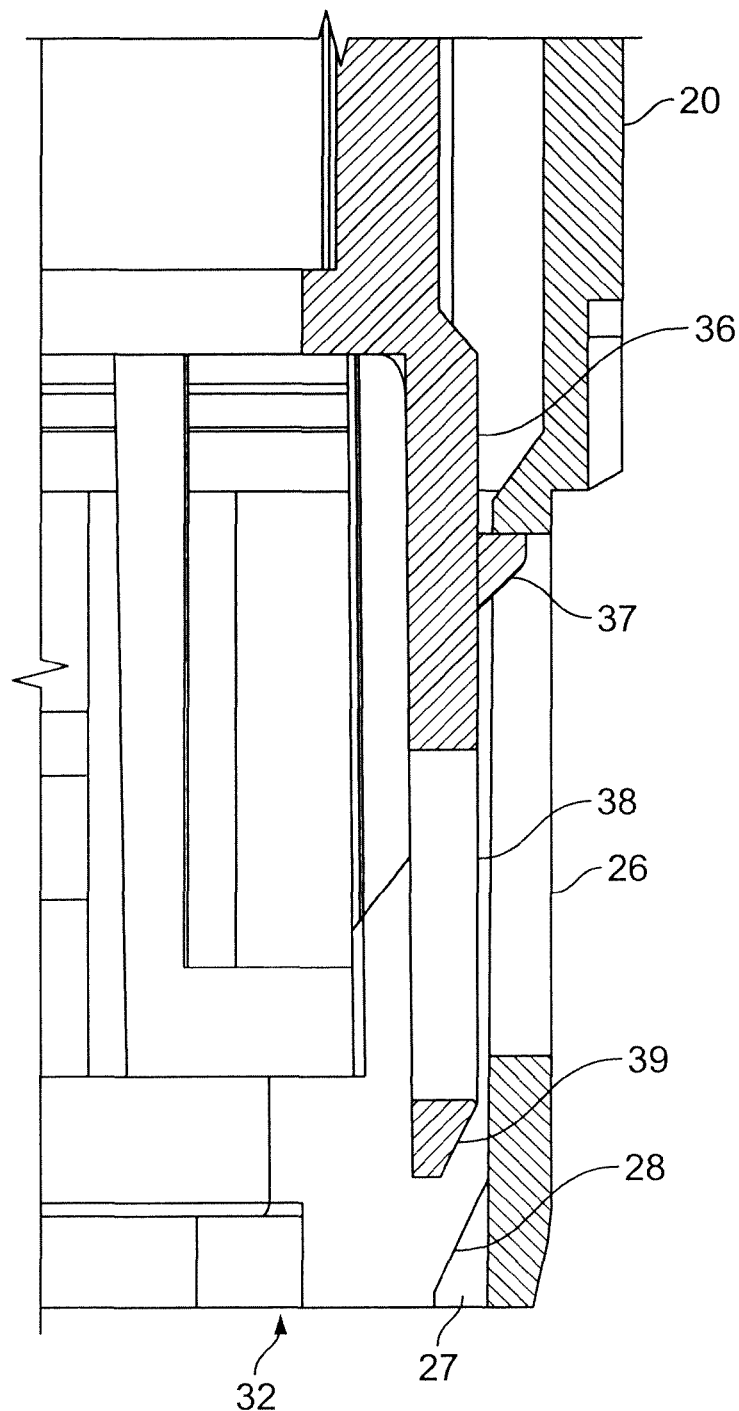
FIGS. 10a to 10c are sectional views taken along the line A-A' of FIGS. 9a to 9c of the cassette unit housing and shuttle lock control part-assembly of FIGS. 8a and 8b at respective, first 'cassette unused', second 'cassette unlocked' and third 'cassette used' positions.
Figure 10B:
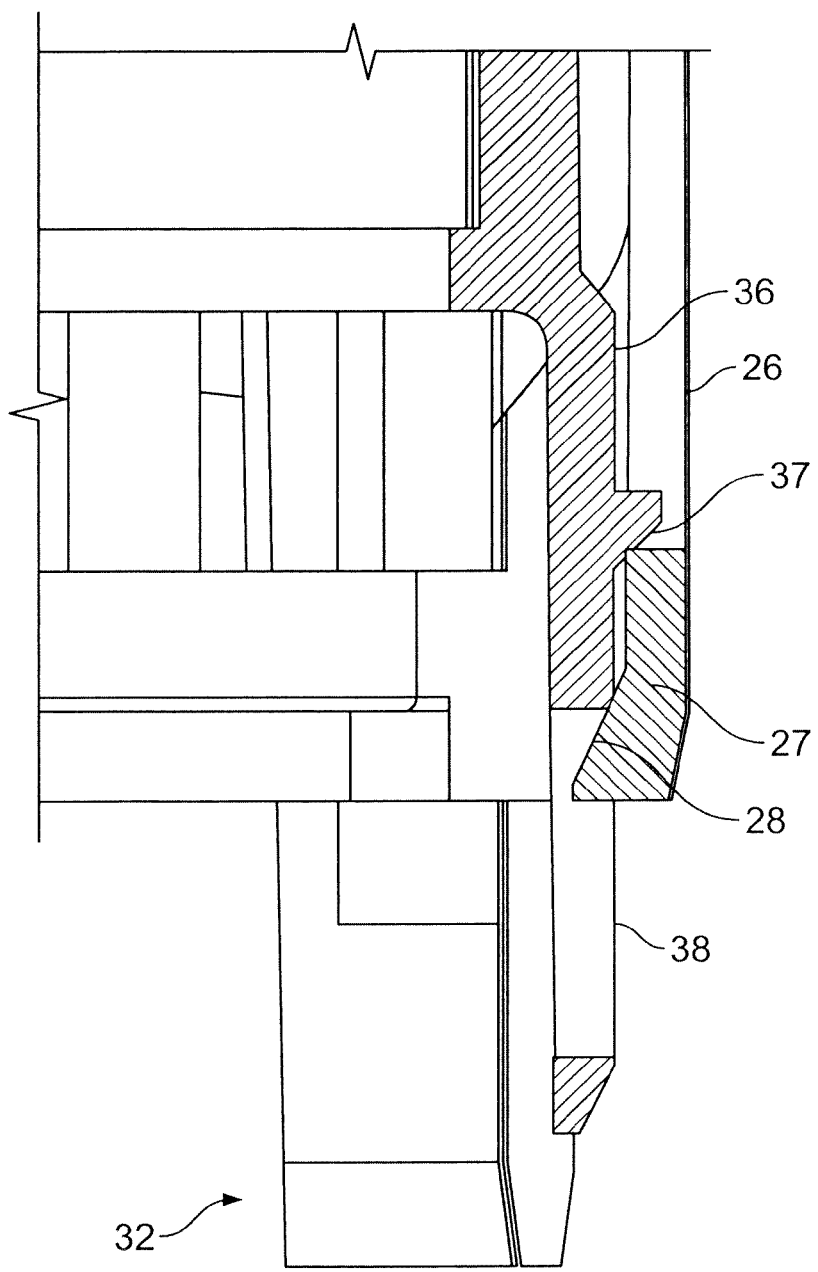
Figure 10C:
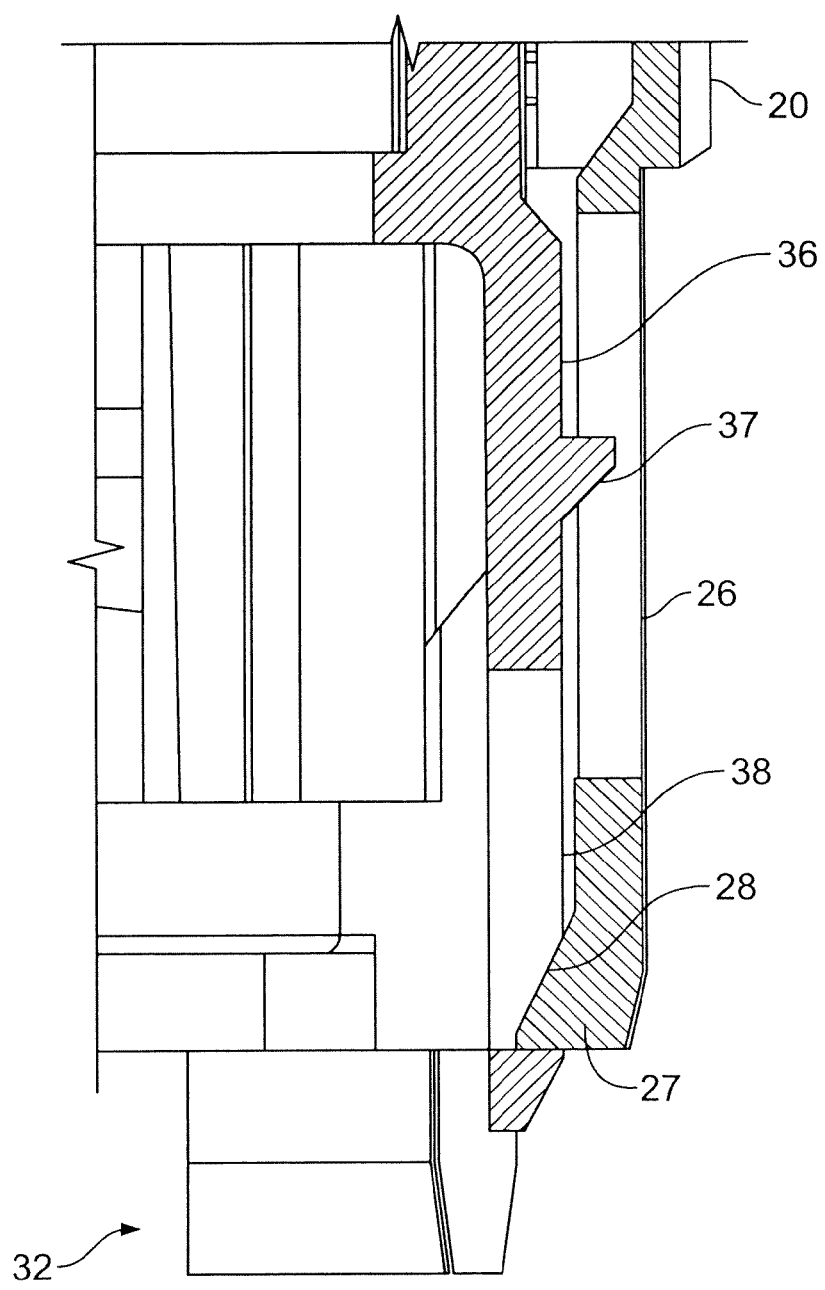
Figure 11A:
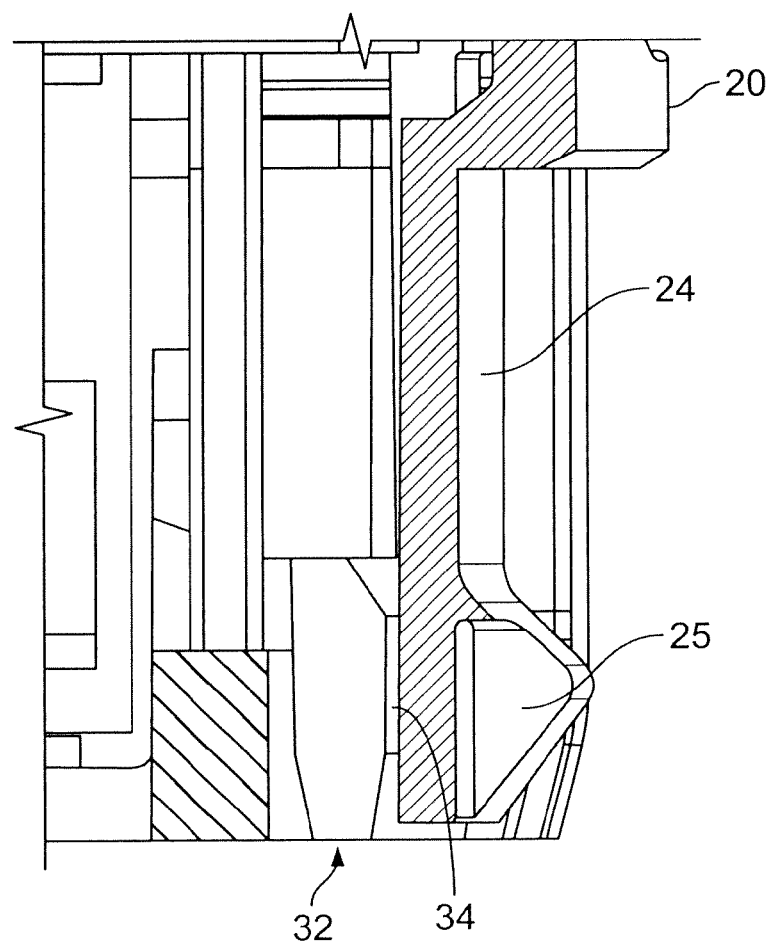
FIGS. 11a to 11c are sectional views taken along the plane bisecting locking arm 24 of FIGS. 9a to 9c of the cassette unit housing and shuttle lock control part-assembly of FIGS. 8a and 8b at respective, first 'cassette unused', second 'cassette unlocked' and third 'cassette used' positions.
Figure 11B:
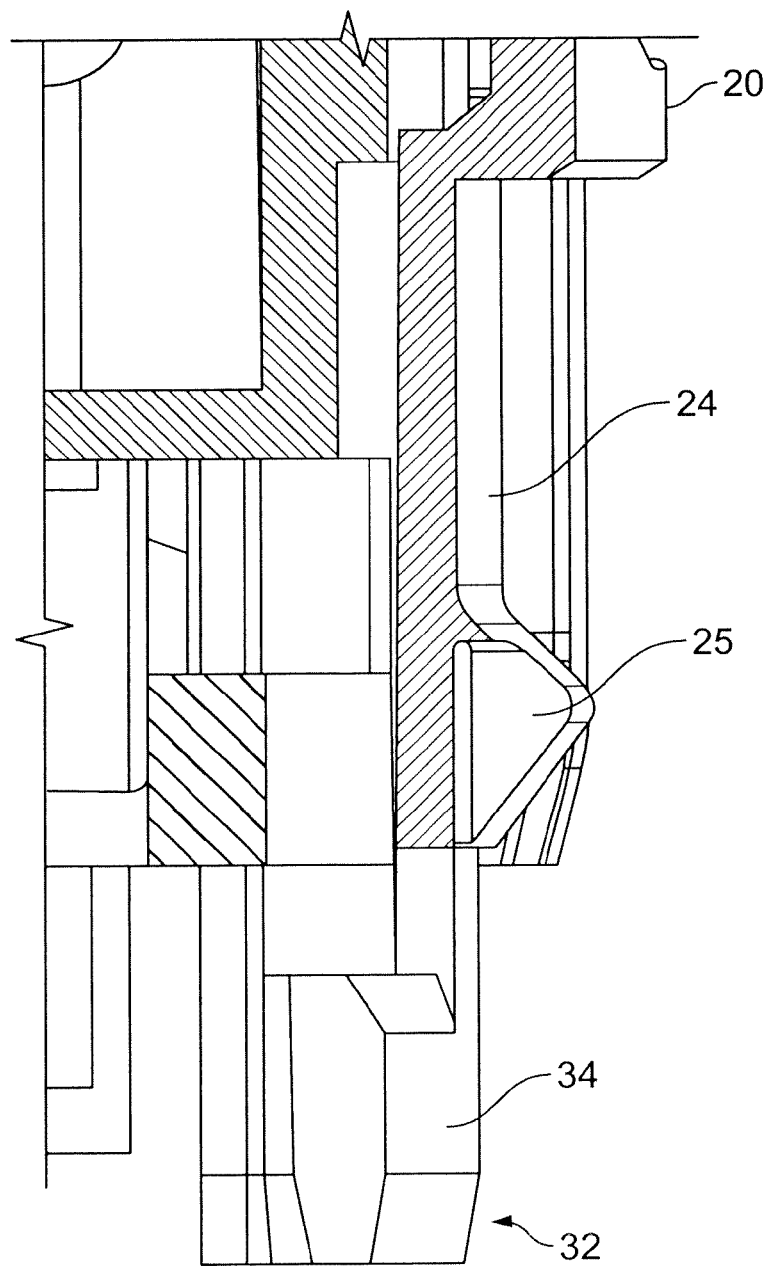
Figure 11C:
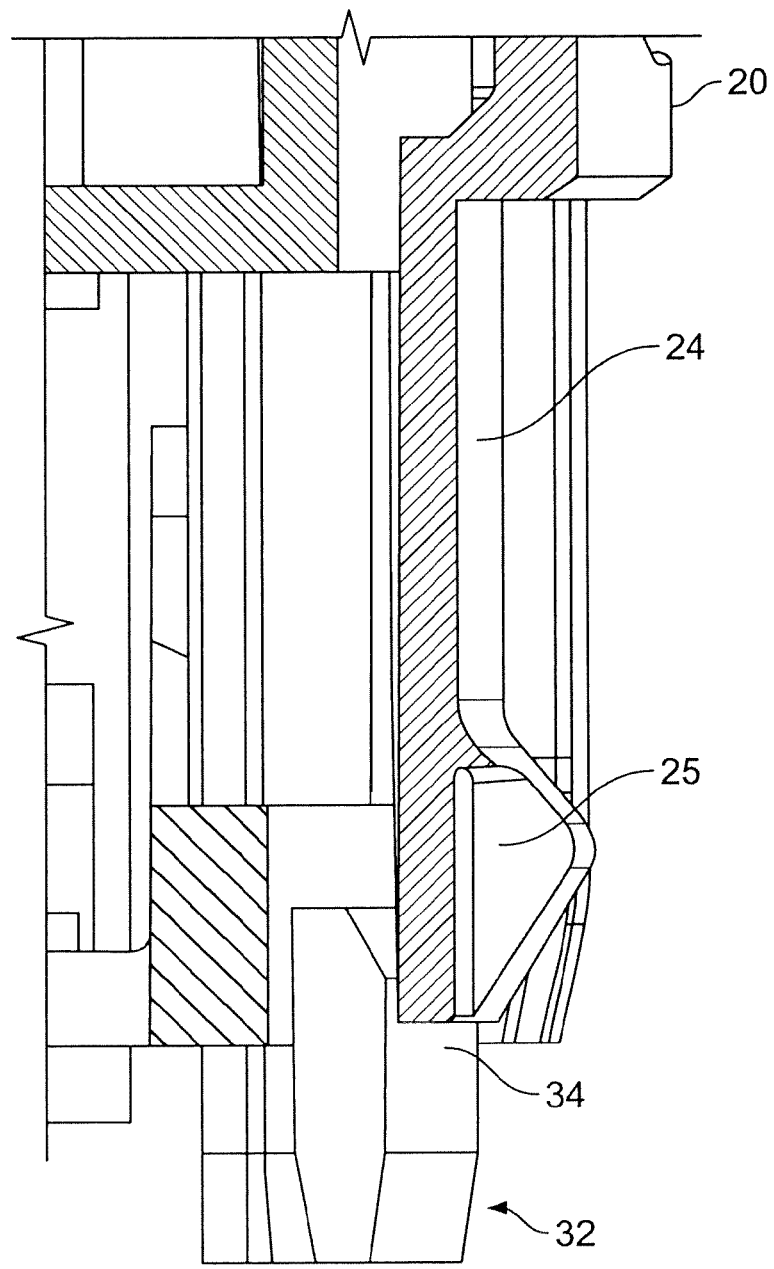
Figure 12:
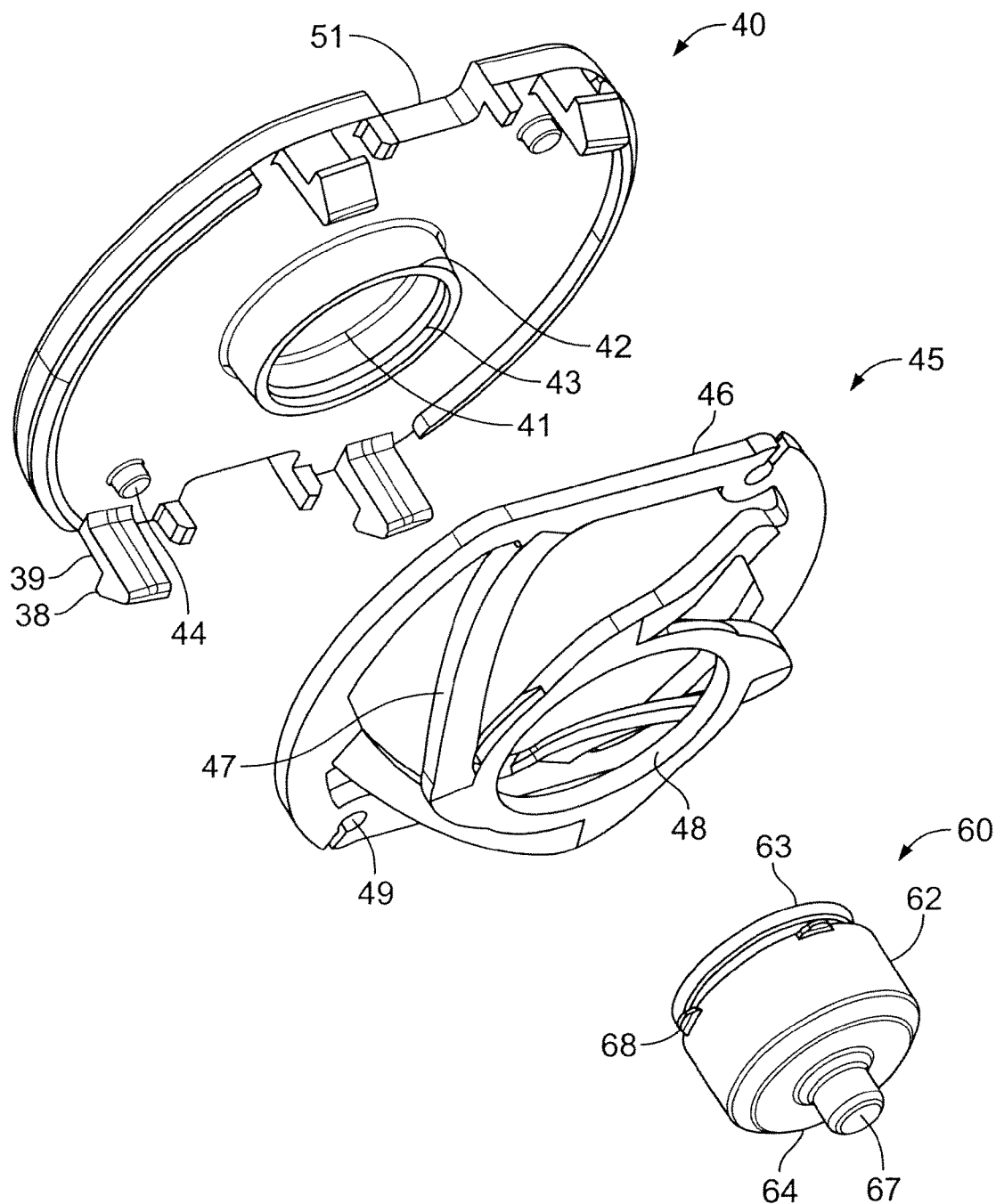
FIG. 12 is a perspective exploded view of an end cap, end cap spring and plunger slaving part for use with the first cassette unit of FIGS. 1 to 4

The shuttle lock control 32 is axially movable relative to the cassette unit housing 20 in between three positions, namely:

(i) as shown at FIGS. 8a, 9a, 10a and 11a, a first 'cassette unused' position, in which the blocking elements 34 block movement of the locking legs 24 of the cassette unit housing 20 relative to the socket through holes 52 of the removable cap, thereby keeping the removable cap 50 in locked relationship to the cassette unit housing 20;

(ii) as shown at FIGS. 9b, 10b and 11b, a second 'cassette unlocked' position, in which the blocking elements 34 no longer block movement of the locking legs 24 of the cassette unit housing 20 relative to relative to the socket through holes 52 of the removable cap 50, thereby allowing for unlocking of the removable cap 50 from the cassette unit housing 20 and for removal and replacement thereof; and (iii) as shown at FIGS. 8b, 9c, 10c and 11c, after replacement of the removable cap 50, a third 'cassette used' position, locating intermediate the first and second positions, in which the blocking elements 34 again block movement of the locking legs 24 of the cassette unit housing 20 relative to the socket through holes 52 of the removable cap, thereby restoring the locked relationship between the removable cap 50 and the cassette unit housing 20.

Movement of the shuttle lock control 32 is typically achieved by application of forward pushing force to the top of the protruding arms 31 of inner housing sleeve 30 to push the inner housing sleeve 30 and the shuttle lock control 32 forward. This is typically achieved by insertion of a pushing member (e.g. a pin) into each of the cut-away apertures 51 of the cassette unit end cap 40 to push forward the protruding arms 31 of the inner housing sleeve 30.

The shuttle lock 32 is biased by the action of shuttle lock spring 35 from the second position to the third position.

Thus, in a typical use operation, on removal of the removable cap 34 the shuttle lock 32 is in the second position; during use of the cassette for injection the shuttle lock 32 is biased into the third position; and during replacement of the removable cap 50 the shuttle lock is in the second position.

The shuttle lock control 32 is further provided with a pair of diametrically oppositely located axial position locators 36, each of which is arranged to define three distinct axial positions of the shuttle lock control 32 relative to cassette unit housing 20 and corresponding to said first, second and third positions. Each axial position locator 36 comprises an axial protrusion having a follower 37 arranged thereon for receipt within a corresponding axial track 26 of the inner cassette unit housing 20 such as to define an axial track-follower relationship between the shuttle lock control 32/inner housing sleeve and the cassette unit housing 20. The previously defined first and second positions correspond to the opposite extremes of this axial track-follower relationship.

In a further structural detail, and with particular reference to FIGS. 10a to 10c, each axial position locator 36 further comprises a first latch element in the form of an axial latching slot 38 arranged for selective latching relationship with a corresponding second latch element in the form of a latching foot 27 of the cassette unit housing 20. The latching foot 27 of the cassette unit housing 20 is movable within the axial latching slot 38 of the axial position locator 36 such as to define an axial foot-in-slot relationship between these parts.

As shown at FIG. 10a, in the first position the axial latching slot 38 and latching foot 27 are in non-latching relationship and as shown at FIGS. 10b and 10c respectively, in the second and third positions the axial latching slot 38 and latching foot 27 are in latching relationship, wherein the second (FIG. 10b) and third (FIG. 10c) positions respectively correspond to opposing slot ends of said axial latching slot 38.

A non-return feature is also provided and arranged such that when the first and second latch elements 38, 27 have come into latching relationship return to a non-latching relationship is prevented. Thus, a forward ramped surface 39 is provided at the forward end of the first latch element, in which the axial latching slot 38 is defined, and a corresponding ramped surface 28 is defined at latching foot 27 such as to facilitate ramping over each other when coming into latching relationship. However, once the latching foot 27 has been received within the axial latching slot 38 (second and third positions, see FIGS. 10b and 10c) it is retained there and may not return to the first position (FIG. 10a).

In use, the cassette unit 1 is initially in the first 'cassette unused' position, in which the angled tip 25 of each flexibly resilient locking leg 24 of the cassette unit housing 20 protrudes slightly into a socket through-hole first engagement feature 52 of the removable cap 50. It will be appreciated that this engaging interaction of the angled tip 25 of locking leg 24 with socket through-hole feature 52 effectively prevents movement (including rotation) of the cap 50 relative to the cassette unit housing 20. In this first position, the blocking elements 34 block movement of the locking legs 24 of the cassette unit housing 20 relative to the socket through holes 52 of the removable cap, thereby keeping the removable cap 50 in locked relationship to the cassette unit housing 20.

In the second 'cassette unlocked' position, this engaging interaction can be released by pushing each locking leg 24 inwards, thereby clearing the angled tip 25 from engaging relationship with each relevant socket through-hole 52. Such inward pushing action on the locking leg 24 can be achieved (in the cap unlocked position of FIGS. 9b, 10b and 11b) by pulling the cap 50 forwards and away from the cassette unit housing 20, which results in the angled tip 25 interacting with the wall edges of the through-hole 52 to push the locking leg 24 inwards.

After cap removal and during injected use, the action of shuttle lock spring 35 results in adoption of the third position until such time as the removable cap 50 is replaced when the second position is again adopted during cap 50 replacement. After cap replacement, the third position is again adopted. The shuttle lock control 32 is marked with a 'used cassette' flag 33 arranged to be brought into registration with the indicator opening of the cassette unit housing 20 at the third 'cassette used' position (see FIG. 8b) as a visual indicator that the cassette has been used.

An alternative inner housing sleeve 330 with shuttle lock control feature 332 and its interaction with cassette unit housing 20 is now described by reference to FIGS. 26 to 28c. By comparison with FIG. 8c and from the following description, it will be appreciated that the alternative inner housing sleeve is a slight variant of the inner housing sleeve 30 with shuttle lock control 32 described hereinbefore. In general terms, operation and usage of this variant for selective control of cap locking/unlocking of the first cassette unit 1 is as previously described by reference to FIGS. 8a to 11c.

The alternative inner housing sleeve 330 incorporates a safety feature for preventing unintended movement (e.g. of the shuttle lock control 332 part thereof) relative to the cassette unit housing 20, which may potentially arise as a result of impact (e.g. from dropping of the cassette unit 1 or shock impact during transit thereof). In particular, the safety feature prevents unintended downwards movement of the inner housing sleeve 330 relative to the cassette unit housing 20 against the shuttle lock spring 35 from the first 'cassette unused' position to the third 'cassette used' position. This safety feature thereby prevents the 'used cassette' flag 333 of the inner housing sleeve from being moved in unintended fashion into registration with the indicator opening of the cassette unit housing 20, which would give a false visual indicator that the cassette 1 has been used.

Figure 26:
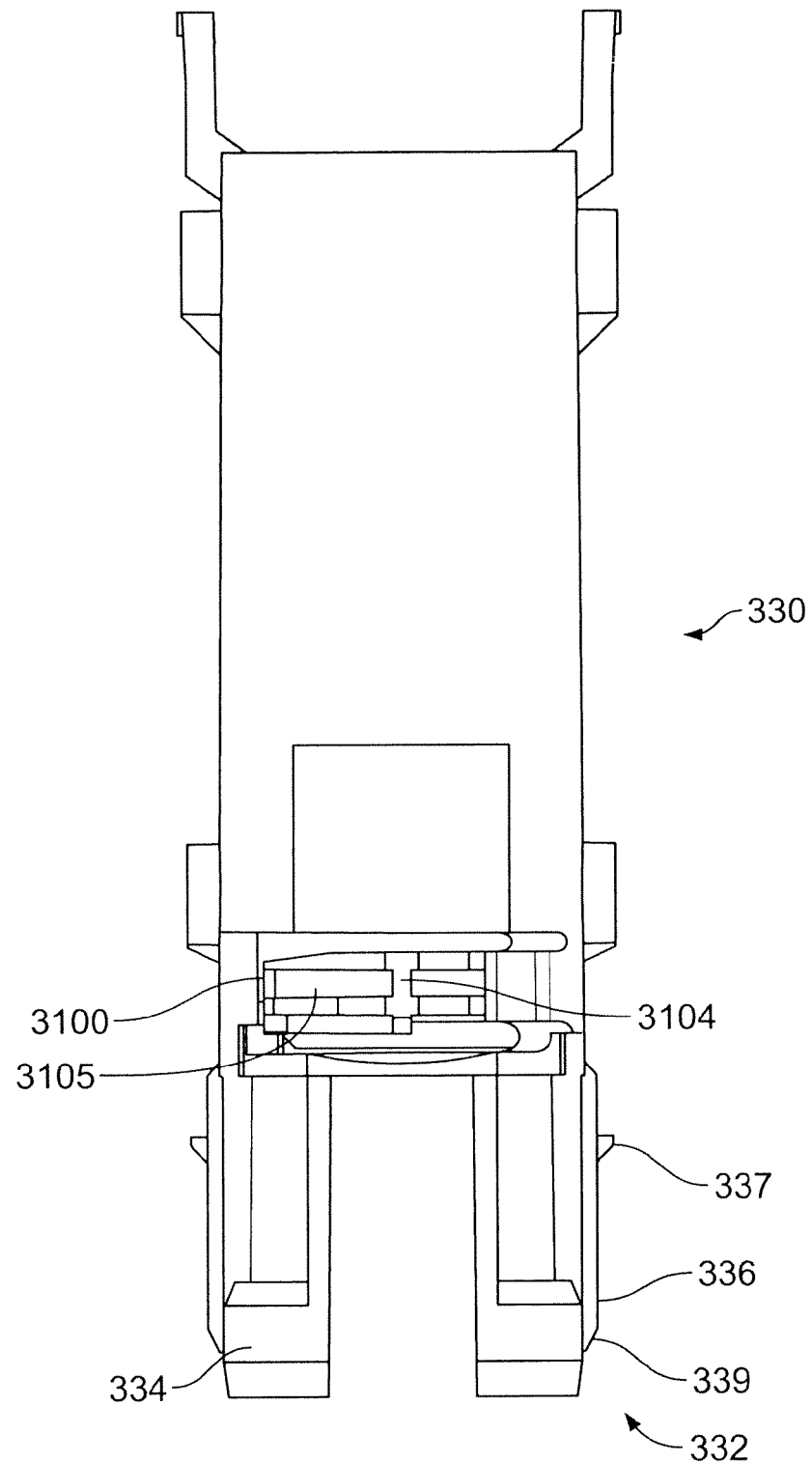
FIG. 26 a perspective side view an alternative shuttle lock control part suitable for use with the cassette unit housing of the part-assembly of FIGS. 8a and 8b.
Figure 27:
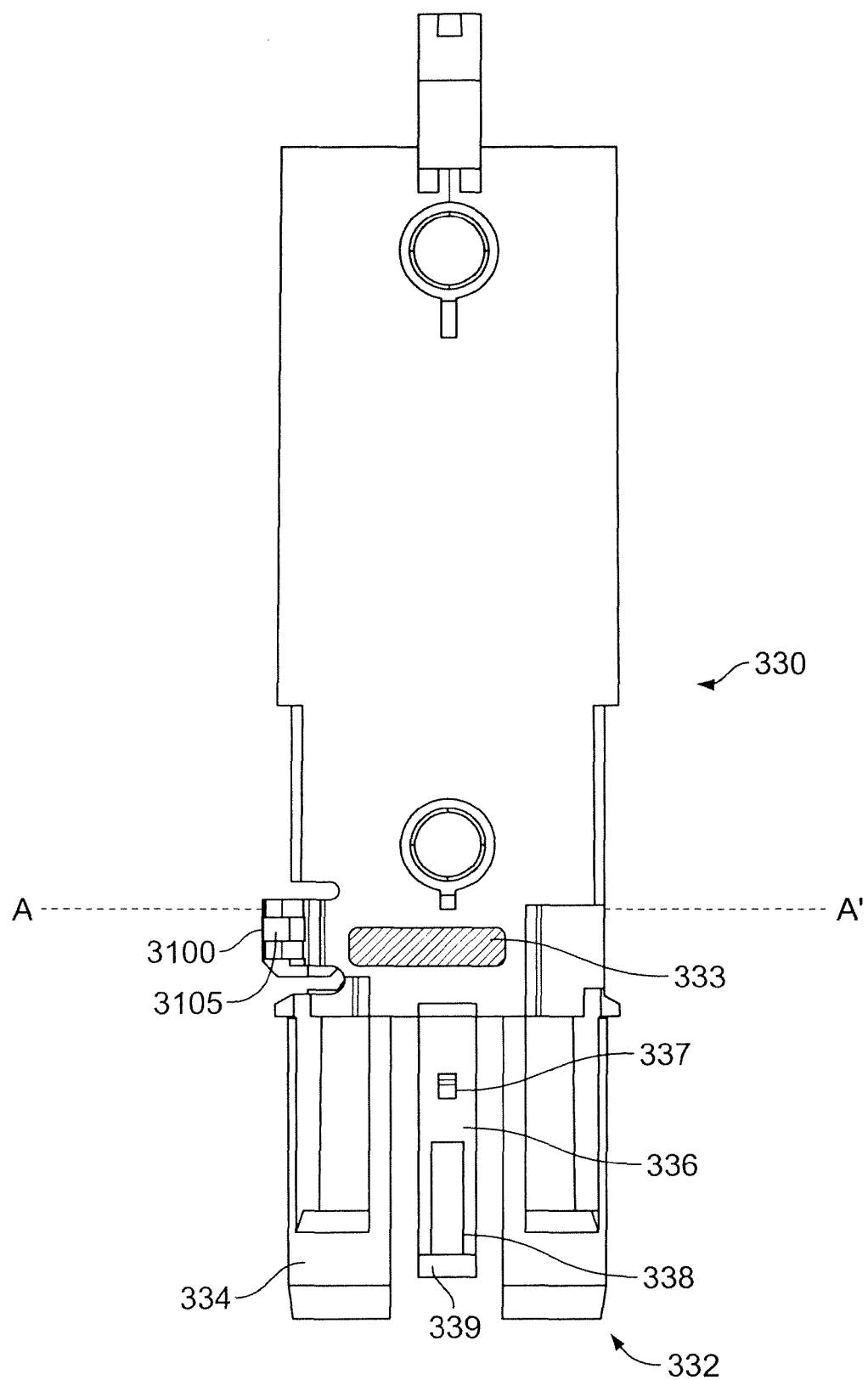
FIG. 27 an alternative perspective side view rotated by 90° relative to that of FIG. 26 of the alternative shuttle lock control part of FIG. 26.

FIGS. 26 and 27 show views of the alternative inner housing sleeve 330 with its 'used cassette' flag 333. In common with the inner housing sleeve 30 of FIGS. 8a to 11c, the alternative housing sleeve defines a shuttle lock control feature 332 comprising a radial arrangement of blocking elements 334 for selectively blocking inwardly flexing movement of the movable locking legs 24 of the cassette unit housing 20 relative to the socket holes 52 of the cap 50, thereby providing for selective control of cap locking/unlocking.

Again in common with the inner housing sleeve 30 of FIGS. 8a to 11c, the shuttle lock control 332 is provided with a pair of diametrically oppositely located axial position locators 336, each of which is arranged to define three distinct axial positions of the shuttle lock control 332 relative to cassette unit housing 20 and corresponding to said first, second and third positions. Each axial position locator 336 comprises an axial protrusion having a follower 337 arranged thereon for receipt within a corresponding axial track 26 of the inner cassette unit housing 20 such as to define an axial track-follower relationship between the shuttle lock control 32/inner housing sleeve and the cassette unit housing. The previously defined first and second positions correspond to the opposite extremes of this axial track-follower relationship.

In a further structural detail, each axial position locator 336 of the alternative inner housing sleeve 330 further comprises a first latch element in the form of an axial latching slot 338 arranged for selective latching relationship with a corresponding second latch element in the form of a latching foot 27 of the cassette unit housing 20. The latching foot 27 of the cassette unit housing 20 is movable within the axial latching slot 338 of the axial position locator 336 such as to define an axial foot-in-slot relationship between these parts. A non-return feature is also provided and arranged such that when the first and second latch elements 338, 27 have come into latching relationship return to a non-latching relationship is prevented. Thus, a forward ramped surface 339 is provided at the forward end of the first latch element, in which the axial latching slot 338 is defined, and a corresponding ramped surface 28 is defined at latching foot 27 such as to facilitate ramping over each other when coming into latching relationship. It will be appreciated that the interaction of axial position locator 336, axial latching slot 338 and forward ramped surface with corresponding parts 27, 28 of the cassette unit housing 20 is as described previously with particular reference to FIGS. 10a to 10c. The alternative inner housing sleeve 330 further includes a flexible latching arm 3100 arranged for selective safety latching action with part of the inner cassette unit housing 20, which safety latching action is now described by particular reference to FIGS. 28a to 28c.

Figure 28A:
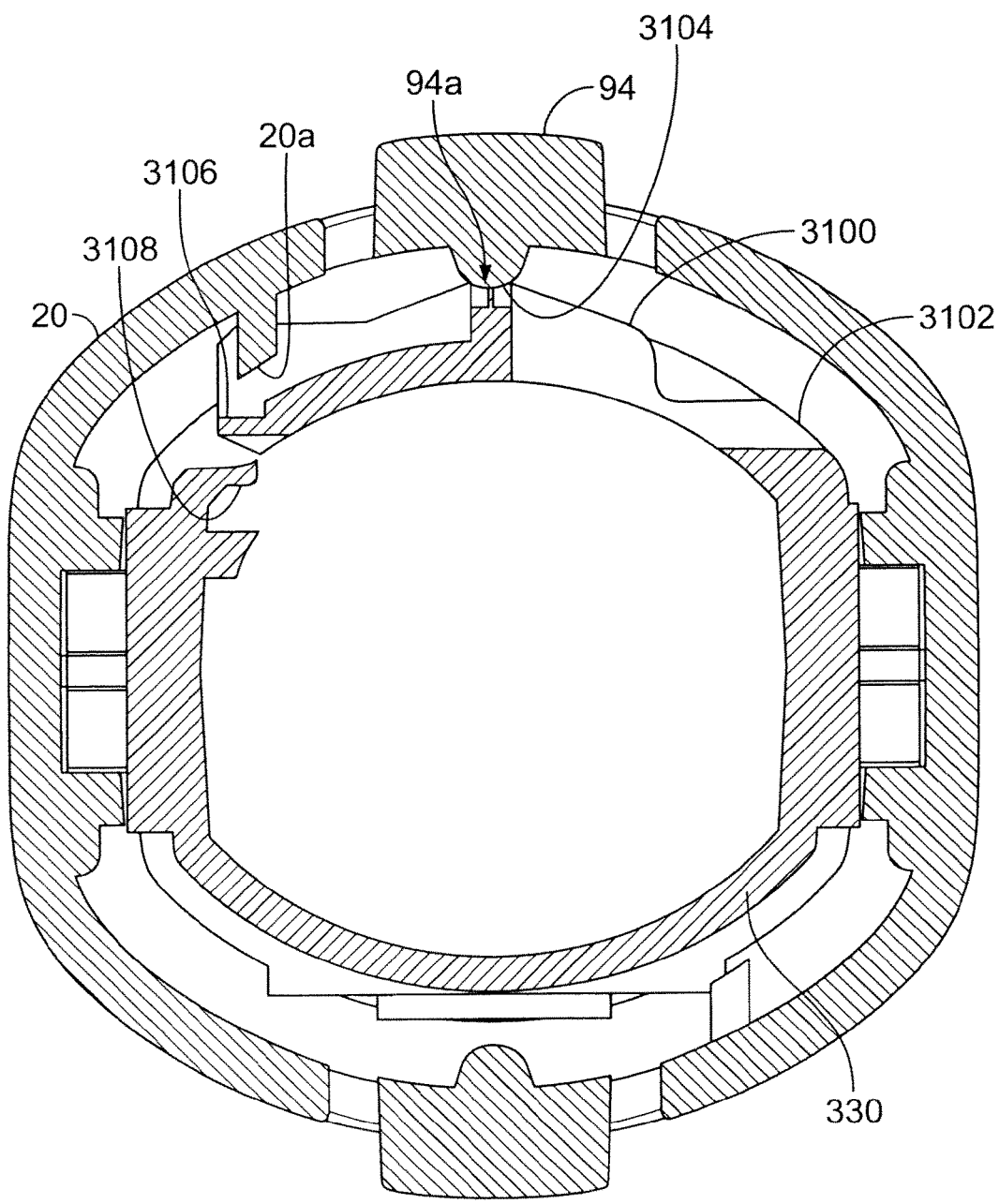
FIGS. 28a to 28c show sectional views along axis A-A' of FIG. 27 showing sequential steps in the interaction of alternative shuttle control lock of FIGS. 26 and 27 with the cassette unit housing of the part-assembly of FIGS. 8a and 8b.
Figure 28B:
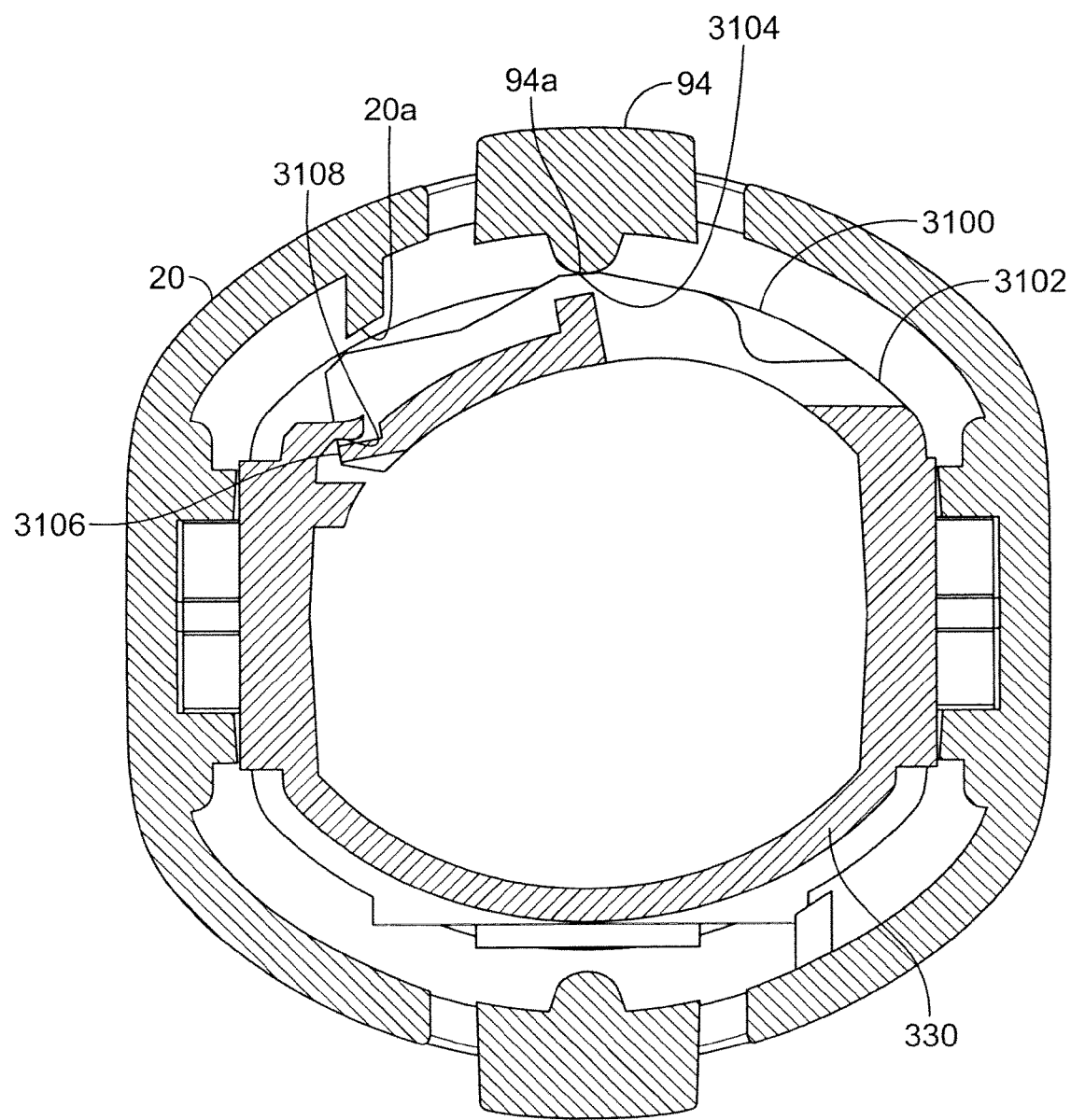
Figure 28C:
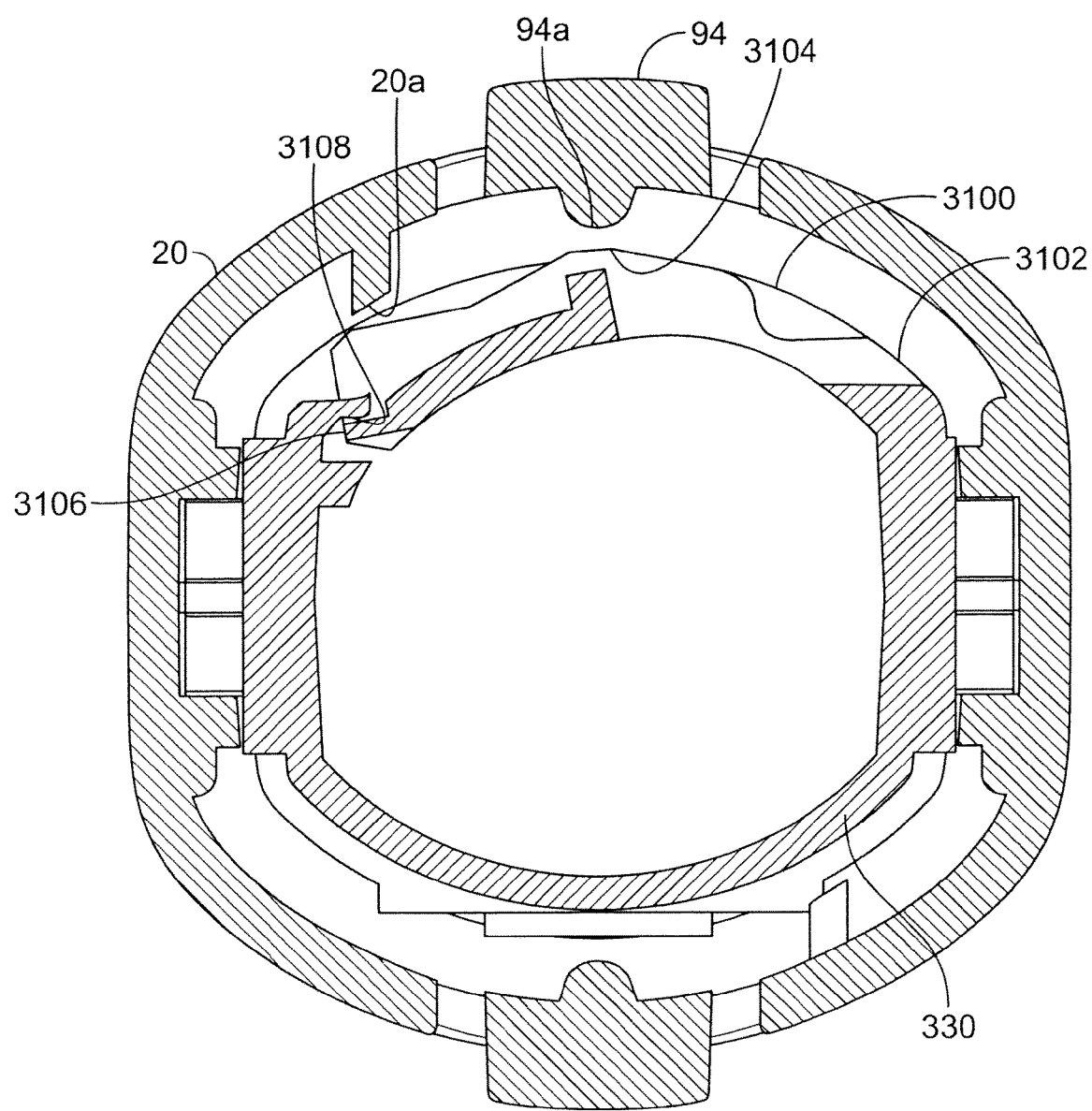

With reference to FIGS. 28a to 28c, the flexible latching arm 3100 is hinged at hinge point 3102 such that it may move within the horizontal plane (i.e. the plane of the printed page). Raised central portion 3104 of the latching arm 3100 is arranged for push-receiving interaction with inwardly protruding nib 94a of flexible locking arms 94 of cassette unit housing 20. Slot-form cavity 3105 (see also FIGS. 26 and 27) is arranged for safety locking interaction with inner safety locking protrusion 20a of cassette unit housing 20. Far end of flexible latching arm 3100 is provided with finger 3106 arranged for non-return latching action with catch 3108.

FIG. 28a shows the latching arm 3100 in the 'pre use' position, in which the raised central portion 3104 thereof rests up against inwardly protruding nib 94a of flexible locking arms 94 of cassette unit housing 20, and in which end finger 3106 is spaced from (and therefore not in latching engagement with) catch 3108. In this 'pre use' position, inner safety locking protrusion 20a of cassette unit housing 20 is in safety blocking interaction with the proximal rib 3105 of the flexible latching arm 3100. Unintended movement (e.g. as a result of shock arising from dropping the cassette unit 1) of the alternative inner housing sleeve 330 relative to the cassette unit housing 20 is thereby, prevented.

Release of the safety blocking interaction of protrusion 20a with proximal rib 3105 is arranged to occur as a result of inward pushing interaction of the flexible locking arm 94 of the cassette unit housing 20 with the raised central portion 3104 of the flexible latching arm 3100, which happens only when the cassette unit 1 is inserted into cassette unit holder 75 of drive unit 70 (as described in more detail hereinafter with particular reference to FIGS. 23a to 23c).

FIG. 28b shows the latching arm 3100 in the intermediate 'safety latch releasing' position, in which inwardly protruding nib 94a of flexible locking arm 94 of cassette unit housing 20 has been pushed in (as the cassette unit 1 is inserted into cassette unit holder 75 of drive unit 70) and is accordingly pushed up against raised central portion 3104 of the flexible latching arm 3100. The flexible latching arm 3100 therefore flexes inwards (i) to move end finger 3106 into non-return latching engagement with catch 3108; and (ii) to move inner safety latching protrusion 20a of cassette unit housing 20 out of safety blocking interaction with proximal rib 3105 of the flexible latching arm 3100. Movement of the alternative inner housing sleeve 330 relative to the cassette unit housing 20 is as a result now possible.

FIG. 28c shows the latching arm 3100 in the 'safety latch released' position, in which (i) end finger 3106 is in non-return latching engagement with catch 3108; and (ii) inner safety latching protrusion 20a of cassette unit housing 20 is not in safety blocking interaction with proximal rib 3105 of the flexible latching arm 3100. Movement of the alternative inner housing sleeve 330 relative to the cassette unit housing 20 is as a result now possible. In this position, inwardly protruding nib 94a of flexible locking arm 94 of cassette unit housing 20 has flexed outwards again (with the cassette unit 1 now fully inserted into cassette unit holder 75 of drive unit 70, as per FIG. 23c) and is accordingly spaced from raised central portion 3104 of the flexible latching arm 3100.

The cassette unit 1 further comprises flexible locking arms 94 for locking receipt within locking apertures 96 of a cassette unit holder 75 of a drive unit, as will be described hereinafter.

Figure 17:
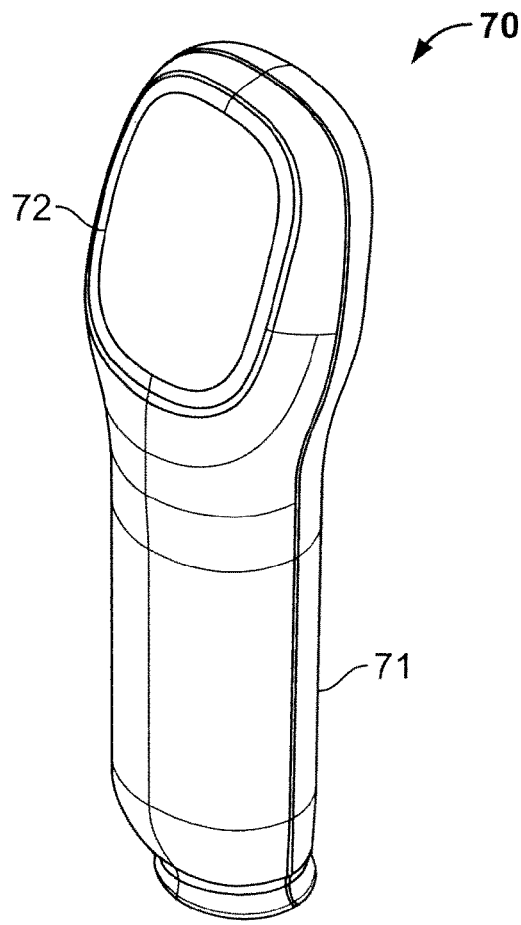
FIG. 17 is a perspective view of a first drive unit, particularly suitable for use with the first cassette unit of FIGS. 1 to 4.
Figure 18:
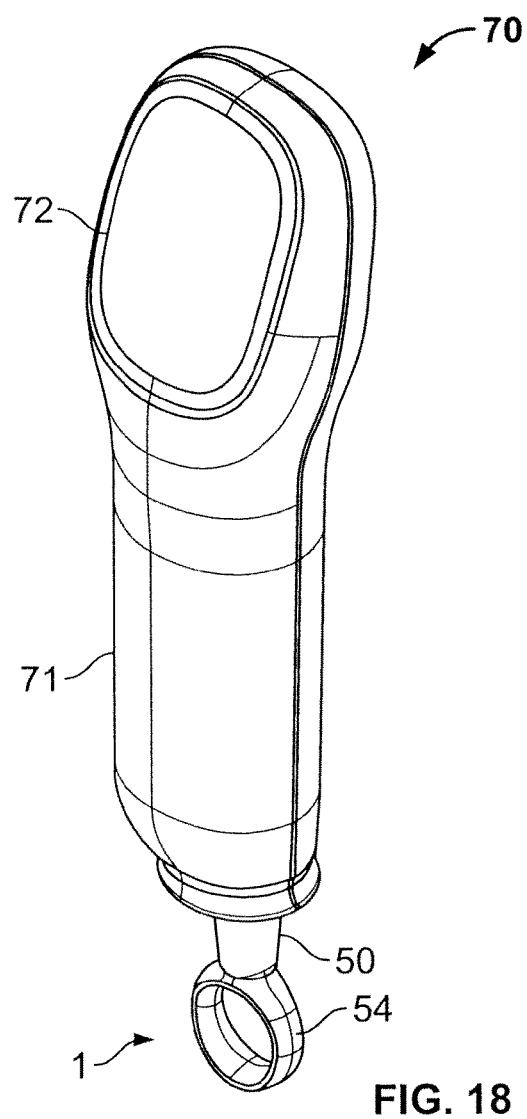
FIG. 18 is a perspective view of the first drive unit of FIG. 17 with a first cassette unit received at the docking position.

FIG. 17 shows a drive unit 70 for use with the cassette unit 1 described herein. The drive unit 70 comprises a drive unit housing 71 for housing a drive arrangement 80, which drive unit housing 71 is sized and shaped at its forward end for receipt of a cassette unit 1. FIG. 18 shows the drive unit 70 having received a representative cassette unit 1 at the docking position, wherein ring pull 54 of the removable cap 50 protrudes from the drive unit housing 71. The drive unit housing 71 is provided with a user-interface in the form of a screen 72, which may in embodiments be a touch-sensitive screen 72.

Figure 19:
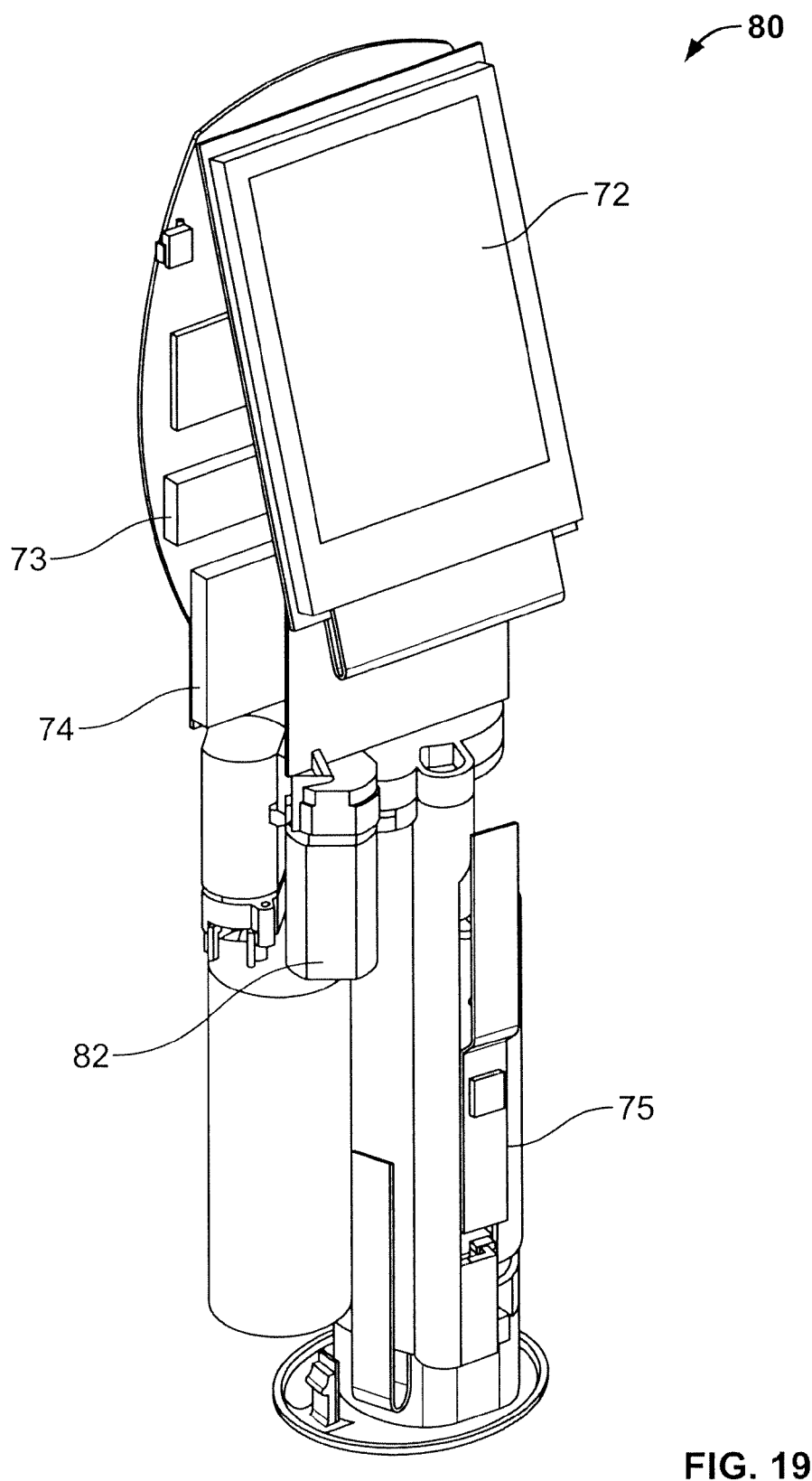
FIG. 19 is a perspective view of the first drive unit of FIG. 17 with the outer cover removed to show the drive arrangement thereof.
Figure 20:
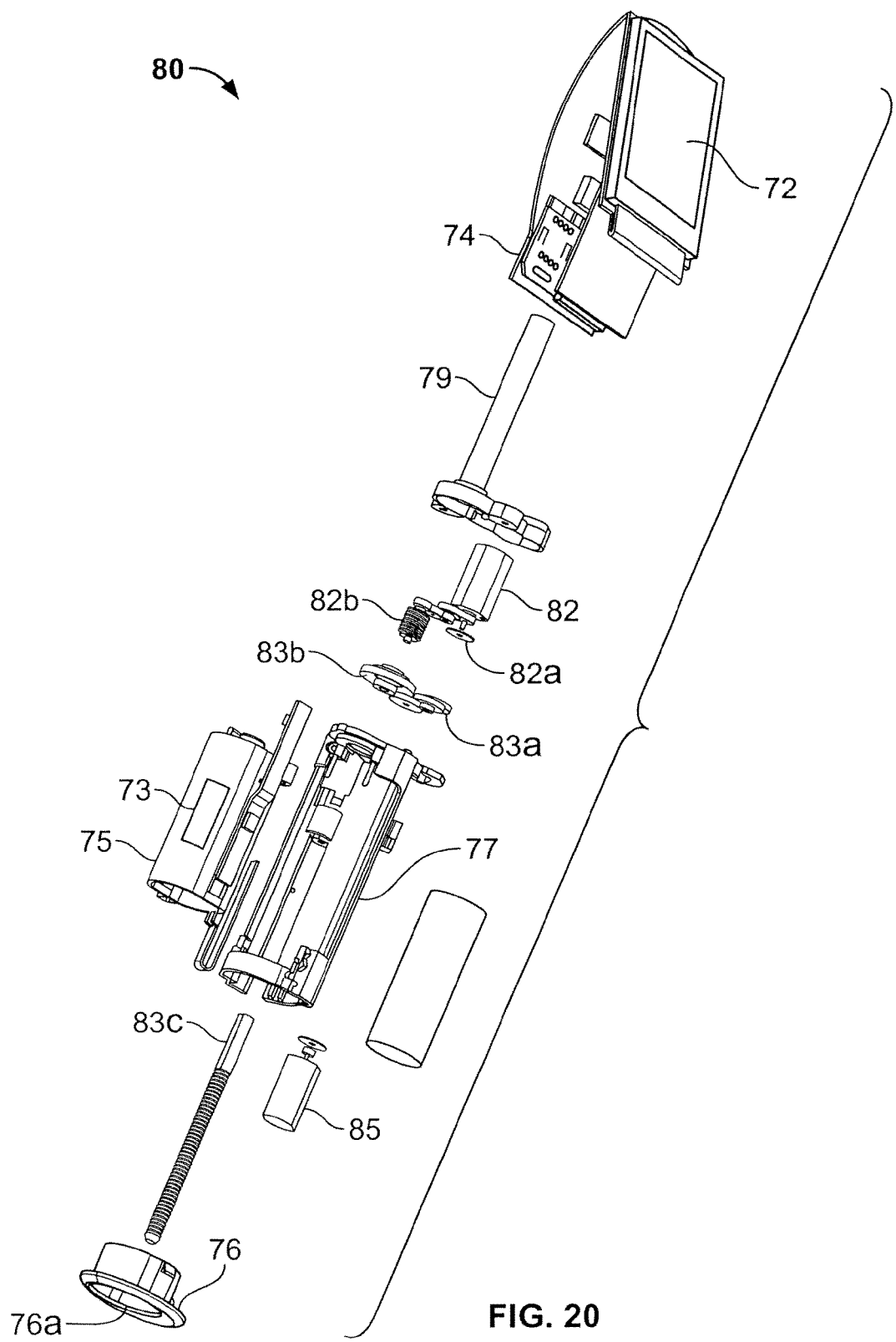
FIG. 20 is an exploded view of the first drive unit of FIG. 17 with the outer cover removed to show the drive arrangement thereof.

FIGS. 19 and 20 shows the inner workings of the drive unit 70 of FIGS. 17 and 18, which has been configured in particular for use with the first cassette unit 1 herein. User-interface 72 may be seen to communicate with circuit board 74, which comprises electronic system circuitry that provides electronic control for the drive arrangement 80 and data processing capability. Further details of a representative electronic control system herein are later described by reference to FIG. 21. The circuit board 74 may also include inputs from various sensors and other electronic components including radiofrequency ID tag reader 73, which locates on cassette unit holder 75 and which is arranged for radiofrequency interrogation of an RFID tag on the cassette unit 1. In other embodiments, the radiofrequency ID tag reader 73 locates at the drive unit at a position closer to where the cassette unit 1 is arranged for receipt.

The cassette unit 1 is received and held within the drive unit housing 71 by cassette unit holder 75, which is received within inner holder frame 77, which in turn seats at forward frame end 76, which defines a cassette-unit receiving aperture/needle delivery aperture 76a therein. Cassette unit holder 75 mounts within frame 77 and is axially (e.g. slidably) movable therein under the selective drive action of first motor 82. The first motor 82 (e.g. stepper motor) selectively transfers drive via first gear 82a to a first drive transfer element in the form of worm 82b. That worm 82b interacts with a rack locating on the back of cassette unit holder 75 to axially move the cassette unit holder 75 and cassette unit 1 and syringe 10 held thereby within the frame 77 from a rest position, in which the needle 14 with tip 15 of the syringe 10 is within the drive unit housing 71 to a use position, in which the needle 14 with tip 15 protrudes from the needle delivery aperture 76a of the drive unit housing.

Second motor 85 (e.g. stepper motor) selectively communicates via second gears 83a, 83b to a second drive transfer element in the form of a threaded screw 83c having cover 79 for subsequently transferring axial drive to the plunger 18 of the syringe 10 for moving the plunger 18 within the barrel 12 of the syringe 10 to eject at least part of the volume of liquid drug formulation contained therein.

In embodiments, the drive unit 70 is arranged for sequential receipt of a cassette unit 1 herein. Thus, in embodiments, the drive unit 70 is arranged for initial receipt of the cassette 1 at an intermediate pre-docking position and for subsequent transport of the cassette unit 1 to the docking position.

In embodiments, the drive unit 70 is arranged such that transport of the cassette unit 1 to the docking position is permitted only following positive verification of the identifier 21. Thus, only appropriately identified cassette units 1 are finally receivable into the device to enable injected drug delivery there from.

In embodiments, the drive unit 70 is arranged such that transport of the cassette unit 1 from an intermediate position to a docking position is permitted only following positive verification of the identifier 21. Thus, only appropriately verified cassette units are finally receivable into the device for drug delivery there from. In embodiments, that transport of the cassette unit 1 to the docking position is by automatic control under the action of the electrically powered source of drive 82. Thus, in embodiments positive verification of the cassette unit 1 gives rise to a 'transport to docking position' signal from the electronic control unit 74; 1001 to the source of drive, which results in the required transporting action.

Figure 21:
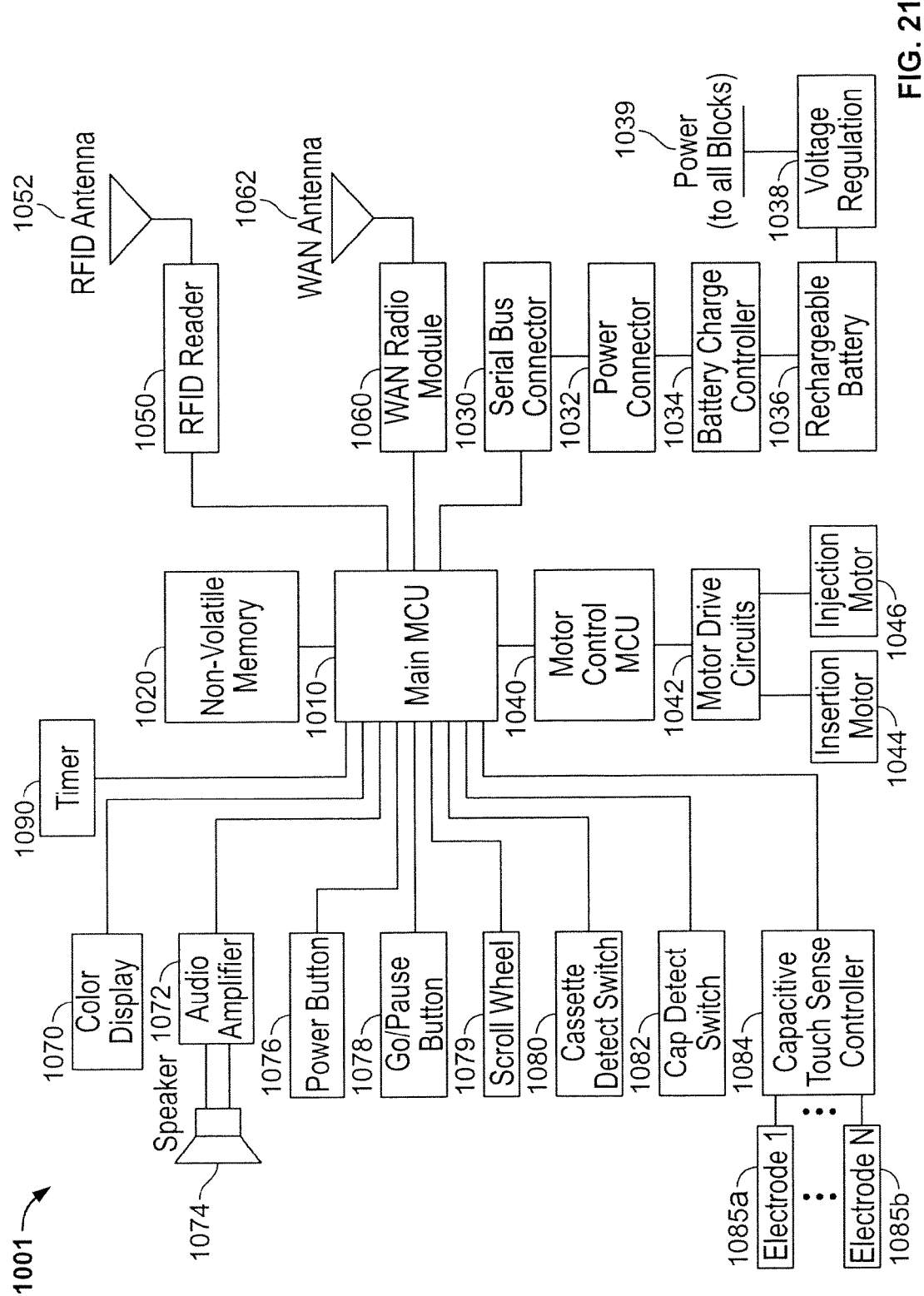
FIG. 21 is a system drawing of a suitable electronic control system for use with the drive unit of FIG. 17.

FIG. 21 shows aspects of a typical electronic control system 1001 herein. Main microprocessor control unit (MCU) 1010 communicates with the following:

Non volatile memory 1020;

Power regulating functions comprising serial bus connector 1030, which is used for power recharge and data communications; power connector 1032; battery charge controller 1034; rechargeable battery 1036; voltage regulator 1038 and power distribution 1039;

Motor control microprocessor control unit (MCU) 1040 for use in controlling the drive motor(s) 82, 85 and communicating with motor drive circuits 1042; insertion motor 82, 1044 and injection motor 85, 1046;

RFID reader 1050 with RFID antenna 1052 for use in reading an RFID tag 21 on the cassette unit 1;

Wide Area Network (WAN) radio module 1060 with WAN antenna 1062 for use in communicating to an external computer network;

User-interface functions comprising colour display 1070; audio amplifier 1072 with speaker 1074; power button 1076; go/pause button 1078; and scroll wheel 1079;

Sensing functions namely, cassette detect switch 1080 for detecting the presence of the cassette within the drive unit; Cap detect switch 1082 for detecting the presence of the removable cap 50 on the cassette unit 1; and capacitive touch sense controller 1084 with electrodes 1085a, 1085b (many such electrodes may be present) for detecting the presence of a user's skin;

Timer function 1090 (a sub-function of the MCU 1010)

In embodiments, the timer function 1090 of the MCU 1010 is initiated by the removal of the removable cap 50 and needle cover 17, 19 from the cassette unit 1. In embodiments, cap detect switch 1080 detects removal of the removable cap 50 (e.g. together with needle cover 17 and rigid needle shield 19) from the cassette unit 1. The timer 1090 then starts counting. In embodiments, once the timer 1090 reaches a certain, pre-determined count a command to cancel the injection (e.g. by preventing the action of the drive/motor function of the drive unit 70) is generated. Drive action of the drive unit 70 is thus, prevented. In embodiments, the timer 1090 therefore acts to ensure that drug is delivered to the patient within a set time limit following removal of the removable cap 50 (e.g. together with needle cover 17 and rigid needle shield 19) from the cassette unit 1. Examples, of timers that may be used include time or actuation-based counters installed on an integrated circuit chip, such as an 'elapsed time counter' such as the DS1602 IC manufactured by Dallas Semiconductor.

During use, within the drive unit 70, the cassette unit 1 is selectively locked into the cassette unit holder 75 by the interaction of engaging tips 95 of locking arms 94 with the locking apertures of the cassette unit holder 75. Selective locking/unlocking is under the control of sprung-loaded cassette unit-unlock cams 88a, 88b, the function of which will now be described in relation to FIGS. 22a to 22c, which for clarity, do not show the cassette unit 1, but only the relevant drive unit 70 parts.

Figure 22A:
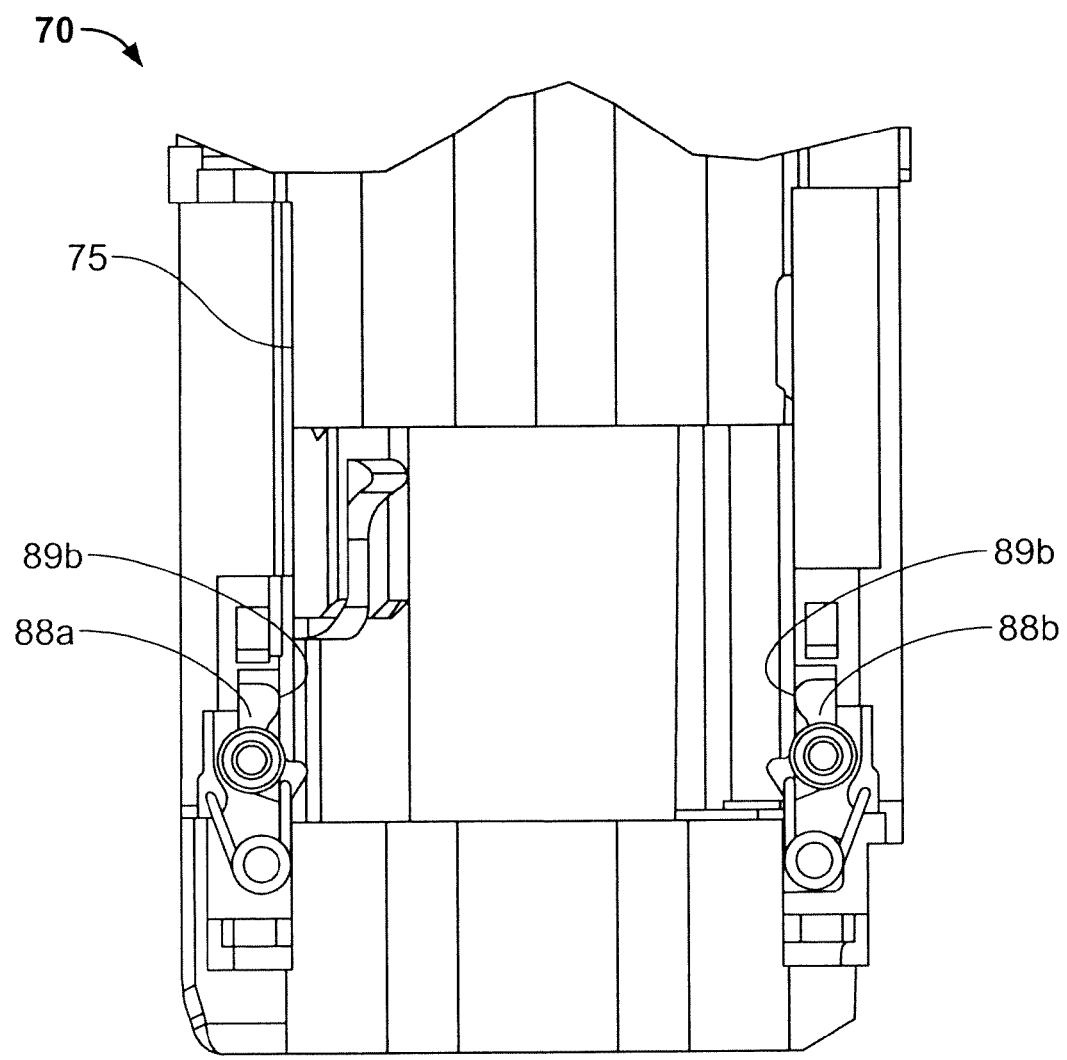
FIGS. 22a to 22c are sectional views showing sequential use steps of the cassette unit holder locking mechanism of the drive unit of FIGS. 19 and 20 (shown without cassette unit)

FIG. 22a shows the cassette unit holder 75 in the docking position, in which the cams 88a, 88b are spring-biased to the 'cassette unit 1 unlocked' position wherein the rounded heads 89a, 89b of each cam 88a, 88b are upright. The position corresponds to that, in which the removable cap 50 is unlocked, as further shown at FIGS. 23e and 24e.

Figure 22B:
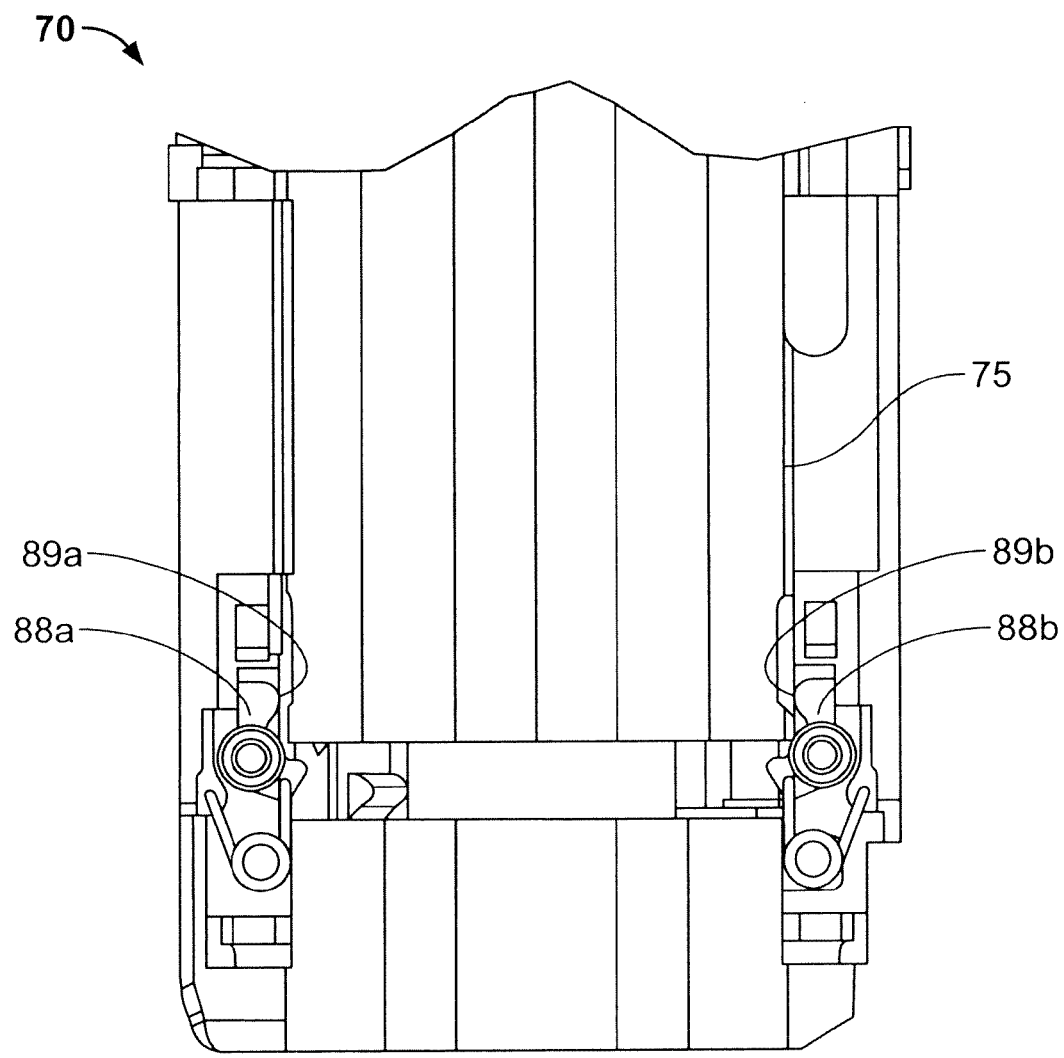

FIG. 22b shows the cassette unit holder 75 moved forwards, but not yet engaging the cams 88a, 88b. The rounded heads 89a, 89b of each cam 88a, 88b remain upright. The position corresponds to that, in which the cassette unit 1 is inserted into the drive unit 70 for verification, as further shown at FIGS. 23c and 24c.

Figure 22C:
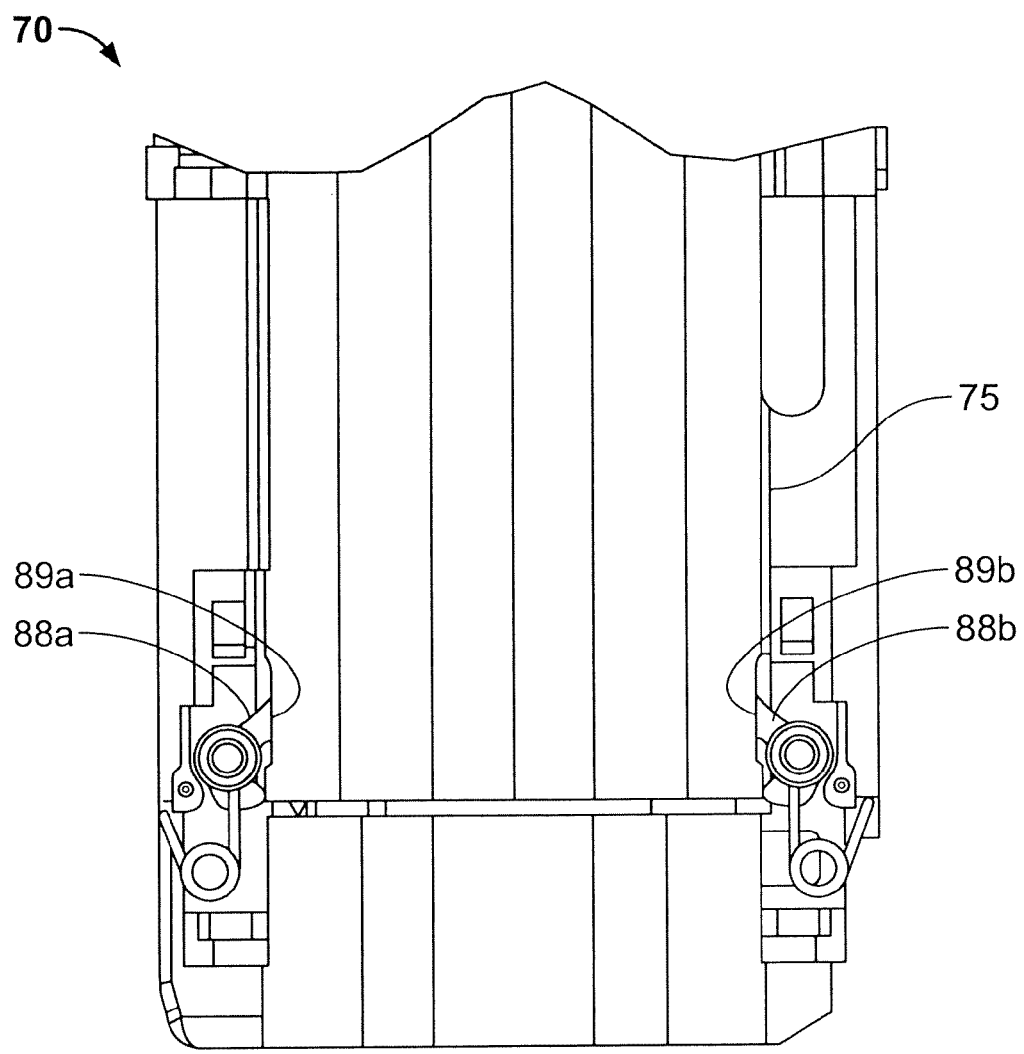

FIG. 22c shows the cassette unit holder 75 moved further forwards such as engage the cams 88a, 88b and to rotationally drive the rounded heads 89a, 89b of each cam 88a, 88b into a 'head bowed' position. When in this 'head bowed' position, the cams 88a, 88b may interact with the engaging tips 95 of locking arms 94 of the cassette unit housing 20 out of locking engagement with the locking aperture and thus, to allow the cassette unit 1 to be released from the cassette unit holder 75. The position, which is the forward-most position of the cassette unit holder in use, corresponds to that, in which the cassette unit 1 may be ejected from the drive unit 70 after injected use, as further shown at FIGS. 23i and 24i.

Further aspects of the first auto-injector device herein may now be appreciated by reference to FIGS. 23a to 23i and FIGS. 24a to 24i and to the following description of a typical use operation: These show and describe sequential use steps of a first drive unit 70 essentially in accord with that already described by reference to FIGS. 17 to 20 as particularly used in conjunction with a first cassette unit 1 essentially in accord with that already described by reference to FIGS. 1 to 4. The first drive unit 70 includes an electronic control system (not shown) essentially of the type described by reference to FIG. 21. For clarity, only those aspects of FIGS. 23a to 23i and 23a to 23i most relevant to the use operation being described are identified by labelling.

Figure 23A:
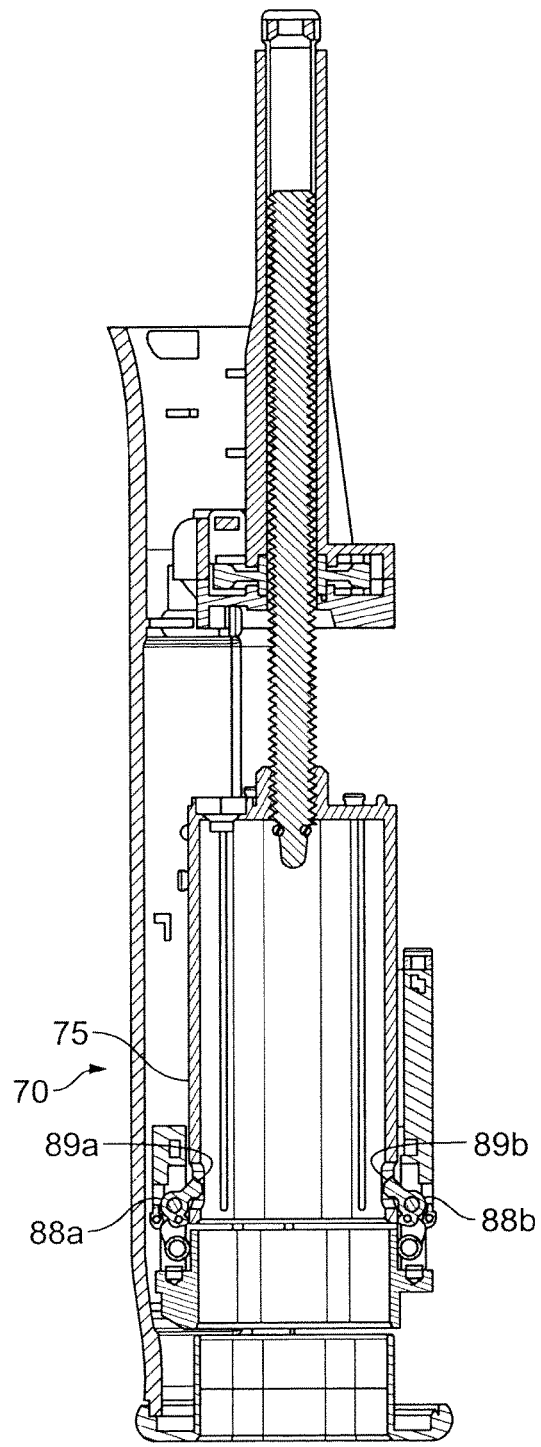
FIGS. 23a to 23i are sectional views showing sequential use steps of a first drive unit of FIGS. 17 to 20 with a first cassette unit of FIGS. 1 to 4.
Figure 24A:
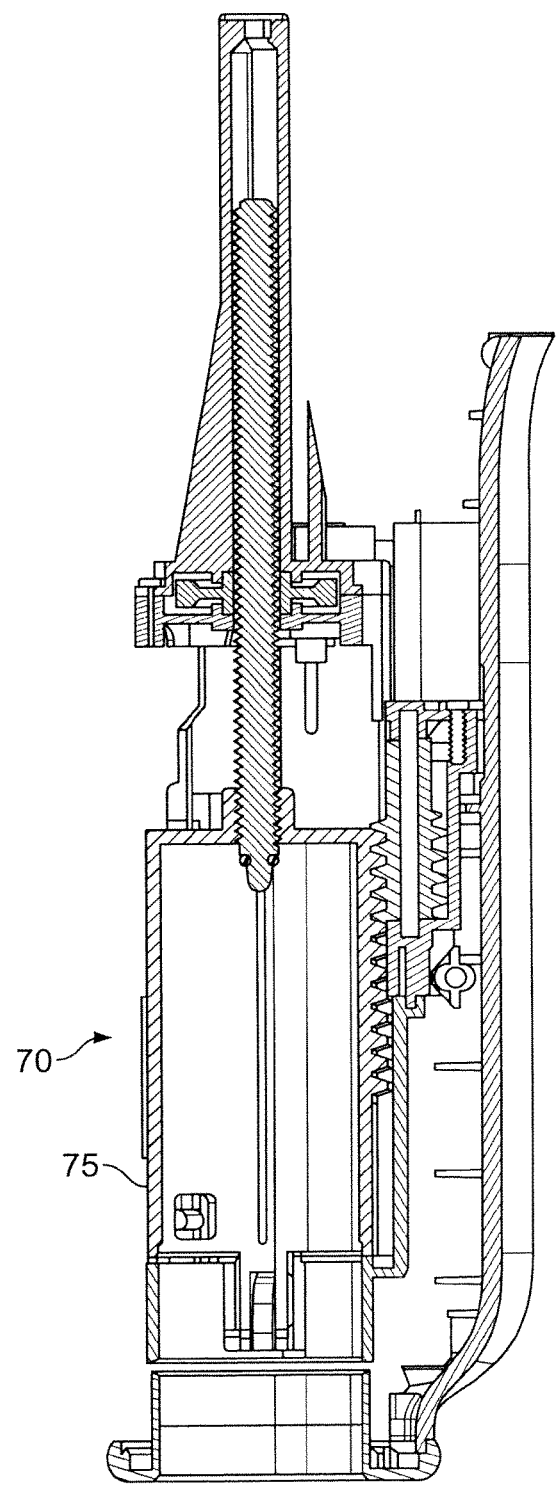

Initially, the auto-injector device is in the 'powered down' state as shown at FIGS. 23a and 24a, to which it returns after completion of a full use sequence, as described hereinbelow. The position of FIGS. 23a and 24a, which is the forward-most position of the cassette unit holder 75 in use, thus corresponds to that, in which the cassette unit 1 may be ejected from the drive unit 70 after injected use. Thus, the cassette unit holder 75 has engaged with the sprung cams 88a, 88b to rotationally drive the rounded heads 89a, 89b of each sprung cam 88a, 88b into a 'head bowed' position. As previously described, when in this 'head bowed' position, the cams 88a, 88b may interact with the engaging tips 95 of locking arms 94 of the cassette unit housing 20 out of locking engagement with the locking aperture and thus, to allow the cassette unit 1 (not shown) to be released from the cassette unit holder 75.

In a first stage of a typical use operation and to prepare for use of the device, the user hits the power on button 1076 and thereby turns the electronic control system 1001 on. A 'welcome message' is displayed on the screen 72; 1070 (see FIGS. 17 to 20), which instructs the user to insert the cassette unit 1.

Figure 23B:
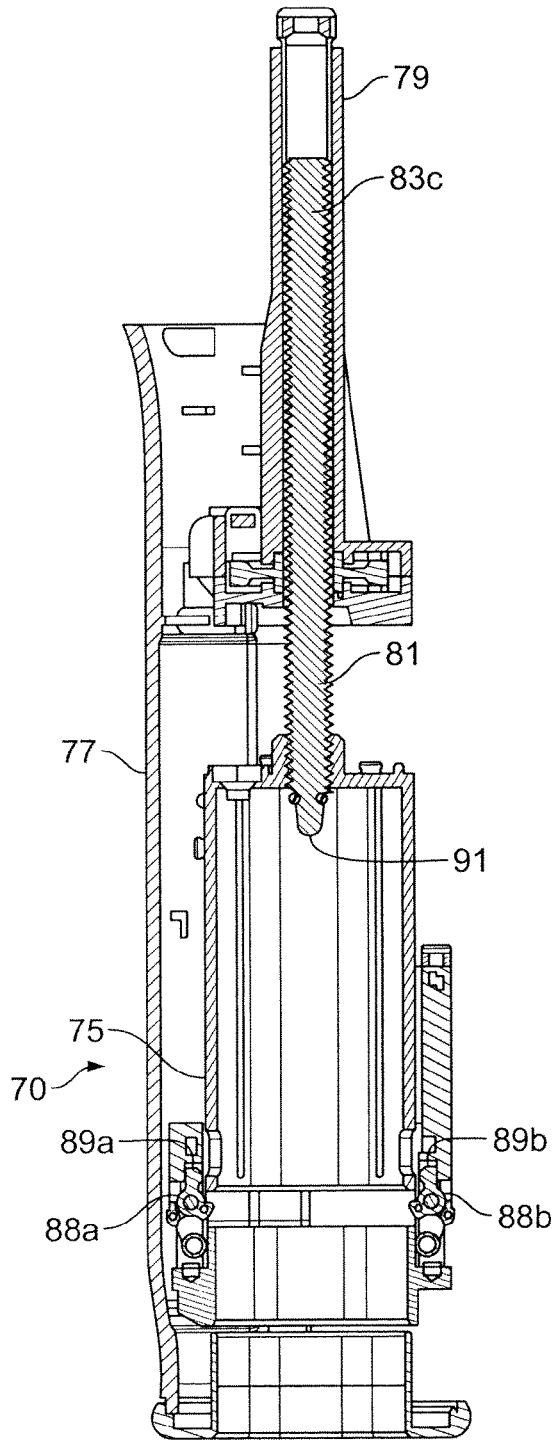

After power on, the auto-injector device adopts the configuration as shown at FIGS. 23b and 24b, in which the drive unit 70 is initially in the 'cassette receipt' position. The cassette unit holder 75 has been withdrawn backwards slightly to the 'cassette receipt' position within frame 77. In this position, the cassette unit holder 75 no longer engages with the sprung cams 88a, 88b and the rounded heads 89a, 89b thereof are now biased back to a 'head upright' position. First drive transfer element in the form of worm drive 82b for movement of the cassette unit holder 75 sets it in the 'cassette receipt' position interacting (as visible in FIG. 24b only) with rack 75a provided along one side of the cassette holder. Second drive transfer element in the form of threaded screw 83c located within cover 79, the threaded screw 83c serving as a plunger rod 81 (for plunging movement of the plunger 18 of the syringe 10) is in its 'at rest' position. The cassette unit 1 contains a syringe including a syringe plunger 18 that interfaces with the plunger rod 81 upon activation for delivering medication. Forward end of the plunger rod 81 is provided with tapering, round headed end-piece 91.

Figure 23C:
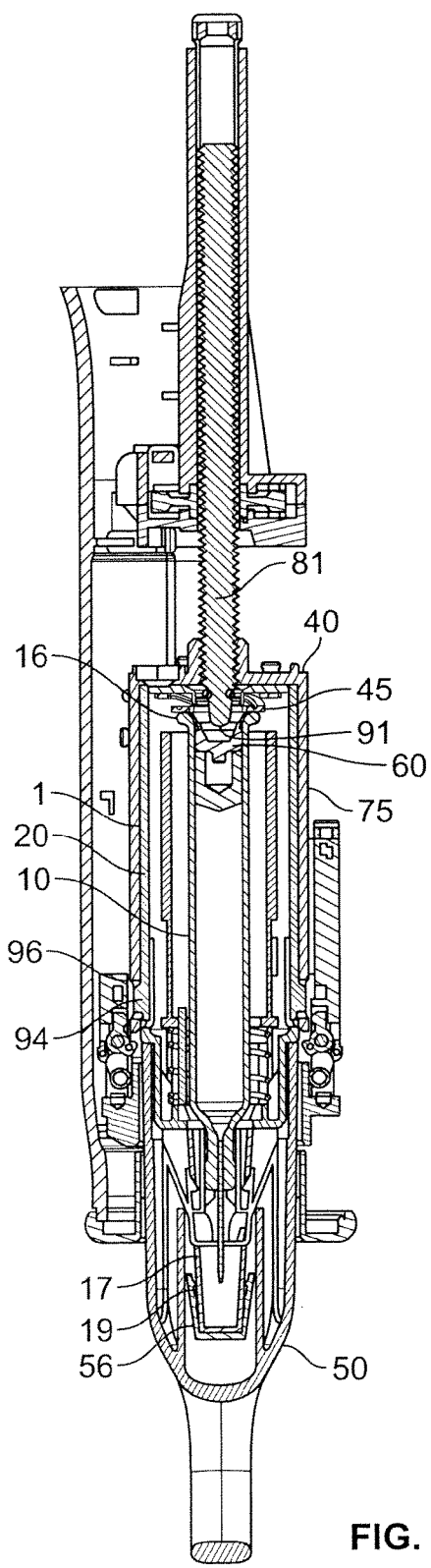

In a second stage of a typical use operation, as shown at FIGS. 23c and 24c, the user inserts cassette unit 1 comprising syringe 10 and having removable cap 50 to the intermediate pre-docking position within the cassette unit holder 75 of the drive unit 70. Needle cover gripper 56 in the form of a cage-like (or 'flower') structure is provided to the removable cap 50 for gripping of the rigid needle sheath shield 19 and configured such that removal of the cap 50 also results in removal of the rigid needle sheath shield 19 and needle sheath 17 enclosed thereby, and hence, unsheathing of the needle tip 15. In this position, forward end of the plunger rod 81 with its tapering, round headed end-piece 91 is received within the drive rod-receiving opening (not labelled) of the cassette unit end-cap 40. End-cap spring 45 defines a sprung biasing relationship between the cassette unit end-cap 40 and the flange 16 of the syringe 10, thereby urging the syringe 10 forwards in relation to the cassette unit end cap 40. Plunger slaving part 60 is in releasable engagement with the cassette unit end-cap 40. As will be described hereinafter, in use, the plunger slaving part 60 is released from the cassette unit end-cap 40 in response to forward axial drive provided by the plunger rod 81, 91 to a rear drive-receiving face thereof.

The general function of the tapering, round-headed end-piece 91 of the plunger rod 81 is to give rise to a point load instead of a face load. The slaving part 60 is made of a hard material, thus acting to reduce friction and torsion loads on the system. The slaving part 60 is arranged to function such that when a load is applied to its top face the load is evenly transmitted directly into the syringe plunger 18. In embodiments, the slaving part 60 is coloured and performs a second function of providing an easy-to-identify visual indicator of the position of the plunger 18 within the syringe 10 so that the patient can visually confirm the drug had been fully injected.

As shown at FIG. 23c, in the intermediate pre-docking position the cassette unit 1 is locked into the cassette unit holder 75. Thus, flexible locking arms 94 of the cassette unit housing 20 locate within locking apertures 96 of cassette unit holder 75.

As shown at FIG. 24c, in the intermediate pre-docking position, shuttle lock control 32 is in the first 'cassette unused' position and thus, the removable cap 50 is in the cap locked position (also see FIGS. 8a, 9a, 10a and 11a). The inner face of the locking arm 26 of the cassette unit housing 20 is blocked, thereby preventing any inwards movement thereof and so effectively also thereby, preventing any disengagement of the angled tip 29 of that locking arm 26 from socket through-hole 52 of the removable cap 50.

As also shown at FIG. 24c, in the intermediate pre-docking position, pushing member in the form of pin 78 is spaced from the cassette 1, but locates immediately above protruding arms 31 of the inner housing sleeve 30, which are thus accessible to it via cut-away apertures 51 of the cassette unit end cap 40. More typically, a spaced pair of pins 78 would be provided. It will be appreciated that relative movement of the cassette 1 towards the pin 78 (e.g. to the position of third stage of a typical use operation of FIG. 24d, as described below) will result in receipt of pin 78 into cut-away aperture 51 of the cassette unit end cap 40 such as to bring pin 78 into pushing contact with protruding arm 31 of the inner housing sleeve 30 to thereby push the inner housing sleeve 30 and the shuttle lock control 32 forward.

Verification of the cassette unit 1 occurs at this intermediate pre-docking position. Thus, RFID reader 73; 1050 (see FIGS. 19 to 21) of the drive unit interrogates RFID tag 21 (see FIG. 3) of the cassette unit 1 and thereby, reads verification information from the RFID tag 21 of the cassette unit 1. Such verification can for example, be for the purpose of checking of drug and dosage information, checking that the drug is not past its expiry date and/or checking that the cassette unit 1 has not been used previously.

Figure 23D:
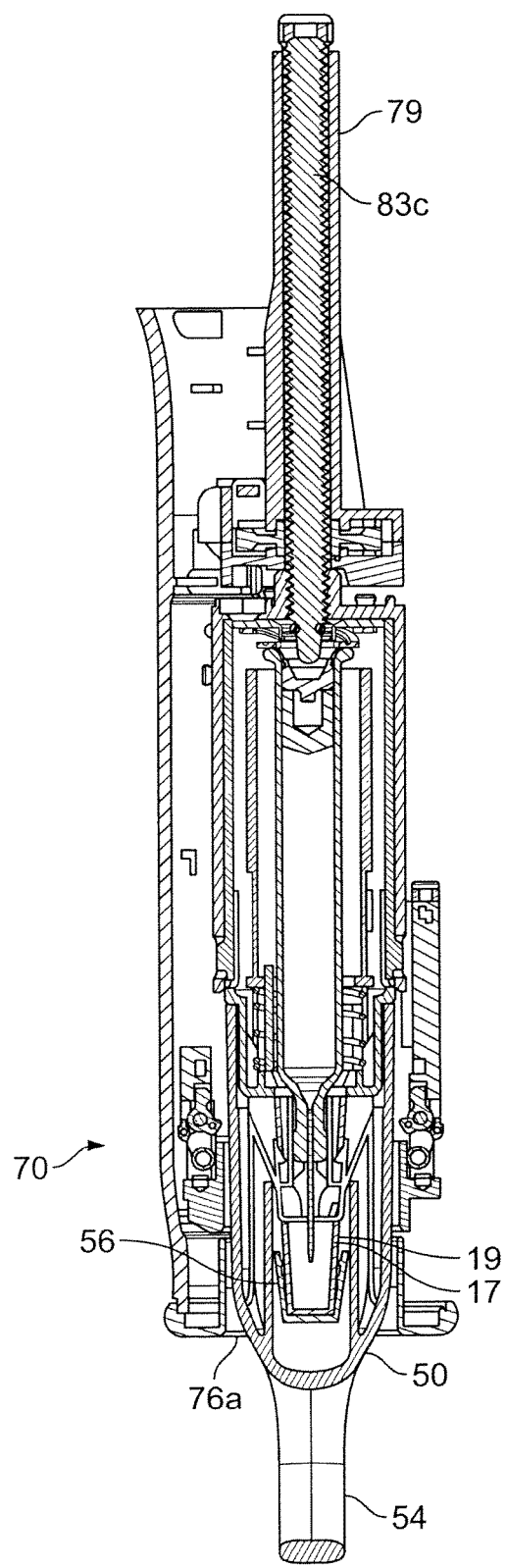
Figure 24D:
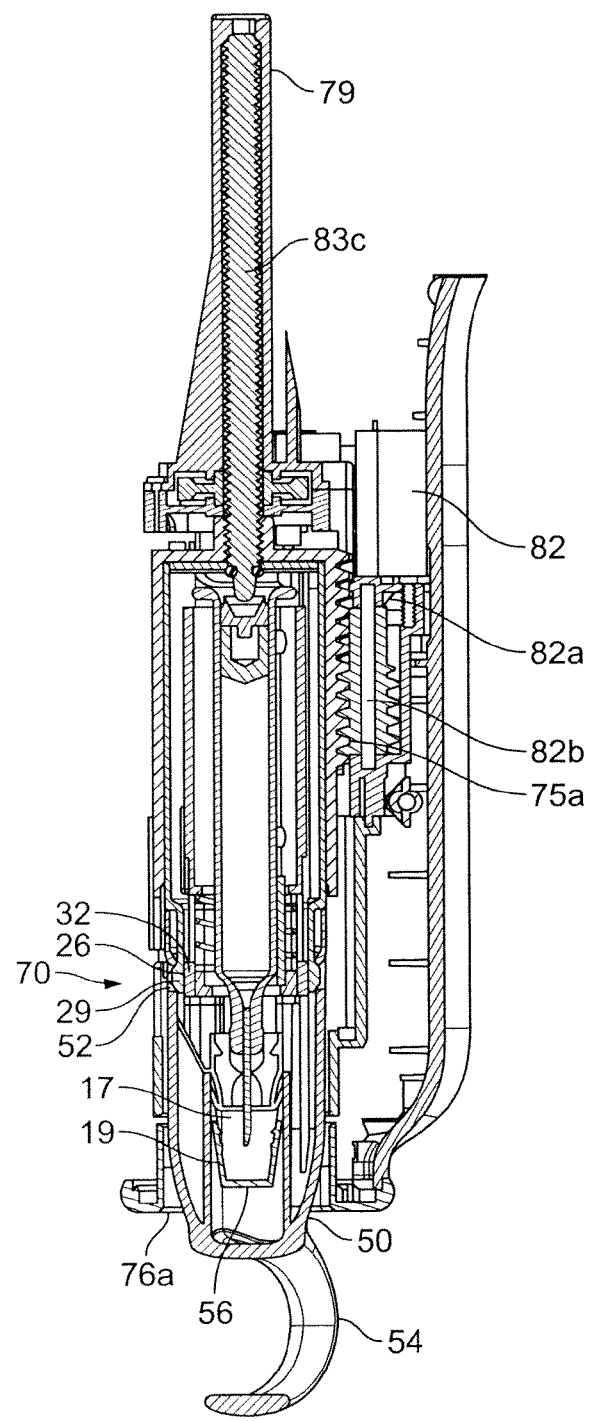

Upon positive verification of the cassette unit 1, the cassette unit holder 75 and cassette unit 1 held therein are drawn further up (i.e. transported) into the drive unit 70 to the docking position of third stage of a typical use operation of FIGS. 23d and 24d. Such drawing up is achieved by the drive action of worm drive 82b on rack 75a of the cassette unit holder. The worm drive 82b receives axial drive from first motor 82; 1042 via gear 82a in response to a command from motor drive circuits 1042 acting under the control of motor control MCU 1040, which in turn communicates with main MCU 1010.

It will be noted that in the docking position, the threaded screw 83c has been drawn deeper into its cover 79. It will also be noted that end-ring 54 of removable cap 50 still protrudes out with the exit aperture 76a of drive 70, but otherwise the cassette unit 1 is fully within the drive unit 70.

As shown at FIG. 24d, in the docking position, the shuttle lock control 32 is in the second 'cassette unlocked' position (having been pushed relatively forward by the interaction of protruding arms 31 with pushing pin 78) and thus, the removable cap 50 is in the cap unlocked position (also see FIGS. 9b, 10b and 11b). The inner face of the locking arm 26 of the cassette unit housing 20 is no longer blocked. As a result, inwards movement of the locking arm 26 is no longer prevented and disengagement of the tip 29 of the locking arm 26 from socket through-hole 52 of the removable cap 50 is achievable by suitable inwards pushing action on the tip 29/locking arm 26. Such inward pushing action on the locking arm 26 is achievable by pulling the cap 50 away from the cassette unit 1, which results in the angled tip 29 interacting with the wall edges of the socket through-hole 52 to push the locking arm 26 inwards.

The screen 72; 1070 now displays an instruction to the user to remove the cap 50 of the cassette unit 1. The drive unit 70 is provided with a timer function 1090, which is initiated by the removal of the removable cap 50 from the cassette unit 1. Cap removal sensing means 1082 are provided to detect removal of the removable cap 50 from the cassette unit 1. The timer 1090 then starts counting. In embodiments, once the timer 1090 reaches a certain, pre-determined count a command to prevent the drive function 80 of the drive unit 70 is generated. Drive action of the drive unit 70 is thus, prevented. The timer therefore acts as a safety measure to ensure that drug is delivered to the patient within a set time limit following removal of the removable cap 50 from the cassette unit 1.

Figure 23E:
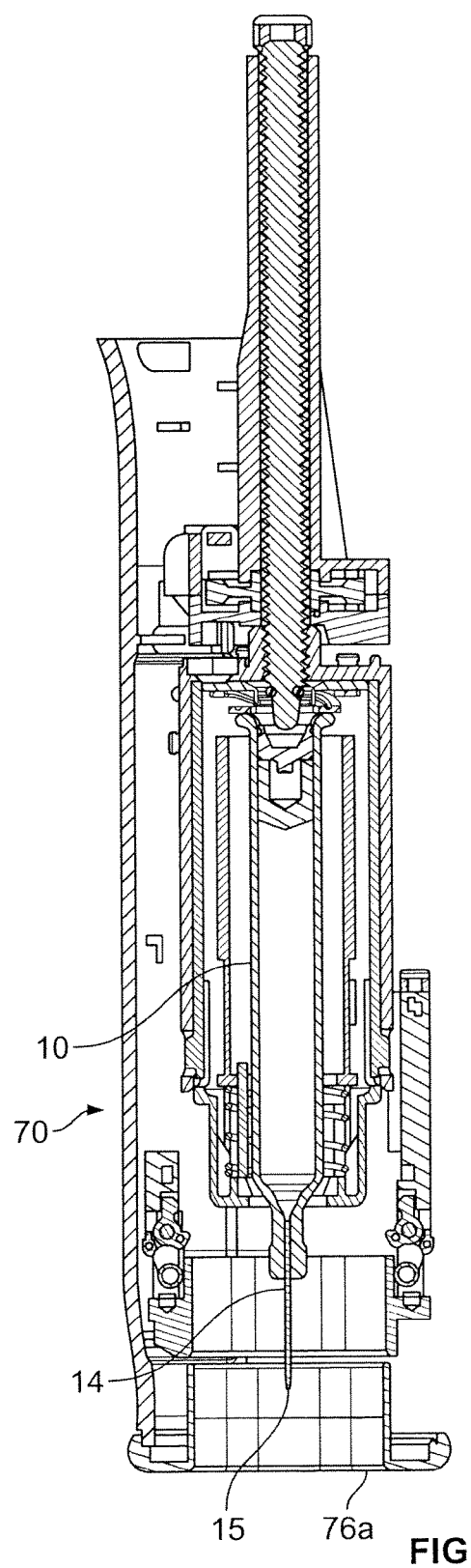
Figure 24E:
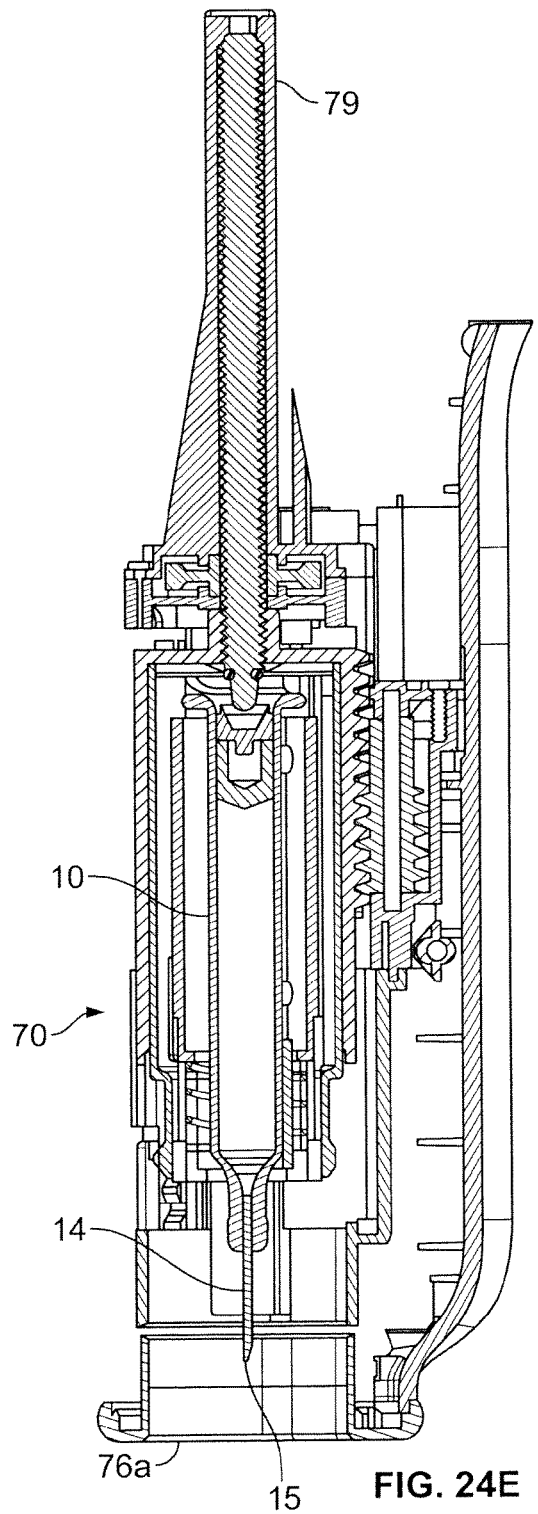

In a fourth stage of a typical use operation, as shown at FIGS. 23e and 24e, the user has removed the cap 50 together with needle sheath 17 and rigid needle shield 19. The needle 14 with tip 15 of the syringe 10 is now uncovered, but still shrouded by the drive unit 70 and does not protrude from the exit aperture 76a thereof. The screen 72; 1070 now displays an instruction to the user to place the device (i.e. the exit aperture 76a thereof) against the injection site. Once the exit aperture 76a has been placed against the injection site electrodes 1085a, 1085b of capacitive touch sense controller (e.g. skin sensor) register the correct placing of the device at the injection site. The screen 72; 1070 now displays an instruction to the user to initiate the injection by pressing the 'inject' button. In other embodiments, such initiation of the injection may be configured to occur automatically on sensing of the correct placing of the device at the injection site.

Figure 23F:
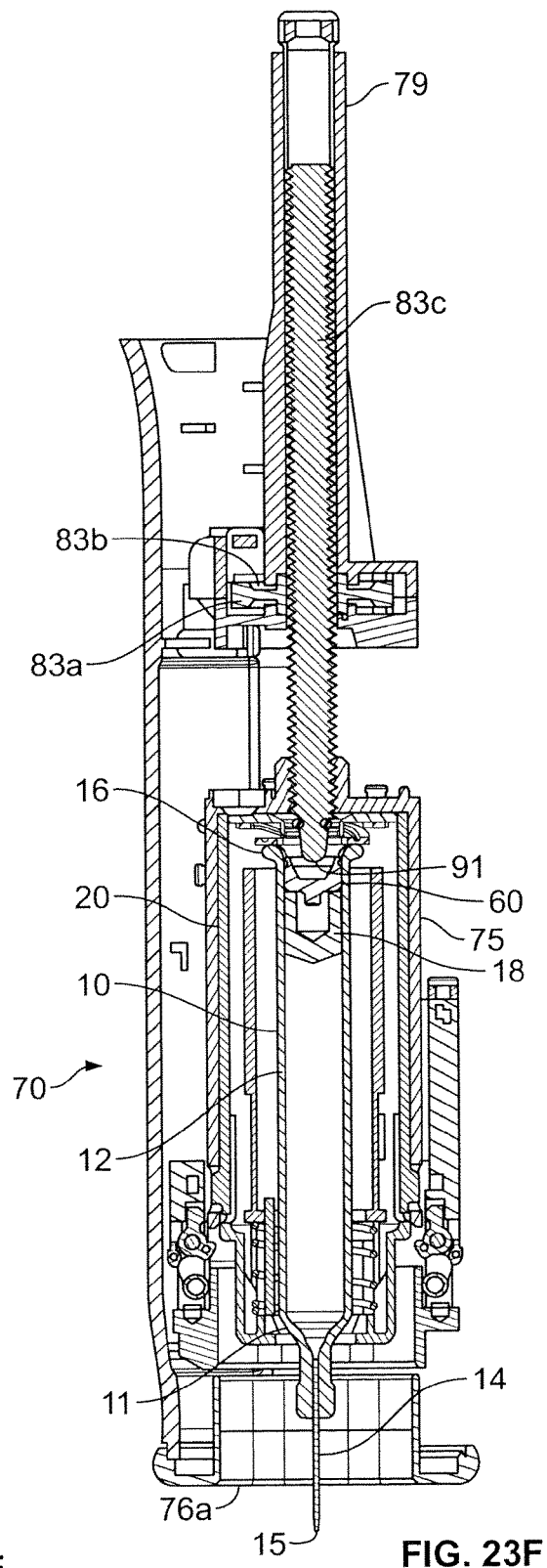
Figure 24F:
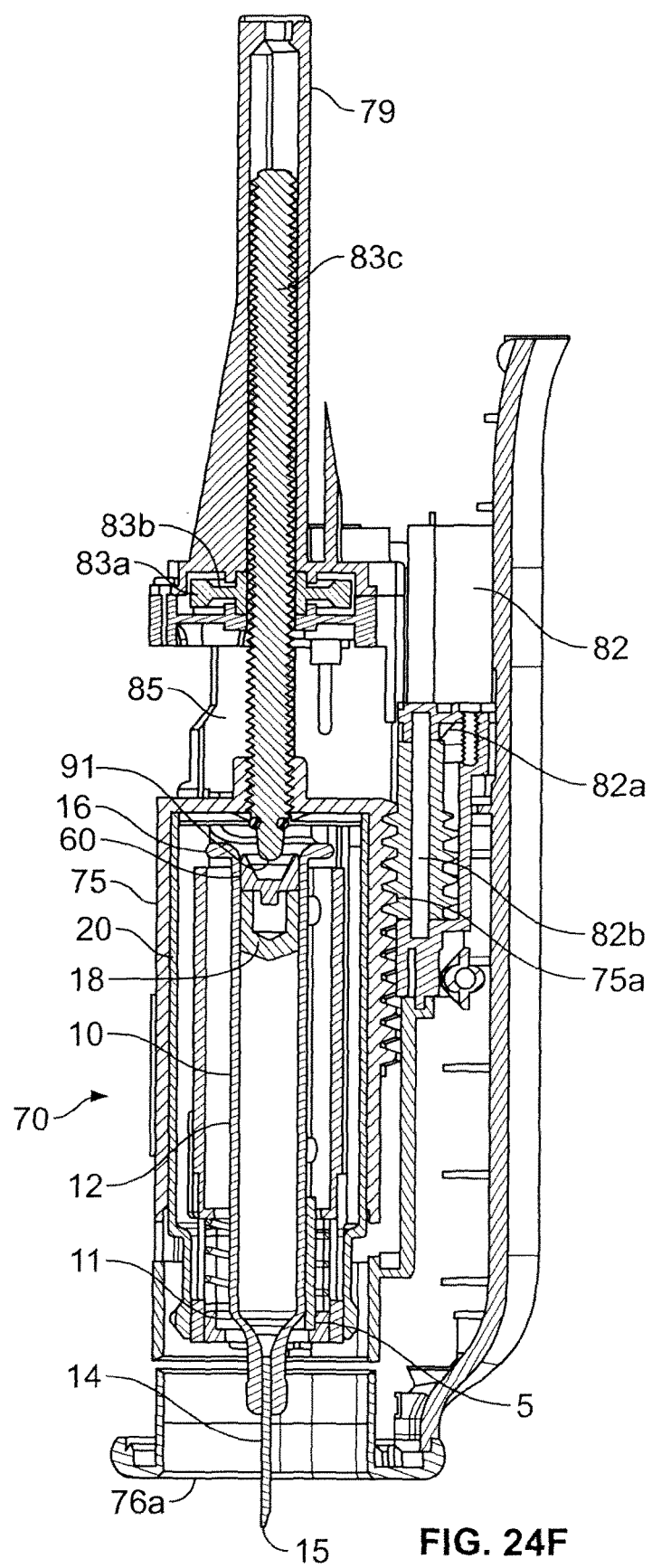

In a fifth stage of a typical use operation, as shown at FIGS. 23f and 24f, the syringe 10 has now been advanced to the injection position, in which the tip 15 of the needle 14 protrudes out with the exit aperture 76a. Such advancement of the syringe 10 has been achieved by forward movement of the cassette unit holder 75, which is responsive to the forward driving action of worm drive 82b on rack 75a of the cassette unit holder 75. The worm drive 82b receives axial drive from first motor 82; 1042 via gear 82a in response to a command from motor drive circuits 1042 acting under the control of motor control MCU 1040, which in turn communicates with main MCU 1010. It will also be noted that in the injection position, the threaded screw 83c has been drawn forwards within its cover 79.

Once the syringe 10 is at the injection position of FIGS. 23f and 24f, ejection of drug from the syringe barrel 12 can commence. Such ejection in response to forward advancement of threaded screw 83c responsive to geared driving by gears 83a, 83b, which receive axial drive from second motor 85; 1046 in response to a command from motor drive circuits 1042 acting under the control of motor control MCU 1040, which in turn communicates with main MCU 1010. Threaded screw 83c via end-piece 91 is brought into forward driving contact with rear drive-receiving end of slaving part 60. The resulting forward advancement thereof results in release of the plunger slaving part 60 from the end-cap 40 and then in forward sliding movement of that slaving part 60 within the syringe barrel 12, which in turn results in plunging movement of the plunger 18 within the barrel 12 of the syringe 10 to expel the drug formulation contents through the tip 15 of the needle 14 and into the injection site (e.g. skin of the user). The slaving part 60 functions such that when a driving load is applied to its rear drive-receiving face 63, 66 by round headed end-piece 91 of threaded screw 83c the load is evenly transmitted directly into the syringe plunger 18.

To reduce the risk of the syringe 10 fracturing under the loads associated with injecting the drug, it is important for a majority of the load path to travel through the forward shoulder 11 of the syringe barrel 12 and lesser load to pass through the flange 16 at the rear end thereof. It may therefore be seen at FIG. 24f that forward shoulder 11 of the syringe 10 is surrounded by shoulder support feature 5 (see also FIGS. 5a to 5c). Information related to the progress of the injection may be displayed on the screen 72; 1070 including for example, a signal that 'injection has been completed successfully'.

Figure 23G:
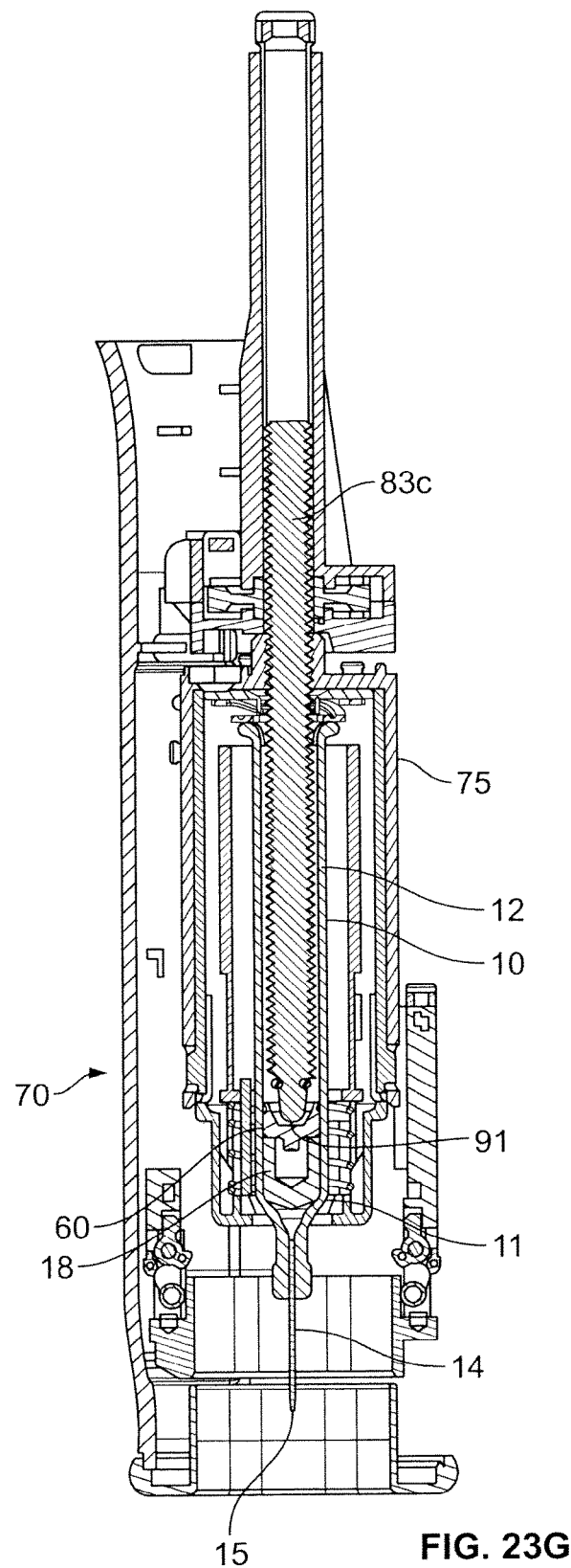
Figure 24G:
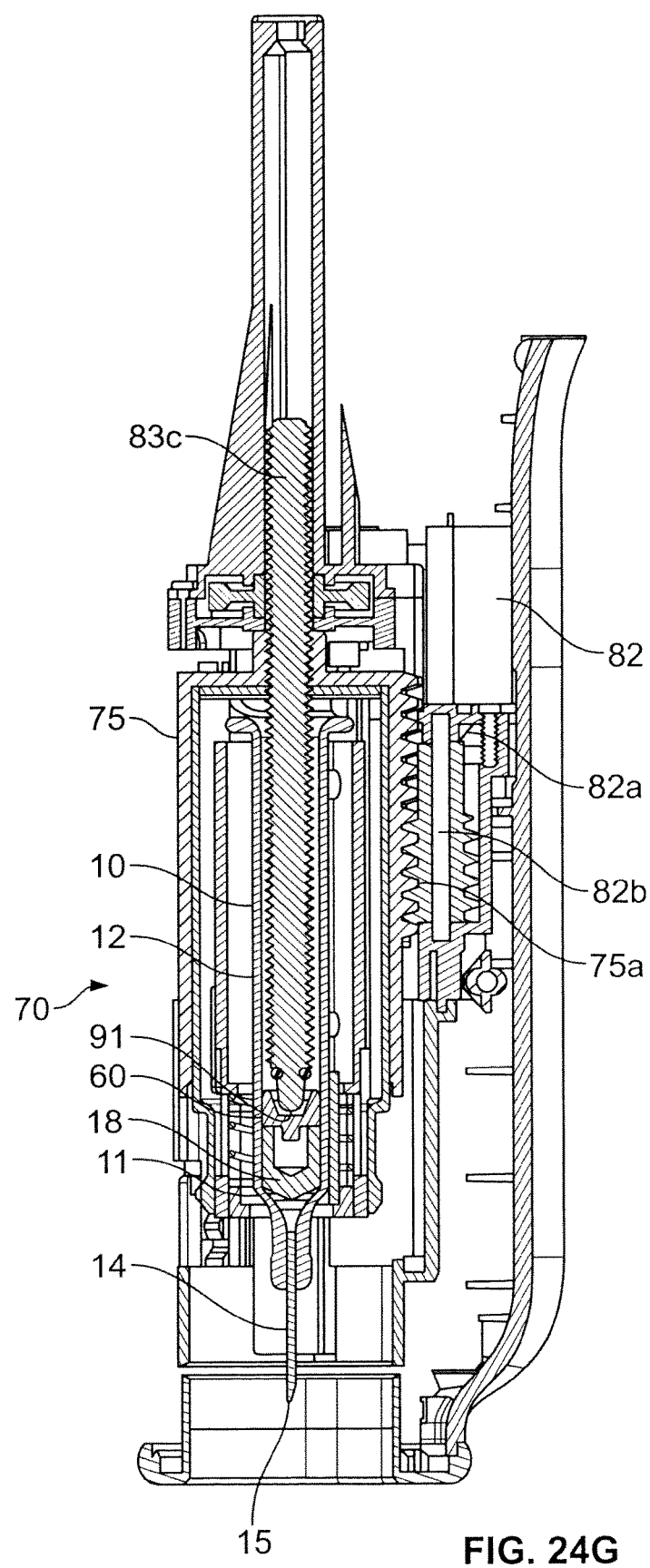

In a sixth stage of a typical use operation, as shown at FIGS. 23g and 24g, post-completion of the injection, the needle 14 with tip 15 of the syringe 10 has been withdrawn back into the drive unit 70. Such withdrawal of the syringe 10 is achieved by rearwards movement of the cassette unit holder 75, which is responsive to the rearward driving action of worm drive 82b on rack 75a of the cassette unit holder 75. The worm drive 82b receives axial drive from first motor 82; 1042 via gear 82a in response to a command from motor drive circuits 1042 acting under the control of motor control MCU 1040, which in turn communicates with main MCU 1010.

It will be noted in the post-injection position of FIGS. 23g and 24g that threaded screw 83c with end-piece 91 has been advanced forward sufficiently to drive both slaving part 60 and the plunger 18 within the barrel 12 of the syringe 10 fully forwards. Thus, the leading end of the plunger 18 locates adjacent to the neck 11 of the syringe 10. The slaving part 60 is coloured and performs a secondary function of providing an easy-to-identify visual indicator of the position of the plunger 18 within the syringe 10 so that the patient can visually confirm the drug had been fully injected. The screen 72; 1070 now displays a message instructing the user to replace the cap 50.

Figure 23H:
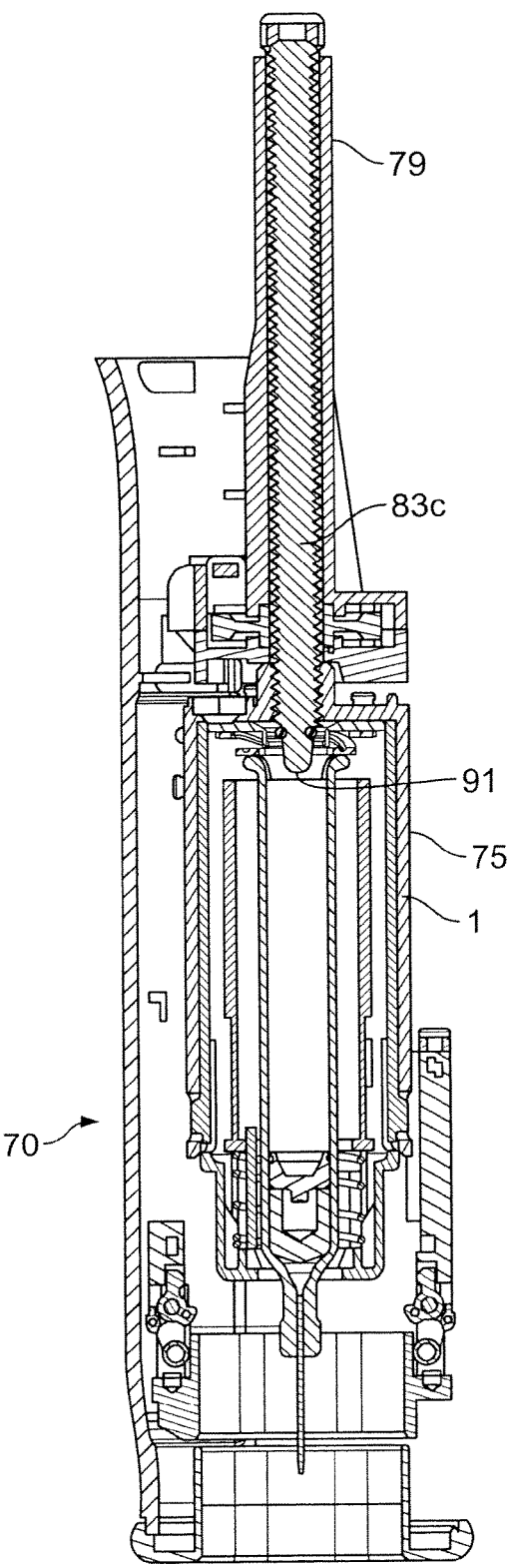
Figure 24H:
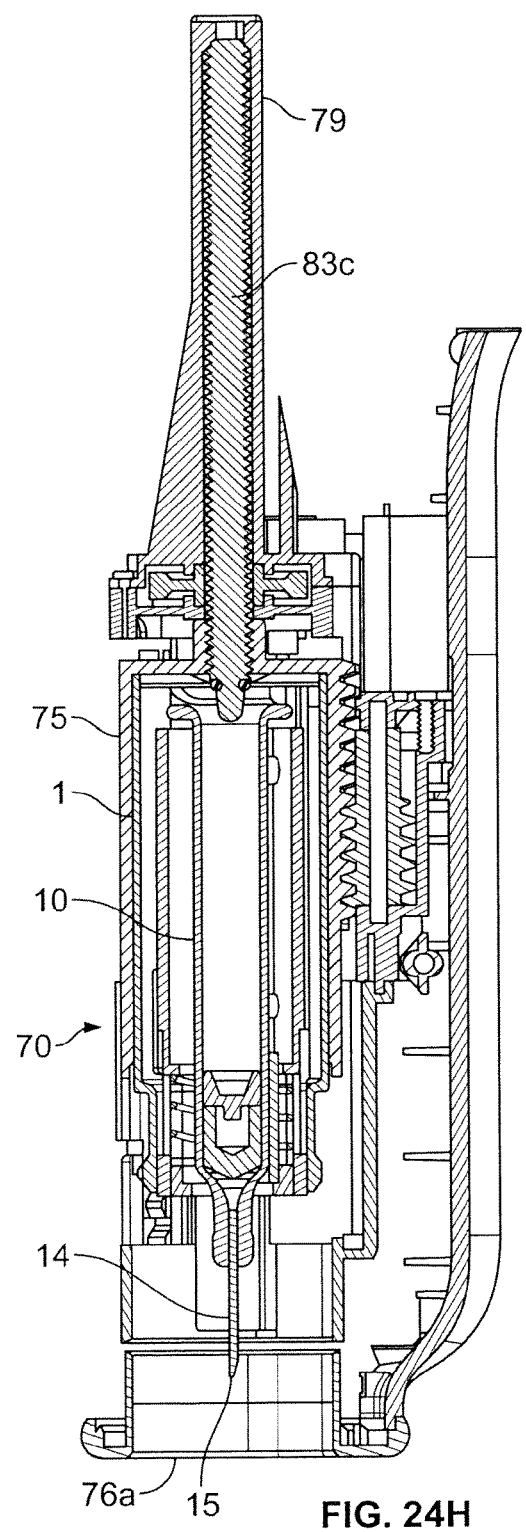

In a seventh stage of a typical use operation, as shown at FIGS. 23h and 24h, threaded screw 83c with end-piece 91 has been withdrawn into its cover 79 to the 'at rest' position. At this stage, the cassette unit 1 is still in locked engagement with the cassette unit holder 75 and removal of the cassette unit 301 is therefore not possible.

Figure 23I:
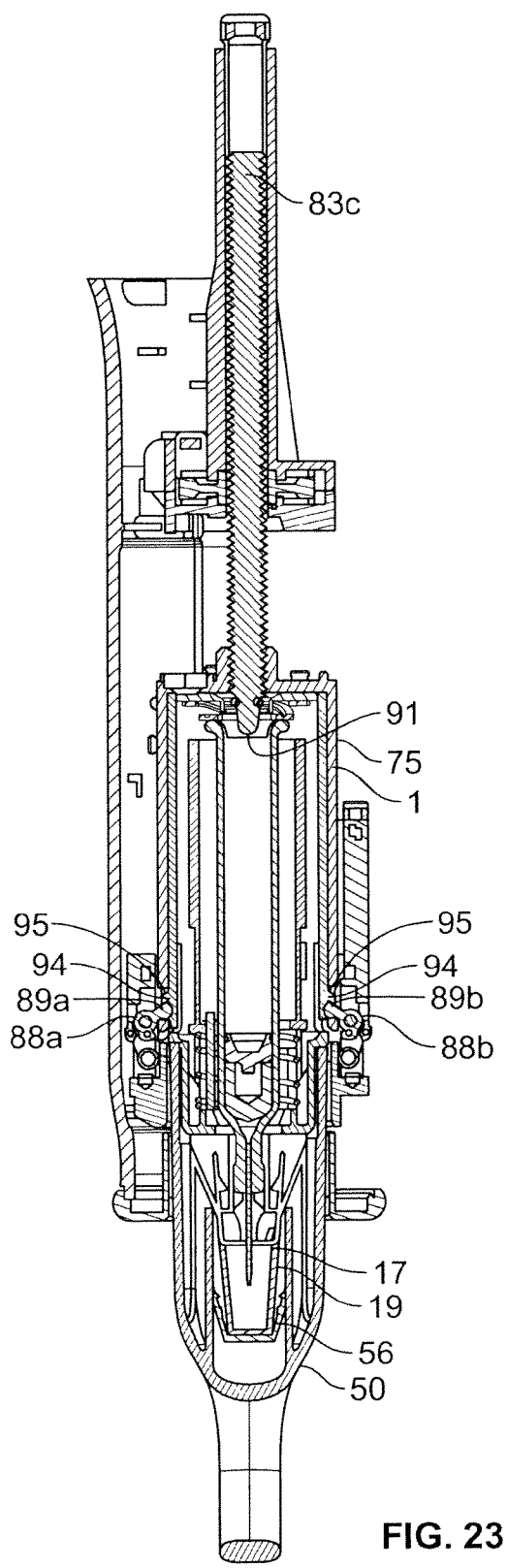
Figure 24I:
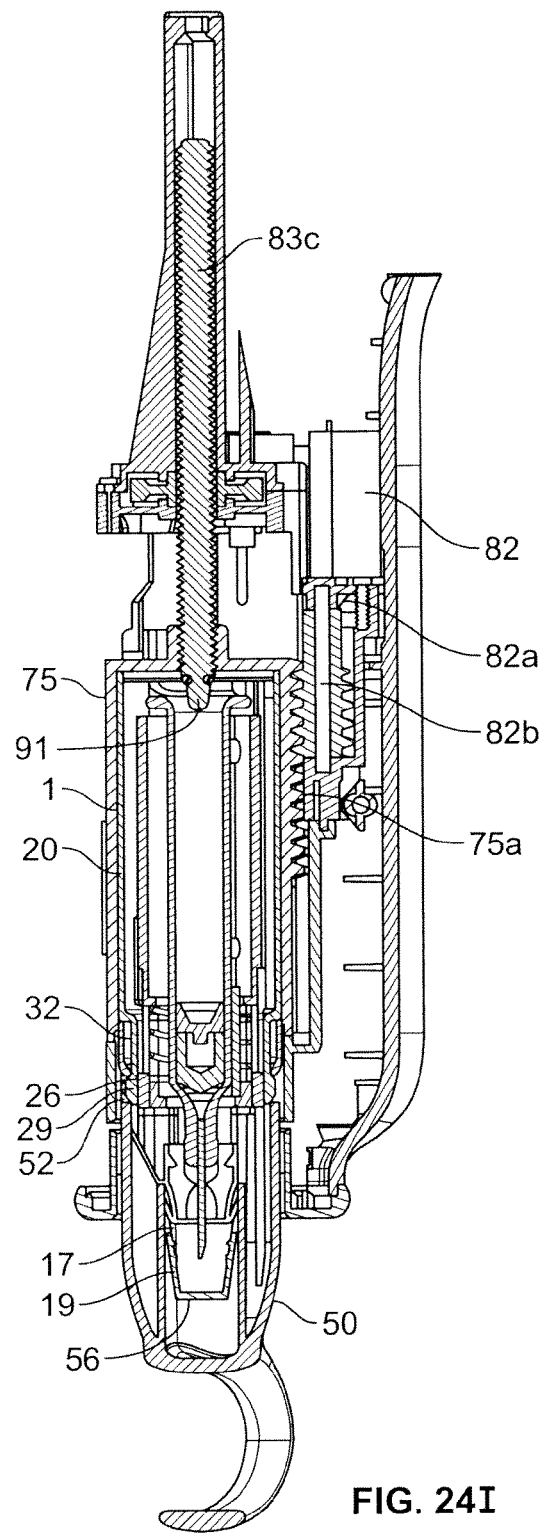

In an eighth stage of a typical use operation, as shown at FIGS. 23i and 24i, the cassette unit holder 75 and cassette unit 1 carried thereby have been returned to a position slightly forward of the 'cassette receipt' position of FIGS. 23b and 24b. Such return is achieved by the drive action of worm drive 82b on rack 75a of the cassette unit holder. The worm drive 82b receives axial drive from first motor 82; 1042 via gear 82a in response to a return command from motor drive circuits 1042 acting under the control of motor control MCU 1040, which in turn communicates with main MCU 1010. Threaded screw 83c with end-piece 91 locates in the 'at rest' position.

Also as shown at FIGS. 23i and 24i, the cap 50 with needle sheath 17 and rigid needle shield 19 has now been replaced on the cassette unit 1 following completion of the injection procedure. During recapping needle cover gripper 56 has been displaced forwards slightly. As shown at FIG. 24i, the shuttle lock control 32 is in the third 'cassette used' position, locating intermediate the first and second shuttle lock control positions (see also FIGS. 8b, 9c, 10c and 11c). The inner face of the locking arm 26 of the cassette unit housing 20 is again blocked, thereby preventing any inwards movement thereof and so effectively also thereby, preventing any disengagement of the angled tip 29 of that locking arm 26 from socket through-hole 52 of the removable cap 50.

As the cassette unit holder 75 is returned forwards the leading edge thereof interacts with sprung-loaded cassette unit-unlock cams 88a, 88b to move them from their 'head upright' to 'head bowed' positions. When in the 'head bowed' position the rounded head 89a, 89b of each cam 88a, 88b presses on engaging tip 95 of locking arm 94 to move that locking arm 94 out of locking engagement with the locking aperture and thus, to allow the cassette unit 1 to be released from the cassette unit holder 75.

The screen 72; 1070 now displays a message instructing the user to remove the cassette unit 301 from the drive unit 70. The user accordingly removes the cassette unit 1. The screen 72; 1070 then displays a message confirming that the cassette removal operation is complete. A battery check and/or data communication step may also be performed. The user then hits the power button to turn the drive unit off and the drive unit is stowed in the position as shown at FIGS. 23a and 24a until powered-up for a subsequent injection operation.

The auto-injector described herein is suitable for the injected delivery of drug, particularly for the treatment and/or prophylaxis of a number of diseases, disorders or conditions, including infections (viral, e.g. HIV infection, bacterial, fungal and parasitic); endotoxic shock associated with infection; inflammatory diseases/autoimmunity such as osteoarthritis, rheumatoid arthritis, psoriatic arthritis, systemic lupus erythematosus (SLE), ankylosing spondilitis, COPD, asthma, Alzheimer's Disease, Crohn's disease, ulcerative colitis, irritable bowel syndrome and psoriasis; immune mediated inflammatory disorders of the central and peripheral nervous system such as multiple sclerosis and Guillain-Barr syndrome; graft-versus-host disease; organ transplant rejection; pain; cancer (including solid tumours such as melanomas, hepatoblastomas, sarcomas, squamous cell carcinomas, transitional cell cancers, ovarian cancers and hematologic malignancies, acute myelogenous leukaemia, chronic myelogenous leukemia, gastric cancer and colon cancer); congenital disorders, e.g. cystic fibrosis and sickle cell anaemia; growth disorders; epilepsy; treatment of infertility; heart disease including ischaemic diseases such as myocardial infarction as well as atherosclerosis and intravascular coagulation; bone disorders such as osteopenia and osteoporosis; and metabolic/idiopathic disease, e.g. diabetes.

In embodiments, the syringe of the auto-injector herein contains a liquid drug formulation, which is designed for refrigerated rest (e.g. at from 2-8° C.) and for injected delivery at room temperature (e.g. at or about 18-30° C.). In embodiments, the viscosity of the liquid drug formulation is less than 120 mPa·s (120 centipoise), in embodiments less than 100 mPa·s (100 centipoise) at a delivery temperature of 20° C.

Appropriate drugs may thus be selected from biologically active agents, including chemical entities, polysaccharides, steroids and, especially, naturally occurring and recombinant proteins, including glycoproteins, polypeptides and oligopeptides and polymeric derivatives thereof. Particular proteins, polypeptides and oligopeptides include hormones, such as insulin, epinephrine, norepinephrine, adrenocorticotrophin, somatotropin, erythropoietin and oxytocin; cytokines, such as lymphokines, chemokines and interleukins and receptors therefor, e.g. interleukin (IL)-1α, IL-1β, IL-1R, IL-2, IL-3, IL-4, IL-5, IL-6, IL-13, IL17, interferon (IFN)-α, IFN-β, IFN-γ, granulocyte monocyte colony stimulating factor, tumour necrosis factor-α; growth factors, such as nerve growth factor and platelet-derived growth factor; enzymes, such as tissue plasminogen activator; and, especially, immunoglobulins. Immunoglobulins include whole antibodies and functionally active fragments and/or derivatives thereof, for example polyclonal, monoclonal, recombinant, multi-valent, mono- or multi-specific, humanised or chimeric antibodies, single chain antibodies, Fab fragments, Fab' and F(ab')$_2$ fragments. Polymeric derivatives of such proteins, polypeptides and oligopeptides include derivatives formed between the protein, polypeptide or oligopeptide and a naturally occurring or synthetic polymer, e.g. a polysaccharide or a polyalylklene polymer such as a poly(ethyleneglycol) [PEG] or derivative thereof, e.g. methoxypoly (ethyleneglycol) [mPEG]. Particular agents include growth hormones and hormones for the treatment of infertility. Other particular agents are for the treatment of epilepsy such as brivaracetam and seletracetam.

The auto-injector device herein has been found to be of particular utility where the drug is an immunoglobulin or a fragment thereof, especially a PEGylated or mPEGylated antibody fragment.

The liquid drug formulations herein are typically aqueous formulations, which comprise the drug in solution and additionally other optional formulation components, which may include buffers (e.g. lactate, acetate), NaCl, and pH modifiers (e.g. NaOH).

The auto-injector device herein has been found to be of particular utility wherein the concentration of the drug (e.g. a therapeutic biologic type drug) in the liquid drug formulation is quite high. In particular, where the drug is a pegylated antibody the auto-injector device has been found to be of particular utility wherein the concentration of the drug is greater than 100 mg/ml, particularly greater than 150 mg/ml such as 200 mg/ml.

It is to be understood that the foregoing description is merely illustrative and is not to be limited to the details given herein. While several embodiments have been provided in the present disclosure, it should be understood that the disclosed systems, devices, and methods, and their components, may be embodied in many other specific forms without departing from the scope of the disclosure.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein. All references cited herein are incorporated by reference in their entirety and made part of this application.

The application of which this description and claims form part may be used as a basis for priority in respect of any subsequent application. The claims of such subsequent application may be directed to any feature or combination of features described herein. They may take the form of product, method or use claims and may include, by way of example and without limitation, one or more of the following claims.

The invention claimed is:

1. A cassette unit for use with an auto-injector having an electrically powered drive unit, said cassette unit comprising:
   a cassette unit housing defining a cassette unit housing cavity, a rearward entrance to said cavity and a forward needle projection aperture;
   said cassette unit housing cavity arranged for receipt of a syringe comprising:
      a barrel for containing a volume of a liquid drug formulation, said barrel defining a flange at the rear end thereof and a forward shoulder at the forward end thereof;
      a hollow needle at a front end of said barrel, said hollow needle defining a needle tip for dispensing of said liquid drug formulation; and
      a plunger that is axially movable within the barrel; and
   in capping relationship with said rearward entrance of the cassette unit housing, a cassette unit end-cap, said cassette unit end-cap defining a drive rod-receiving opening for receipt of a drive rod for providing forward axial drive to said plunger; and
   a biasing element defining a biasing relationship between the cassette unit end-cap and the flange of the syringe, for urging the syringe forwards in relation to the cassette unit end cap.

2. A cassette unit according to claim 1, wherein said drive rod-receiving opening is defined by a periphery, said periphery is provided with a forward skirt and said biasing element is arranged for receipt about said forward skirt.

3. A cassette unit according to claim 1, wherein said biasing element is provided as a separate component to the cassette unit end-cap.

4. A cassette unit according to claim 1, wherein said biasing element is provided integrally with the cassette unit end-cap.

5. A cassette unit according to claim 1, wherein the end-cap is arranged for snap-fit relationship with the cassette unit housing.

6. A cassette unit according to claim 1, additionally comprising one or more shoulder support features for supporting said forward shoulder of the syringe.

7. A cassette unit according to claim 6, further comprising a needle cover defining a needle sheath for sheathing of said needle tip, wherein said one or more shoulder support features locate between the needle cover and the forward shoulder of the syringe.

8. A cassette unit according to claim 7, wherein said needle cover is provided with a needle sheath cover for covering the needle sheath thereof and the one or more shoulder support features locate between said needle sheath cover and the forward shoulder of the syringe.

9. A cassette unit according to claim 8, wherein the needle sheath cover is comprised of a rigid material.

10. A cassette unit according to claim 6, wherein the one or more shoulder support features are in snap-fit arrangement between the needle cover and the forward shoulder of the syringe.

11. A cassette unit according to claim 6, wherein the one or more shoulder support features are defined by one or more separate shoulder support parts provided to the syringe.

12. A cassette unit according to claim 1, additionally comprising axially movable within the barrel for forward movement into contact with said plunger, a plunger slaving part defining a circumferential wall arranged for frictional sliding relationship with the inner wall of the barrel, a rear drive-receiving face and a front plunger-contacting face.

13. A cassette unit according to claim 12 additionally comprising in capping relationship with said rearward entrance of the cassette unit housing, a cassette unit end-cap, said cassette unit end-cap defining a drive rod-receiving opening for receipt of a drive rod for providing forward axial drive to said plunger slaving part.

14. A cassette unit according to claim 13, wherein in a pre-use configuration, the plunger slaving part is shaped for releasable engagement with the cassette unit end-cap.

15. A cassette unit according to claim 14, wherein said drive rod-receiving opening is defined by a periphery and said plunger slaving part is shaped for releasable engagement in said pre-use configuration with said periphery.

16. A cassette unit according to claim 15, wherein said drive rod-receiving opening is defined by a peripheral rim and said plunger slaving part is shaped for releasable engagement in the pre-use configuration with said peripheral rim.

17. A cassette unit according to claim 14, wherein said drive rod-receiving opening is defined by a periphery, said periphery is provided with a forward skirt and said plunger slaving part is shaped for releasable engagement in the pre-use configuration with said forward skirt.

18. A cassette unit according to claim 17, wherein the forward skirt is provided with an inner-facing rim and said plunger slaving part is shaped for releasable engagement in the pre-use configuration with said inner-facing rim.

19. A cassette unit according to claim 14, wherein the plunger slaving part defines a circumferential rim for releasable engagement in the pre-use configuration with the cassette unit end-cap.

20. A cassette unit according to claim 14, wherein the plunger slaving part defines a circumferential trough for releasable engagement in the pre-use configuration with the cassette unit end-cap.

21. A cassette unit according to claim 14, wherein the plunger slaving part is releasable from the cassette unit end-cap in response to forward axial drive provided to said rear drive-receiving face thereof.

22. A cassette unit according to claim 14, wherein said plunger slaving part arranged such that when a forward drive load is applied to said rear drive-receiving face to bring the front plunger-contacting face into contact with the plunger the forward drive load is evenly transmitted to the plunger.

23. A cassette unit according to claim 12, wherein said circumferential wall of the plunger slaving part is provided with one or more slide restrictors that restrict frictional sliding movement thereof in relation to the inner wall of the barrel.

24. A cassette unit according to claim 23, wherein said one or more slide restrictors are arranged to increase the resistance thereof to frictional sliding movement.

25. A cassette unit according to claim 23, wherein each of the one or more slide restrictors comprises a flexible vane arranged to flex slightly in response to frictional sliding movement of the plunger slaving part.

26. A cassette unit according to claim 24, wherein said one or more slide restrictors are arranged to increase the initial resistance to forward frictional sliding movement but to impart lesser resistance to said forward frictional sliding movement once movement is underway.

27. A cassette unit according to claim 23, wherein the one or more slide restrictors are arranged to more greatly increase the resistance to a backward frictional sliding movement than to the forward frictional sliding movement.

28. A cassette unit according to claim 23, wherein said one or more slide restrictors are arranged at evenly spaced intervals around the circumferential wall.

29. A cassette unit according to claim 12, wherein the front plunger-contacting face of plunger slaving part is arranged for engagement with the plunger.

30. A cassette unit according to claim 12, wherein the diameter of the plunger slaving part corresponds to the diameter of the plunger.

31. A cassette unit according to claim 12, wherein the plunger is made of a material that is resiliently compressible and the plunger slaving part is made of a less compressible material.

32. A cassette unit according to claim 31, wherein the plunger slaving part is made of a rigid material.

33. A cassette unit according to claim 12, wherein the rear drive-receiving face of the plunger slaving part has a central recess for receipt of a drive transfer element.

34. A cassette unit according to claim 33, wherein said central recess is shaped such that said drive transfer element is rotatable therein.

35. A cassette unit according to claim 33, wherein said central recess is of conical form.

36. A cassette unit according to claim 33, wherein said central recess tapers to a square-cut end.

37. A cassette unit according to claim 12, wherein the plunger slaving part is comprised of a coloured material to provide a clear visual indicator of the position of the plunger within the barrel of the syringe.

38. A cassette unit according to claim 1, wherein the end-cap is arranged for snap-fit relationship with the cassette unit housing.

39. A cassette unit according to claim 1, wherein the housing receives a syringe containing a liquid drug formulation.

40. An auto-injector comprising:
(a) a cassette unit according to claim 1; and
(b) a drive unit comprising:
a drive unit housing defining a docking cavity and a needle delivery aperture, wherein said docking cavity is arranged for docking receipt of the cassette unit at a docking position, whereupon said cassette unit and/or said syringe is movable from a rest position, in which the needle tip of the syringe is within the drive unit housing to a use position, in which the needle tip protrudes from said needle delivery aperture; and
a drive arrangement, said drive arrangement comprising
one or more electrically powered sources of axial drive;
a first drive transfer element for transferring said axial drive to the cassette unit and/or to the syringe for advancing the syringe to said use position; and
a second drive transfer element for subsequently transferring the axial drive to the plunger slaving part and hence, to the plunger of the syringe for moving the plunger into the barrel of the syringe to eject at least part of said volume of liquid drug formulation.

41. An auto-injector according to claim 40, wherein the second drive transfer element is in the form of a rotating screw or worm drive.

42. An auto-injector according to claim 40, wherein the second drive transfer element defines a drive end arranged for receipt by a central recess of the plunger or of the rear drive-receiving face of the plunger slaving part.

43. An auto-injector according to claim 42, wherein said drive end defines a conical or hemispherical tip and said central recess is of conical form to guide and centre said conical or hemispherical tip therein.

44. An auto-injector according to claim 43, wherein the angle of the conical recess is greater than the angle of the conical or hemispherical tip.

45. An auto-injector according to claim 40, wherein the drive unit includes a cassette unit holder for holding the cassette unit within the drive unit housing.

46. An auto-injector according to claim 45, wherein the cassette unit holder is movable within the drive unit, thereby allowing for movement of the cassette unit within the drive unit.

47. An auto-injector according to claim 45, wherein the cassette unit holder is provided with one or more cassette unit locking features for reversibly locking the cassette unit there within.

48. An auto-injector according to claim 47, wherein the one or more cassette unit locking features are arranged to be in a locking position when the cassette unit is in said docking position.

49. An auto-injector according to claim 48, wherein in the locking position the one or more locking features of the cassette unit housing align with features of the cassette unit holder.

50. An auto-injector according to claim 47, wherein each or any of the cassette unit locking features comprises a latching feature, lock tab feature or snap-lock feature.

51. An auto-injector according to claim 47, wherein each or any of the cassette unit locking features bias towards the cassette locking position.

52. A cassette unit for use with an auto-injector having an electrically powered drive unit, said cassette unit comprising:
a cassette unit housing defining a cassette unit housing cavity, a rearward entrance to said cavity and a forward needle projection aperture;
said cassette unit housing cavity arranged for receipt of a syringe comprising:
a barrel;
a needle at a front end of said barrel; and
a plunger that is axially movable within the barrel; and
in capping relationship with said rearward entrance of the cassette unit housing, a cassette unit end-cap, said cassette unit end-cap defining a drive rod-receiving opening for receipt of a drive rod for providing forward axial drive to said plunger; and
a biasing element defining a biasing relationship between the cassette unit end-cap and an end flange of the syringe barrel, thereby urging the syringe forwards in relation to the cassette unit end cap.

53. A cassette unit comprising:
a housing defining a housing cavity arranged for receipt of a syringe;
a cassette unit end-cap defining a drive rod-receiving opening for receipt of a drive rod for providing forward axial drive to a plunger provided within the syringe; and
a biasing element defining a biasing relationship between the cassette unit end-cap and a flange of the syringe, for urging the syringe forwards in relation to the cassette unit end-cap.

54. A cassette unit according to claim 53, wherein said drive rod-receiving opening is defined by a periphery, said periphery is provided with a forward skirt and said biasing element is arranged for receipt about said forward skirt.

55. A cassette unit according to claim 53, wherein said biasing element is provided as a separate component to the cassette unit end-cap.

56. A cassette unit according to claim 53, wherein said biasing element is provided integrally with the cassette unit end-cap.

57. A cassette unit according to claim 54, wherein the biasing element is configured to abut a forward end of the cassette unit end-cap and to abut the flange of the syringe so as to define a sprung biasing relationship between said end-cap and said flange.

* * * * *